United States Patent
Matoba et al.

(10) Patent No.: US 10,066,238 B2
(45) Date of Patent: Sep. 4, 2018

(54) METHODS FOR PRODUCING ANTIBODIES

(71) Applicant: University of Louisville Research Foundation, Inc., Louisville, KY (US)

(72) Inventors: Nobuyuki Matoba, Owensboro, KY (US); Adam Husk, Owensboro, KY (US)

(73) Assignee: UNIVERSITY OF LOUISVILLE RESEARCH FOUNDATION, INC., Louisville, KY (US)

(*) Notice: Subject to any disclaimer, the term of this patent is extended or adjusted under 35 U.S.C. 154(b) by 84 days.

(21) Appl. No.: 14/767,252

(22) PCT Filed: Feb. 11, 2014

(86) PCT No.: PCT/US2014/015861
§ 371 (c)(1),
(2) Date: Aug. 11, 2015

(87) PCT Pub. No.: WO2014/124457
PCT Pub. Date: Aug. 14, 2014

(65) Prior Publication Data
US 2015/0368661 A1      Dec. 24, 2015

Related U.S. Application Data

(60) Provisional application No. 61/763,366, filed on Feb. 11, 2013.

(51) Int. Cl.
*A61K 39/42* (2006.01)
*C12N 15/82* (2006.01)
*C07K 16/10* (2006.01)

(52) U.S. Cl.
CPC .......... *C12N 15/8258* (2013.01); *C07K 16/10* (2013.01); *C07K 16/1018* (2013.01);
(Continued)

(58) Field of Classification Search
None
See application file for complete search history.

(56) References Cited

U.S. PATENT DOCUMENTS

2002/0159958 A1    10/2002   Hiatt et al.
2004/0110930 A1     6/2004   Reinl et al.
(Continued)

FOREIGN PATENT DOCUMENTS

WO    WO 2012/045082    *  4/2012    .............. C12P 21/08
WO    2012-098119 A2      7/2012

OTHER PUBLICATIONS

Ko, Brodzik, & Steplewski, Production of Antibodies in Plants: Approaches and Perspectives. A.V. Karasev (ed.) Plant-produced Microbial Vaccines. 55, Current Topics in Microbiology and Immunology 332 © Springer-Verlag Berlin Heidelberg 2009.*

(Continued)

*Primary Examiner* — Janet L Andres
*Assistant Examiner* — Stuart Snyder
(74) *Attorney, Agent, or Firm* — Stites & Harbison, PLLC; Terry L. Wright

(57) ABSTRACT

Methods for producing antibodies are provided and include transforming a plant cell with a nucleic acid encoding a heavy chain of an antibody, a light chain of an antibody, and a linking polypeptide connecting the heavy chain to the light chain. The nucleic acid is then expressed in the plant cell, such that, upon expression the linking polypeptide is cleaved to separate the heavy chain from the light chain. Isolated nucleic acid sequences, expression vectors, and transformed plant cells useful for producing the antibodies are also provided. Further provided are methods for treating a viral infection and include the steps of obtaining an antibody (Continued)

produced by the above-described methods and then administering the antibody to a subject.

14 Claims, 12 Drawing Sheets

Specification includes a Sequence Listing.

(52) U.S. Cl.
 CPC ...... *C07K 16/1045* (2013.01); *C07K 16/1063* (2013.01); *C12N 15/8257* (2013.01); *C07K 2317/13* (2013.01); *C07K 2317/14* (2013.01); *C07K 2317/76* (2013.01); *C07K 2317/92* (2013.01)

(56) References Cited

U.S. PATENT DOCUMENTS

2005/0241023 A1  10/2005  Hein et al.
2006/0252096 A1* 11/2006  Zha ........................ C07K 16/00
                                                                    435/7.1
2008/0187954 A1   8/2008  Kallmeier et al.

OTHER PUBLICATIONS

Goodin et al. "Nicotiana benthamiana: Its History and Future as a Model for Plant—Pathogen Interactions", Mol. Plant-Micobe Interact. 2008; 21(9): 1015-1026.*
Chapman and Lu, "Precisely tuned antibodies nab HIV", Nature, 2011; 477: 466-470 and supplementary material page.*
Muynck et al. "Production of antibodies in plants: status after twenty years", Plant Biotech. J. 2010; 8: 529-563.*
Huang J, et al. Broad and potent neutralization of HIV-1 by a gp41-specific human antibody. Nature 491:406-412.
Diskin R, et al. 2011. Increasing the potency and breadth of an HIV antibody by using structure-based rational design. Science 334:1289-1293.
Throsby M, et al. 2008. Heterosubtypic neutralizing monoclonal antibodies cross-protective against H5N1 and H1N1 recovered from human IgM+ memory B cells. PLoS ONE 3:e3942.
Alexandre KB, et al. 2011. Binding of the Mannose-Specific Lectin, Griffithsin, to HIV-1 gp120 Exposes the CD4− Binding Site. J. Virol. 85:9039-9050.
Sattentau Q. 2008. Avoiding the void: cell-to-cell spread of human viruses. Nat. Rev. Microbiol. 6:815-826.
Provine NM, et al. 2012. The neutralization sensitivity of viruses representing human immunodeficiency virus type 1 variants of diverse subtypes from early in infection is dependent on producer cell, as well as characteristics of the specific antibody and envelope variant. Virology 427:25-33.
Monel B, et al. 2012. HIV cell-to-cell transmission requires the production of infectious virus particles and does not proceed through env-mediated fusion pores. J. Virol. 86:3924-3933.
Abela IA, et al. 2012. Cell-cell transmission enables HIV-1 to evade inhibition by potent CD4bs directed antibodies. PLoS Pathog. 8:e1002634.
Selhorst P, et al. 2012. In vitro activities of candidate microbicides against cell-associated HIV. Antimicrob. Agents Chemother. 56:805-815.
Korean Intellectual Property Office, International Search Report issued in corresponding Application No. PCT/US2014/015861, dated May 28, 2014.
2012. Global report: UNAIDS report on the global AIDS epidemic { 2012. Joint United Nations Programme on HIV/AIDS.
Buckheit KW, et al. 2012. Factors Important to the Prioritization and Development of Successful Topical Microbicides for HIV-1. Mol. Biol. Int. 2012:781305. doi:10.1155/2012/781305.
Mcgowan I. 2010. Microbicides for HIV prevention: reality or hope? Curr. Opin. Infect. Dis. 23:26-31.
Van Damme L, et al. 2012. Current status of topical antiretroviral chemoprophylaxis. Curr. Opin. HIV AIDS 6:520-525.
Abdool Karim Q, et al. 2010. Effectiveness and safety of tenofovir gel, an antiretroviral microbicide, for the prevention of HIV infection in women. Science 329:1168-1174.
Holmes D. 2012. FDA treads carefully with PrEP. Lancet Infect. Dis. 12:515-516.
Macklin R, et al. 2012. Given financial constraints, it would be unethical to divert antiretroviral drugs from treatment to prevention. Health Aff. 31:1537-1544.
Hessell AJ, et al. 2009. Broadly neutralizing human anti-HIV antibody 2G12 is effective in protection against mucosal SHIV challenge even at low serum neutralizing titers. PLoS Pathog. 5:e1000433.
Hessell AJ, et al. 2010. Broadly Neutralizing Monoclonal Antibodies 2F5 and 4E10, Directed Against the Human Immunodeficiency Virus Type 1 (HIV-1) gp41 Membrane Proximal External Region (MPER), Protect Against SHIVBa-L Mucosal Challenge. J. Virol. 84:1302-1313.
Burton DR, et al. 2011. Limited or no protection by weakly or nonneutralizing antibodies against vaginal SHIV challenge of macaques compared with a strongly neutralizing antibody. Proc. Natl. Acad. Sci. U.S.A. 108:11181-11186.
Veazey RS, et al. 2003. Prevention of virus transmission to macaque monkeys by a vaginally applied monoclonal antibody to HIV-1 gp120. Nat. Med. 9:343-346.
Watkins JD, et al. 2011. An anti-HIV-1 V3 loop antibody fully protects cross-clade and elicits T-cell immunity in macaques mucosally challenged with an R5 clade C SHIV. PLoS ONE 6:e18207.
Klein F, et al. 2012. HIV therapy by a combination of broadly neutralizing antibodies in humanized mice. Nature 492:118-122.
Moldt B, et al. 2012. Highly potent HIV-specific antibody neutralization in vitro translates into effective protection against mucosal SHIV challenge in vivo. Proc. Natl. Acad. Sci. U.S.A. 109:18921-18925.
Wu X, et al. 2010. Rational design of envelope identifies broadly neutralizing human monoclonal antibodies to HIV-1. Science 329:856-861.
Wilen CB, et al. 2011. Phenotypic and immunologic comparison of clade B transmitted/founder and chronic HIV-1 envelope glycoproteins. J. Virol. 85:8514-8527.
Parrish NF, et al. 2012. Transmitted/founder and chronic subtype C HIV-1 use CD4 and CCR5 receptors with equal efficiency and are not inhibited by blocking the integrin alpha4beta7. PLoS Pathog. 8:e1002686.
Veselinovic M, et al. 2012. Topical gel formulation of broadly neutralizing anti-HIV-1 monoclonal antibody VRC01 confers protection against HIV-1 vaginal challenge in a humanized mouse model. Virology 432:505-510.
Wu X, et al. 2012. Selection Pressure on HIV-1 Envelope by Broadly Neutralizing Antibodies to the Conserved CD4− Binding Site. J. Virol. 86:5844-5856.
Pirrone V, et al. 2011. Combinatorial approaches to the prevention and treatment of HIV-1 infection. Antimicrob. Agents Chemother. 55:1831-1842.
Giritch A, et al. 2006. Rapid high-yield expression of full-size IgG antibodies in plants coinfected with noncompeting viral vectors. Proc. Natl. Acad. Sci. U.S.A. 103:14701-14706.
Kouokam JC, et al. 2011. Investigation of griffithsin's interactions with human cells confirms its outstanding safety and efficacy profile as a microbicide candidate. PLoS ONE 6:e22635.
O'Keefe BR, et al. 2009. Scaleable manufacture of HIV-1 entry inhibitor griffithsin and validation of its safety and efficacy as a topical microbicide component. Proc. Natl. Acad. Sci. U.S.A. 106:6099-6104.
Marillonnet S, et al. 2005. Systemic Agrobacterium tumefaciens-mediated transfection of viral replicons for efficient transient expression in plants. Nat. Biotechnol. 23:718-723.
Matoba N, et al. 2010. HIV-1 neutralization profile and plant-based recombinant expression of actinohivin, an Env glycan-specific lectin devoid of T-cell mitogenic activity. PLoS ONE 5:e11143.

(56) References Cited

OTHER PUBLICATIONS

Zhang PF, et al. 1999. Primary virus envelope cross-reactivity of the broadening neutralizing antibody response during early chronic human immunodeficiency virus type 1 infection. J. Virol. 73:5225-5230.
Li M, et al. 2006. Genetic and Neutralization Properties of Acute and Early Subtype C Human Immunodeficiency Virus Type 1 Molecular env Clones from Heterosexually Acquired Infections in Southern Africa. J. Virol. 80:11776-11790.
Blish CA, et al. 2009. Cross-subtype neutralization sensitivity despite monoclonal antibody resistance among early subtype A, C, and D envelope variants of human immunodeficiency virus type 1. J. Virol. 83:7783-7788.
Montefiori DC 2011, posting date. Protocol for the Preparation and Titration of HIV-1 Env-pseudotyped Viruses. Los Alamos National Security, LLC. http://www.hiv.lanl.gov/content/nab-reference-strains/html/Protocol-for-Preparation-and-Titration-of-HIV-1-Env-pseudotyped-Viruses-Dec.-2011.pdf.
Landau NR, et al. 1992. Packaging system for rapid production of murine leukemia virus vectors with variable tropism. J. Virol. 66:5110-5113.
Deng H, et al. 1996. Identification of a major co-receptor for primary isolates of HIV-1. Nature 381:661-666.
De Muynck B, et al. 2010. Production of antibodies in plants: status after twenty years. Plant Biotechnol. J. 3:529-563.
Zhang B, et al. 2011. Coordinate expression of multiple proteins in plant cells by exploiting endogenous kex2p-like protease activity. Plant Biotechnol. J. 9:970-981.
Kinal H, et al. 1995. Processing and secretion of a virally encoded antifungal toxin in transgenic tobacco plants: evidence for a Kex2p pathway in plants. Plant Cell 7:677-688.
Neff CP, et al. 2011. A topical microbicide gel formulation of CCR5 antagonist maraviroc prevents HIV-1 vaginal transmission in humanized RAG-hu mice. PLoS ONE 6:e20209.
Ma JK, et al. 2003. The production of recombinant pharmaceutical proteins in plants. Nat. Rev. Genet. 4:794-805.
Huang Z, et al. 2009. High-level rapid production of full-size monoclonal antibodies in plants by a single-vector DNA replicon system. Biotechnol. Bioeng. 106:9-17.
Sainsbury F, et al. 2009. pEAQ: versatile expression vectors for easy and quick transient expression of heterologous proteins in plants. Plant Biotechnol. J. 7:682-693.
Vezina LP, et al. 2009. Transient co-expression for fast and high-yield production of antibodies with human-like N-glycans in plants. Plant Biotechnol. J. 7:442-455.
Pogue GP, et al. 2010. Production of pharmaceutical-grade recombinant aprotinin and a monoclonal antibody product using plant-based transient expression systems. Plant Biotechnol. J. 8:638-654.
Forthal DN, et al. 2010. Fc-glycosylation influences Fcgamma receptor binding and cell-mediated anti-HIV activity of monoclonal antibody 2G12. J. Immunol. 185:6876-6882.
Strasser R, et al. 2008. Generation of glyco-engineered Nicotiana benthamiana for the production of monoclonal antibodies with a homogeneous human-like N-glycan structure. Plant Biotechnol. J. 6:392-402.
Zeitlin L, et al. 2011. Enhanced potency of a fucose-free monoclonal antibody being developed as an Ebola virus immunoprotectant. Proc. Natl. Acad. Sci. U.S.A. 108:20690-20694.
Hessell AJ, et al. 2007. Fc receptor but not complement binding is important in antibody protection against HIV. Mature 449:101-104.
Forthal DN, et al. 2009. Fc receptor-mediated antiviral antibodies. Cur. Opin. HIV AIDS 4:388-393.
Robinson HL. 2012. Non-neutralizing antibodies in prevention of HIV infection. Expert Opin. Biol. Ther. 13:197-207.
Bosch D, et al. 2010. Plant glycans: friend or foe in vaccine development? Expert Rev. Vaccines 9:835-842.
Jin C, et al. 2008. A plant-derived human monoclonal antibody induces an anti-carbohydrate immune response in rabbits. Glycobiology 18:235-241.
Castilho A, et al. 2011. Rapid high yield production of different glycoforms of Ebola virus monoclonal antibody. PLoS ONE 6:e26040.
Walker LM, et al. 2011. Broad neutralization coverage of HIV by multiple highly potent antibodies. Nature 477:466-470.

* cited by examiner

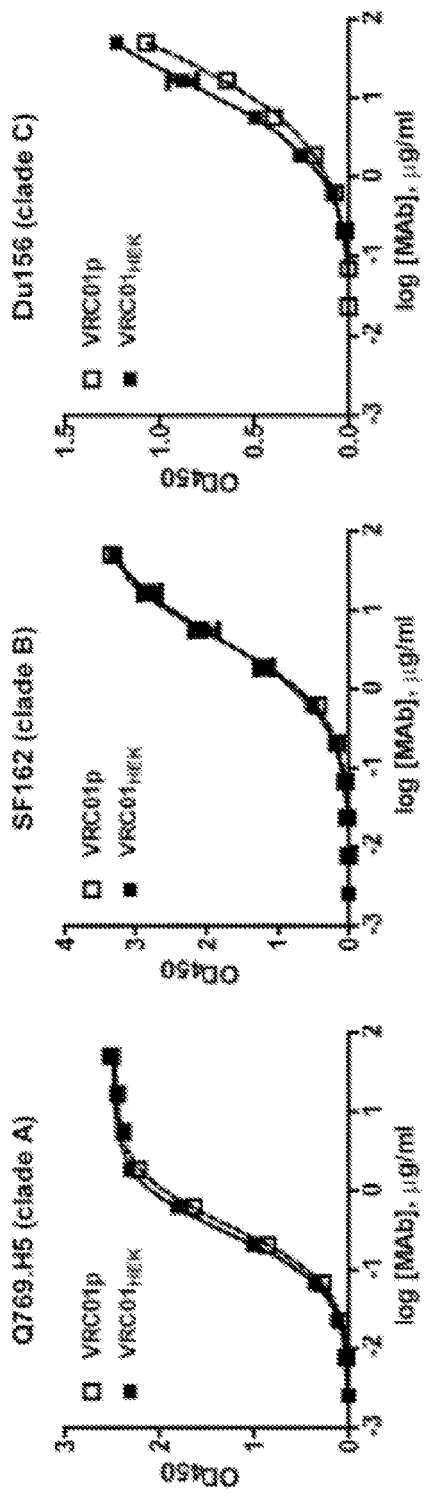
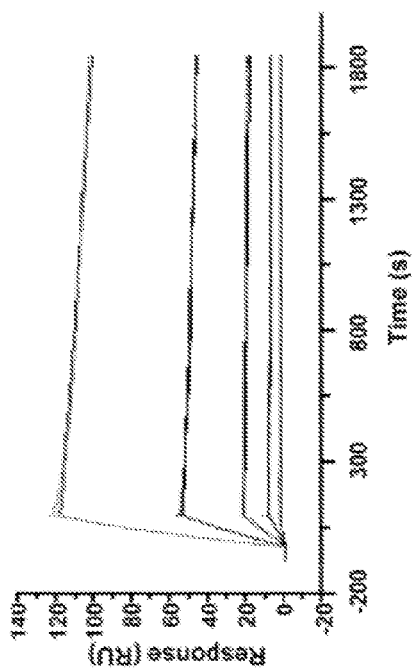
FIG. 3A
FIG. 3B

METHODS FOR PRODUCING ANTIBODIES

RELATED APPLICATIONS

This application claims priority from U.S. Provisional Application Ser. No. 61/763,366, filed Feb. 11, 2013, the entire disclosure of which is incorporated herein by this reference

GOVERNMENT INTEREST

This invention was made with government support under grant number W81XWH-09-2-0022 awarded by Department of Defense, United States Army Medical Research and Material Command. The government has certain rights in the invention.

TECHNICAL FIELD

The presently-disclosed subject matter relates to methods for producing antibodies. In particular, the presently-disclosed subject matter relates to methods for producing antibodies in plants wherein the antibodies are produced from polypeptides encoding the heavy and light chains of the antibody and having a cleavable, linking polypeptide between the heavy and light chains.

BACKGROUND

Despite the slowly declining incidence of global HIV infections in recent years, the HIV/AIDS epidemic causes over 2 million new infections every year, representing one of the leading causes of infection-related deaths worldwide. Because an effective HIV vaccine remains elusive and the majority of new infections occur in the developing countries, there is thus an urgent need for safe, effective, and inexpensive pre-exposure prophylaxis (PrEP) modalities for preventing viral mucosal transmission, such as topical microbicides. Currently, most efforts in microbicide development are focused on small-molecule antiretrovirals (ARVs) that have been developed to treat HIV-infected individuals. This paradigm has emerged since the seminal report published in 2010 on the CAPRISA 004 Phase IIb clinical trial, showing that peri-coital use of a gel containing the reverse-transcriptase (RT) inhibitor tenofovir (TFV) provided modest yet significant protection. Clinical development of ARVs for PrEP can be greatly facilitated by available safety and efficacy information from their therapeutic use. However, it is desirable to expand microbicide candidates to non-ARV-based HIV inhibitors because of concerns for the PrEP/microbicide use of ARVs. For example, potential conflict of priorities between treatment and prevention may arise, and emergence of escape mutants could compromise available therapy options. Human anti-HIV-1 broadly neutralizing monoclonal antibodies (bn-MAbs) may provide attractive options in this context, given their proven protective efficacy against infection upon pre- and/or post-exposure uses in animal challenge models and inherent general safety because of their human origin. A Phase I randomized controlled clinical trial has been recently completed for a vaginal microbicide candidate containing three bnMAbs 2F5, 4E10, and 2G12, showing that daily vaginal administration of the bnMAbs (50 mg each) to healthy women for 12 days was safe and well tolerated.

VRC01 is a CD4-binding site (CD4bs)-specific bnMAb recently isolated from a slowly progressing HIV-1 infected donor. It has remarkable neutralization coverage compared to most other HIV-1-neutralizing MAbs reported to date; about 90% of genetically diverse heterologous HIV-1 strains have been neutralized with 50% inhibitory concentrations ($IC_{50}$) at less than 1 µg/ml in in vitro HIV-1 neutralization assays. Transmitted/founder viruses of A, B, and C clades were shown to be susceptible to VRC01 neutralization. Veselinovic, et al. recently reported that a topical gel formulation of VRC01 protected against vaginal challenge with the chemokine receptor CCR5-using HIV-1 BaL in a humanized mouse model. Collectively, these findings suggest that VRC01 and other similar bnMAbs constitute promising non-ARV anti-HIV-1 molecules as topical microbicide candidates, justifying further preclinical investigation to determine their feasibility.

Notwithstanding the remarkable breadth and potency of VRC01's anti-HIV-1 activity, the existence of VRC01-resistant viruses has been demonstrated in the VRC01 donor and in other broadly neutralizing plasma donors. A recent passive immunotherapy study using a humanized mouse model has shown that a monotherapeutic use of the VRC01-like CD4bs-specific bnMAb NIH45-46$^{G54W}$ failed to control viremia and the emergence of resistant viruses, although combination with four other bnMAbs rendered complete protection. These findings suggest that a single component microbicide based on VRC01 or any other bnMAb may fail to provide sufficient protection and could even lead to the accumulation of resistant strains in circulating virus populations. In practice, a combinatorial strategy will have to be implemented to any microbicide candidates, as has been the case in the treatment of HIV-1-infected patients. Thus, analysis of VRC01's potential for synergy with other microbicide candidates would provide valuable information towards the bnMAb's potential as a component of combination microbicides.

While efficacy and safety are critical aspects in pharmaceutical development, it is also important that microbicide candidates are economically viable. Indeed, this is perhaps the most significant challenge for MAbs, as the current mammalian cell culture-based production system will be difficult to provide the proteins at a cost and scale required for global HIV-1 prevention. Accordingly, a method of producing antibodies, such as anti-HIV VRC01 antibodies, that allows the antibodies to be produced at a high level and in an economical manner would be both highly desirable and beneficial.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods for producing antibodies and, in particular, methods for producing antibodies in plants. In some embodiments, a method for producing an antibody is provided that comprises: transforming a plant cell with a nucleic acid encoding a heavy chain of the antibody, a light chain of the antibody, and a linking polypeptide connecting the heavy chain to the light chain; and expressing the nucleic acid in the plant cell such that, upon expression, the linking polypeptide is cleaved to separate the heavy chain from the light chain. In some embodiments, the plant cell comprises a *Nicotiana* (i.e., a flowering tobacco) plant cell, such as, in some embodiments, a *Nicotiana benthamiana* plant cell.

With respect to the linking polypeptides that are used to connect the components of the antibodies and that are encoded by the nucleic acids used in accordance with the presently-disclosed methods, in some embodiments, the linking polypeptide includes an endoproteinase cleavage site that allows the linking polypeptide to be cleaved by endoproteinases upon expression. For example, in some embodiments, the linking polypeptide comprises a Kex2p enzyme recognition site. In some embodiments, the linking polypeptide having a Kex2p enzyme recognition site is encoded by a nucleic acid having the sequence of SEQ ID NO: 9.

In some embodiments of the methods described herein, the antibody produced in the plant cell comprises a monoclonal antibody. In some embodiments, the antibody is selected from the group consisting of an anti-human immunodeficiency virus VRC01 antibody, an anti-human immunodeficiency virus PGT121, and an anti-influenza CR6261 antibody. In some embodiments, where a VRC01 antibody, a PGT121 antibody, or a CR6261 antibody is produced, the nucleic acid transformed into the plant cell comprises a sequence selected from SEQ ID NOS: 1-4. In other embodiments, the antibody is a secretory IgA antibody. In this regard, in some embodiments, the nucleic acid further encodes a J chain of the secretory IgA antibody as well as a secretory component of the IgA antibody.

Further provided in some embodiments of the presently-described subject matter are methods for producing a mixed population of antibodies. In some embodiments, a method for producing a mixed population of antibodies is provided wherein a plant cell is transformed with a first nucleic acid that encodes a heavy chain of a first antibody, a light chain of the first antibody, and a linking polypeptide connecting the heavy chain of the first antibody to the light chain of the first antibody. The plant cell is further transformed with a second nucleic acid encoding a heavy chain of a second antibody, a light chain of the second antibody, and a linking polypeptide connecting the heavy chain of the second antibody to the light chain of the second antibody. Upon transforming the plant cell with the first nucleic acid and the second nucleic acid, the first nucleic acid and second nucleic acid are then expressed in the plant cell such that, upon expression of the nucleic acids, each linking polypeptide is cleaved to separate each heavy chain from each light chain and thereby produce the first antibody and the second antibody. In some embodiments, the first antibody and the second antibody both bind to the same target protein, including binding to the same epitope or, in certain embodiments, different epitopes on the target protein. In other embodiments, the first antibody and the second antibody bind to different target proteins.

Even further provided, in some embodiments of the methods for producing antibodies described herein, are methods for producing a secretory IgA antibody. In some embodiments, a method for producing a secretory IgA antibody is provided wherein a plant cell is transformed with a first nucleic acid that encodes two components of the secretory IgA antibody selected from the light chain of the secretory IgA antibody, the heavy chain of the secretory IgA antibody, the J chain of the secretory antibody, and the secretory component of the IgA antibody. The first nucleic acid further encodes a linking polypeptide that connects the two components encoded by the first nucleic acid. The plant cell is then transformed with a second nucleic acid that encodes the remaining two components of a secretory IgA antibody as well as another linking polypeptide that connects the two components encoded by the second nucleic acid. Upon subsequent expression of the first nucleic acid and second nucleic acid in the plant cell, each linking polypeptide is then cleaved to separate the two components encoded by the first nucleic acid and the two components encoded by the second nucleic acid to thereby produce the secretory IgA antibody containing all four components.

Still further provided, in some embodiments of the presently-disclosed subject matter are isolated nucleic acid molecules capable of being used in accordance with the above-described methods for producing antibodies. Also provided are plant cells, or progeny thereof, that have been transfected with the nucleic acid molecules. In some embodiments, an isolated nucleic acid molecule is provided that comprises a sequence that encodes a polypeptide including a heavy chain of an antibody, a light chain of an antibody, and a linking polypeptide connecting the heavy chain to the light chain. In other embodiments, an isolated nucleic acid is provided that comprises a sequence encoding a polypeptide including at least two components of a secretory IgA antibody selected from the group consisting of a light chain of the secretory IgA antibody, a heavy chain of the secretory IgA antibody, a J chain of the secretory antibody, and a secretory component of the IgA antibody, with the polypeptide further including a linking polypeptide that connects the two components. In some embodiments, the nucleic acid molecules are operably linked to an expression cassette, such as, in certain embodiments, an expression cassette that directs expression of the nucleic acid molecules in a plant cell.

In even further embodiments of the presently-disclosed subject matter are antibodies produced by the methods described herein. In some embodiments, the antibodies can be used as part of a therapeutic method whereby the antibodies are administered to a subject, alone or in combination with other antiviral agents, to thereby treat a viral infection. For example, in some embodiments, a method of treating a viral infection is provided that comprises the steps of obtaining an antibody produced by the methods of the presently-disclosed subject matter; and administering an effective amount of the antibody to a subject. In some embodiments, administering the antibody comprises topically or vaginally administering the antibody.

Further features and advantages of the present invention will become evident to those of ordinary skill in the art after a study of the description, figures, and non-limiting examples in this document.

BRIEF DESCRIPTION OF THE DRAWINGS

FIGS. 3A-3C include graphs showing a comparison of VRC01p with VRC01$_{HEK}$, including: a graph showing the results of a gp120-enzyme-linked immunosorbent assay (ELISA) using recombinant gp120 proteins from Q769.H5 (clade A), SF162 (clade B), and DU156 (clade C), where the half maximal effective concentrations (EC$_{50}$) of VRC01$_{HEK}$ and VRC01p were determined by non-linear regression analysis to be 0.28 and 0.35 µg/ml, respectively, for gp120$_{Q769.H5}$, 4.24 and 4.11 µg/ml, respectively, for gp120$_{SF162}$, and 15.1 and 67.9 µg/ml, respectively, for gp120$_{DU156}$; a graph showing a representative sensorgram obtained with VRC01p using surface plasmon resonance (SPR) analysis, where each VRC01 protein was captured on a sensor chip via an anti-human IgG (Fc) antibody of IgG1 isotype and varying concentrations of recombinant gp120 from SF162 were used as analytes, where the fitted curves, based on the 1:1 binding kinetics, represent the concentration of gp120 (50, 16.66, 5.55, 1.85, and 0.617 µg/ml from top to bottom), and where the equilibrium dissociation constants, K$_D$, for VRC01$_{HEK}$ and VRC01p were determined to be 3.82±0.60 and 3.97±0.74 nM, respectively; and a graph showing anti-HIV-1 activity of VRC01$_{HEK}$ and VRC01p against Env-pseudotyped SF162 virus in HOS-CD4-CCR5$^+$ cells, where percent neutralization was calculated by dividing luminescence of sample wells by virus-only control wells, where IC$_{50}$ values for each VRC01 were determined by non-linear regression analysis (see Table 1), and where no statistical difference was found based on average IC$_{50}$ values for VRC01$_{HEK}$ and VRC01p;

BRIEF DESCRIPTION OF THE SEQUENCE LISTING

Figure 1A:
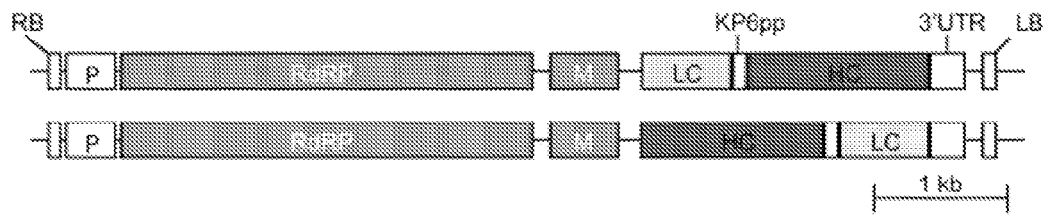
FIGS. 1A-1D include a schematic diagram, a graph, and an image showing single tobamoviral vector-based overexpression of VRC01 in *N. benthamiana*, including: a schematic diagram of two VRC01 vector constructs, L-(KP6pp)-H and H-(KP6pp)-L, where RB/LB indicates right and left borders, P indicates an *Arabidopsis* Act2 promoter, RdRP indicates RNA-dependent RNA polymerase with artificial introns, M indicates movement protein, LC/HC indicates light and heavy chains, KP6pp indicates an amino acid peptide containing two kex2p recognition sites at N- and C-termini, and UTR indicates an untranslated region (FIG. 1A); a graph showing the quantification of VRC01 accumulation in leaf extracts from L-(KP6pp)-H and H-(KP6pp)-L constructs at 5 and 7 dpi, where the amounts, in milligrams per kg of fresh leaf material, of VRC01 were quantified by gp120-ELISA and data are expressed as mean±SEM of biological triplicate (FIG. 1B); an image showing a non-reducing SDS-PAGE analysis of crude extracts of N. benthamiana leaves expressing L-(KP6pp)-H construct VRC01 (VRC01p), where lane 1 includes a control leaf extract and lane 2 includes a VRC01p extract, and where the arrow indicates the position of assembled VRC01 at approximately 150 kDa (FIG. 1C); and an image of a non-reducing SDS-PAGE analysis of purified VRC01p, where the bnMAb was purified by Protein A (lane 1) followed by a Phenyl HP resin (lane 2) and, after the two step purification, the $H_2L_1$ or Fab-Fc byproduct (approximately 100 kDa, present after Protein A purification) was efficiently removed, and VRC01p was purified to greater than 98% (FIG. 1D).

SEQ ID NO: 1 is a nucleic acid sequence encoding an anti-human immunodeficiency (anti-HIV) VRC01 antibody construct that includes a VRC01 light chain (nucleic acids 1-630) directly linked to a linking polypeptide (630-741) that is then directly linked to a VRC01 heavy chain (nucleic acids 742-2097);

SEQ ID NO: 2 is a nucleic acid sequence encoding an anti-HIV VRC01 antibody construct that includes a VRC01 heavy chain (nucleic acids 1-1353) directly linked to a linking polypeptide (nucleic acids 1354-1464) that is then directly linked to a VRC01 light chain (nucleic acids 1465-2097);

SEQ ID NO: 3 is a nucleic acid sequence encoding an anti-influenza CR6261 antibody construct that includes a CR6261 light chain (nucleic acids 1-663) directly linked to a linking polypeptide (nucleic acids 664-774) that is then directly linked to a CR6261 heavy chain (nucleic acids 775-2130);

SEQ ID NO: 4 is a nucleic acid sequence encoding an anti-HIV PGT121 antibody construct that includes a PGT121 light chain (nucleic acids 1-645) directly linked to a linking polypeptide (nucleic acids 646-756) that is then directly linked to a PGT121 heavy chain (nucleic acids 757-2145);

SEQ ID NO: 5 is a nucleic acid sequence encoding an anti-tumor necrosis factor-alpha (TNF-α) secretory IgA antibody construct that includes a secretory IgA light chain (nucleic acids 1-642) directly linked to a linking polypeptide (nucleic acids 643-753) that is then directly linked to a secretory IgA heavy chain (nucleic acids 754-2136);

SEQ ID NO: 6 is a nucleic acid sequence encoding an anti-TNF-α secretory IgA antibody construct that includes a secretory IgA J chain (nucleic acids 1-411) directly linked to a linking polypeptide (nucleic acids 412-522) that is then directly linked to a secretory IgA secretory component (nucleic acids 523-2280);

SEQ ID NO: 7 is a nucleic acid sequence encoding an anti-TNF-α secretory IgA antibody construct that includes a secretory IgA light chain (nucleic acids 1-642) directly linked to a linking polypeptide (643-753) that is then directly linked to a secretory IgA secretory component (nucleic acids 754-2511);

SEQ ID NO: 8 is a nucleic acid sequence encoding an anti-TNF-α secretory IgA antibody construct that includes a secretory IgA heavy chain (nucleic acids 1-1380) directly linked to a linking polypeptide (nucleic acids 1381-1491) that is then directly linked to a secretory IgA J chain (nucleic acids 1492-1905);

SEQ ID NO: 9 is a nucleic acid sequence of a linking polypeptide including a KP6 killer toxin propeptide sequence;

SEQ ID NO: 10 is an amino acid sequence of an anti-human immunodeficiency (anti-HIV) VRC01 antibody construct that includes a VRC01 light chain (amino acids 1-210) directly linked to a linking polypeptide (amino acids 210-247) that is then directly linked to a VRC01 heavy chain (amino acids 248-698);

SEQ ID NO: 11 is an amino acid sequence of anti-HIV VRC01 antibody construct that includes a VRC01 heavy chain (amino acids 1-451) directly linked to a linking polypeptide (amino acids 452-488) that is then directly linked to a VRC01 light chain (amino acids 489-698);

SEQ ID NO: 12 is an amino acid sequence of an anti-influenza CR6261 antibody construct that includes a CR6261 light chain (amino acids 1-221) directly linked to a linking polypeptide (amino acids 222-258) that is then directly linked to a CR6261 heavy chain (amino acids 259-709);

SEQ ID NO: 13 is an amino acid sequence of an anti-HIV PGT121 antibody construct that includes a PGT121 light chain (amino acids 1-215) directly linked to a linking polypeptide (amino acids 216-252) that is then directly linked to a PGT121 heavy chain (amino acids 253-714);

SEQ ID NO: 14 is an amino acid sequence encoding an anti-TNF-α secretory IgA antibody construct that includes a secretory IgA light chain (amino acids 1-214) directly linked to a linking polypeptide (amino acids 215-251) that is then directly linked to a secretory IgA heavy chain (amino acids 252-711);

SEQ ID NO: 15 is an amino acid sequence encoding an anti-TNF-α secretory IgA antibody construct that includes a secretory IgA J chain (amino acids 1-137) directly linked to a linking polypeptide (amino acids 138-174) that is then directly linked to a secretory IgA secretory component (amino acids 175-759);

SEQ ID NO: 16 is an amino acid sequence encoding an anti-TNF-α secretory IgA antibody construct that includes a secretory IgA light chain (amino acids 1-214) directly linked to a linking polypeptide (amino acids 215-251) that is then directly linked to a secretory IgA secretory component (amino acids 252-836);

SEQ ID NO: 17 is a nucleic acid sequence encoding an anti-TNF-α secretory IgA antibody construct that includes a secretory IgA heavy chain (amino acids 1-460) directly linked to a linking polypeptide (amino acids 461-496) that is then directly linked to a secretory IgA J chain (amino acids 497-633);

SEQ ID NO: 18 is an amino acid sequence of a KP6 killer toxin propeptide linker sequence;

SEQ ID NO: 19 is an amino acid sequence of another KP6 killer toxin propeptide linker sequence; and SEQ ID NO: 20 is an amino acid sequence of yet another KP6 killer toxin propeptide linker sequence.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and, "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is based, at least in part, on the discovery that a plant virus vector-based biomanufacturing platform can be efficiently and effectively utilized for the expression of the anti-human immunodeficiency virus (HIV) VRC01 antibody using only a single vector. Previously, the *Agrobacterium tumefaciens*-launched RNA viral vector system developed by Giritch et al. was observed to provide the capability of using plant-based MAb manufacturing technologies, but that method still required the simultaneous delivery of at least two viral vectors to drive expression of the MAb heavy (H) and light (L) chains in planta. In accordance with the presently-disclosed subject matter, a novel system has now been developed that requires only a single viral vector to deliver both MAb chains in a single cistron encoding specific kex2p-like endoproteinase cleavage sites that facilitate post-translational processing of the single chain into individual H and L chains within the trans-Golgi network. The use of such a single vector reduces the regulatory complexity of the manufacturing process, requiring only one viral vector and *Agrobacterium* culture to drive expression of the MAb, such as VRC01. Furthermore, by producing the MAbs in such a manufacturing process, the antibodies can then be used as a component of a topical antiviral capable of providing antiviral synergy in combination with other antiviral agents, including tenofovir (TFV), the CCR5 antagonist maraviroc (MVC), and the mannose-specific antiviral lectin griffithsin (GRFT).

The presently-disclosed subject matter thus includes methods for producing antibodies and, in particular, methods for producing antibodies in plants wherein the antibodies are produced from one or more nucleic acid constructs that encode the components of the antibodies and cleavable, linking polypeptides. In some embodiments of the presently-disclosed subject matter, a method for producing an antibody is provided that comprises: transforming a plant cell with a nucleic acid encoding a heavy chain of the antibody, a light chain of the antibody, and a linking polypeptide connecting the heavy chain to the light chain; and expressing the nucleic acid in the plant cell such that, upon expression of the nucleic acid, the linking polypeptide is cleaved to separate the heavy chain from the light chain.

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a gene product. Thus, exemplary polypeptides include gene products, naturally occurring or native proteins, homologs, orthologs, paralogs, fragments and other equivalents, variants, and analogs of the foregoing. The term "native," when used with reference to a polypeptide, refers to a polypeptide that is encoded by a gene that is naturally present in the genome of an untransformed cell.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can also be a "functional fragment," in which case the fragment retains some or all of the activity of the reference polypeptide as described herein.

The terms "modified amino acid," "modified polypeptide," and "variant" are used herein to refer to an amino acid sequence that is different from the reference polypeptide by one or more amino acids, e.g., one or more amino acid substitutions or additions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein, such as, in the case of antibodies, the ability to bind to a particular epitope.

As one example of a method of producing an antibody in accordance with the presently-disclosed subject matter, in some embodiments, a method of producing an antibody is provided wherein a plant cell is transformed with a nucleic acid, such as the nucleic acid sequence provided in SEQ ID NO: 1, that encodes an anti-HIV VRC01 light chain polypeptide directly linked a linking polypeptide that, in turn, is directly linked to an anti-HIV VRC01 heavy chain polypeptide. Upon transforming the plant cell with that nucleic acid sequence, the entire polypeptide is then expressed. Subsequently, however, during post-translational processing, the linking polypeptide is cleaved, such that the individual heavy chains and light chains are separated from one another and are then allowed to assemble into a VRC01 antibody, which can then be isolated from the plant cell and utilized as part of a method for treating a viral infection, as described in further detail below.

As other examples of nucleic acids encoding heavy and light chains of antibodies and capable of being transformed into a plant cell, in some embodiments, a nucleic acid, such as the nucleic acid provided by SEQ ID NO: 2, is used that encodes an anti-HIV VRC01 heavy chain polypeptide directly linked a linking polypeptide that, in turn, is directly linked to an anti-HIV VRC01 light chain polypeptide. In other embodiments, a nucleic acid, such as the nucleic acid provided by SEQ ID NO: 3, is used that encodes an anti-influenza CR6261 light chain polypeptide directly linked to a linking polypeptide that, in turn, is directly linked to an anti-influenza CR6261 heavy chain polypeptide. In further embodiments, a nucleic acid, such as the nucleic acid provided by SEQ ID NO: 4, is used that encodes an anti-HIV PGT121 light chain polypeptide directly linked to a linking polypeptide that, in turn, is directly linked to an anti-HIV PGT121 heavy chain polypeptide. In some embodiments, the antibody produced by the foregoing methods is selected from an anti-HIV VRC01 antibody, an anti-HIV PGT121 antibody, or an anti-influenza CR6261 antibody. In some embodiments, the nucleic acid sequence used in accordance with the methods is selected from SEQ ID NOS: 1-4.

Further provided, in some embodiments of the presently-described methods, are methods for producing a mixed population of antibodies. In some embodiments, a method for producing a mixed population of antibodies is provided wherein a plant cell is transformed with a first nucleic acid that encodes a heavy chain of a first antibody, a light chain of the first antibody, and a linking polypeptide connecting the heavy chain of the first antibody to the light chain of the first antibody. The plant cell is also transformed with a second nucleic acid encoding a heavy chain of a second antibody, a light chain of the second antibody, and a linking polypeptide connecting the heavy chain of the second antibody to the light chain of the second antibody. Upon transforming the plant cell with the first nucleic acid and the second nucleic acid, the first nucleic acid and second nucleic acid are then expressed in the plant cell such that, upon expression of the nucleic acids, each linking polypeptide is cleaved to separate each heavy chain from each light chain and thereby produce the first antibody and the second antibody. In some embodiments, the first antibody and the second antibody both bind to the same target protein, including binding to the same epitope or, in certain embodiments, different epitopes on the target protein. In some embodiments of the methods for producing mixed populations of antibodies, the first antibody and the second antibody bind to different target proteins.

As one non-limiting example of a method for producing a mixed population of antibodies, in some embodiments, a method for producing antibodies is provided where the one or more plant cells are transformed with a nucleic acid construct encoding anti-influenza CR6261 antibody heavy and light chains that are connected to one another by a linking polypeptide. The plant cells are also transformed with a second nucleic acid construct encoding anti-HIV PGT121 antibody heavy and light chains that are also connected to one another by a linking polypeptide. In some embodiments, the plant cell can be transformed with the nucleic acids in a sequential manner, while, in other embodiments, the plant cells can be transformed with the nucleic acids simultaneously, such as by infiltrating the plants with a mixed bacterial culture that includes one group of bacterial harboring a vector containing the first nucleic acid and a second group of bacteria harboring the second nucleic acid. Regardless of whether the nucleic acids are introduced into the plant cells sequentially or simultaneously, however, after expression of the first nucleic acid and the second nucleic acid in the plant cells, the two linking polypeptides are cleaved and the individual heavy chains and light chains of the anti-influenza CR6261 antibody and the anti-HIV PGT121 antibody are separated from one another. The heavy and light chains then assemble into CR6261 antibodies and PGT121 antibodies that can then be isolated, either together or independently, from the plant cell and utilized.

By making use of nucleic acids encoding components of antibodies separated by linking peptides, the presently-disclosed subject matter thus provides methods for producing a number of different types of antibodies including, but not limited to, monoclonal antibodies, recombinant antibodies, chimeric antibodies, humanized antibodies, bispecific antibodies, catalytic antibodies, single chain antibodies, antibodies from different species (e.g., mouse, goat, rabbit, human, rat, bovine, llama, etc.), anti-idiotypic antibodies, antibodies of different isotype (IgG, IgM, IgE, IgA, etc.), as well as fragments and derivatives thereof (e.g., (Fab)$_2$, Fab, Fv, Fab, 2(Fab), Fab', (Fab')$_2$ fragments). In some embodiments, the antibody is a broadly-neutralizing antibody or, in other words, an antibody that is capable neutralizing infection by multiple viral strains within the same viral family. In some embodiments, the antibody has an IgG isotype, while, in other embodiments, the antibody has an IgA isotype. In some embodiments the antibody is a monoclonal antibody.

Additionally, by making use of the above-described methods, in some embodiments, the methods allow for the production of multiple antibodies from a single introduction of nucleic acids encoding the antibody components in a plant. For example, in some embodiments, the above-described methods can be used to produce two or more monoclonal antibodies from the same plants. Such antibodies can recognize the same or different targets, and can improve the efficacy of the intended uses of the antibodies such as by obtaining synergistic activity or broadening target coverage. In some embodiments, the methods can be used to produce an entire repertoire of antibodies derived from a single individual or animal.

In some embodiments of the above-described methods, a method for producing an antibody is provided where the antibody is not comprised of only a heavy and a light chain, but is instead comprised of a heavy and light chain as well as one or more additional components. As would be recognized by those skilled in the art, certain antibodies, such as IgG antibodies, are comprised of only heavy and light chains, while other antibodies are comprised of heavy and light chains in combination with one or more additional components. For instance, secretory IgA antibodies are generally found as multimeric antibodies that not only include multiple heavy and light chain components, but also include a J chain that connects the monomeric portions of the antibody as well as a secretory component that wraps around the IgA antibody and performs both a binding and protective function.

In this regard, in some embodiments, a secretory IgA antibody can be produced where a single vector construct (i.e., a single nucleic acid molecule) encodes the heavy chain, the light chain, the J chain, and the secretory component of the IgA molecule, with each component being separated from adjacent components in the construct by a cleavable, linking polypeptide. In other embodiments of the presently-disclosed subject matter, secretory IgA antibodies can be produced by making use of multiple constructs where each construct encodes one or more components of the secretory IgA antibody. In some embodiments a method for producing a secretory IgA is provided wherein a plant cell is transformed with a first nucleic acid that encodes two components of the secretory IgA antibody selected the light chain of the secretory IgA antibody, the heavy chain of the secretory IgA antibody, the J chain of the secretory antibody, and the secretory component of the IgA antibody. The first nucleic acid further encodes a linking polypeptide for connecting the two components encoded by the first nucleic acid. The plant cell is then transformed with a second nucleic acid that encodes the remaining two components of a secretory IgA antibody as well as another linking polypeptide that connects the two components encoded by the second nucleic acid. Upon subsequent expression of the first nucleic acid and second nucleic acid in the plant cell, each linking polypeptide is then cleaved to separate the two components encoded by the first nucleic acid and to separate the two components encoded by the second nucleic acid to thereby produce the secretory IgA antibody.

As an example of producing a secretory IgA antibody, in some embodiments, a method of producing a secretory IgA antibody is provided wherein a plant cell is transformed with a first nucleic acid, such as the nucleic acid of SEQ ID NO: 5, that encodes the light chain of a secretory IgA antibody directly linked to a KP6pp linking polypeptide that is then directly linked to the heavy chain of the antibody. The plant cell is then transformed with a second nucleic acid, such as the nucleic acid of SEQ ID NO: 6, that encodes the remaining two components of a secretory IgA antibody, namely the J chain and the secretory component of the IgA antibody, as well as another linking polypeptide that connects the remaining two components. Upon subsequent expression of the first nucleic acid and second nucleic acid in the plant cell, each linking polypeptide is then cleaved to separate the two components encoded by the first nucleic acid and the two components encoded by the second nucleic acid to thereby produce the secretory IgA antibody. Of course, nucleic acids encoding different configurations of the components of a secretory IgA antibody can also be used and are within the scope of the presently-disclosed subject matter. For instance, in other embodiments, a first nucleic acid can encode the light chain and the secretory component of the IgA antibody separated by a linking polypeptide (see, e.g., SEQ ID NO: 7), while the second nucleic acid can encode the heavy chain and J chain components of the secretory IgA antibody separated by a linking polypeptide (SEQ ID NO: 8).

With respect to the linking polypeptides of the presently-disclosed subject matter, the term "linking polypeptide" is used herein to describe a polypeptide that is capable of linking together or otherwise connecting (e.g., by covalent bonding) two polypeptides, but that is also capable of being cleaved to allow the two polypeptides connected by the linking polypeptide to separate from one another. For instance, in some embodiments of the presently-disclosed subject matter, the linking polypeptide includes an endoproteinase cleavage site or, in other words, an amino acid sequence within the linking polypeptide that is recognized and cleaved by an endoproteinase. In some embodiments, the linking polypeptide comprises a KP6 killer toxin propeptide sequence, such as in some embodiments, a KP6 killer toxin propeptide sequence selected from the sequences of SEQ ID NOS: 18-20. In some embodiments, the linking polypeptides can comprise sequences including one or two cleavage sites of proteases that are endogenous to the endomembrane system found in plants, including, but not limited to, proprotein convertases, such as furin-like endoproteases.

Still further provided, in some embodiments of the presently-disclosed subject matter, are isolated nucleic acid molecules. In some embodiments, isolated nucleic acid molecules are provided that comprise a nucleic acid sequence encoding a polypeptide that includes a heavy chain of an antibody, a light chain of an antibody, and a linking polypeptide connecting the heavy chain to the light chain on a single nucleic acid molecule. In this regard, in some embodiments, the isolated nucleic acid comprises a sequence selected from SEQ ID NOS: 1-4. In other embodiments, isolated nucleic acids are provided that comprise a nucleic acid sequence encoding a polypeptide that includes two or more components of a secretory IgA antibody (i.e., the heavy chain, light chain, J chain, or secretory component), such as, in some embodiments, the nucleic acid sequences provided in SEQ ID NO: 5-8.

The term "nucleic acid" is used herein to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated.

The term "isolated", when used in the context of an isolated nucleic acid molecule or an isolated polypeptide, is a nucleic acid molecule or polypeptide that, by the hand of man, exists apart from its native environment and is therefore not a product of nature. An isolated nucleic acid molecule or polypeptide can exist in a purified form or can exist in a non-native environment such as, for example, in a transgenic host cell The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer et al. (1991) *Nucleic Acid Res* 19:5081; Ohtsuka et al. (1985) *J Biol Chem* 260:2605 2608; Rossolini et al. (1994) *Mol Cell Probes* 8:91 98).

In some embodiments, an isolated nucleic acid sequence is provided that selectively hybridizes to the sequence of SEQ ID NOS: 1-8. The term "selectively hybridize" as used herein refers to the ability of a nucleic acid sequence to hybridize to a target polynucleotide (e.g., a polynucleotide of SEQ ID NOS: 1-8) with specificity. Thus, the nucleic acid sequence comprises a polynucleotide sequence that is complementary, or essentially complementary, to at least a portion of the target polynucleotide sequence. For example, in some embodiments, the nucleic acid sequence that selectively hybridizes to the sequence of SEQ ID NO: 1 is complementary to the sequence of SEQ ID NO: 1. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide. With regard to the nucleic acid sequences disclosed herein as selectively hybridizing to the sequences of SEQ ID NOS: 1-8, the hybridizing nucleic acid sequence need not necessarily be completely complementary to one of the nucleic acid of SEQ ID NOS: 1-8 along the entire length of the target polynucleotide so long as the hybridizing nucleic acid sequence can bind the nucleic acids of SEQ ID NOS: 1-8 with specificity. In some embodiments, the nucleic acid sequences that selectively hybridize to the sequences of SEQ ID NOS: 1-8 are about 80%, about 85%, about 90%, about 95%, about 98%, or about 100% complementary to the target sequence.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. For example, in some embodiments, nucleic acid hybridization can be performed at 60° C. with 0.1× sodium citrate-sodium chloride (SSC) and 0.1% sodium dodecyl sulfate (SDS). However, the combination of parameters is much more important than the measure of any single parameter. (See, e.g., Wetmur & Davidson, 1968). Determining appropriate hybridization conditions to identify and/or isolate sequences containing high levels of homology is well known in the art. (See, e.g., Sambrook, et al., 1989).

In some embodiments of the presently-disclosed subject matter, vectors that include one or more of the isolated nucleic acid sequences disclosed herein (e.g., the nucleic acid sequences of SEQ ID NOS: 1-8) are provided. The term "vector" is used herein to refer to any vehicle that is capable of transferring a nucleic acid sequence into another cell. For example, vectors which may be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art. In some embodiments, the vectors of the presently-disclosed subject matter are plasmids. In other embodiment of the presently-disclosed subject matter, the vectors of the presently-disclosed subject matter are viruses, such as a tobamoviruses (e.g., tobacco mosaic virus, turnip vein-clearing virus, tomato mosaic virus, etc.), cowpea mosaic virus, potato virus X, geminiviruses, among others, as such viruses have been found to be particularly useful for introducing a nucleic acid sequence of the presently-disclosed subject matter into a plant cell and for subsequently expressing the protein encoded by the nucleic acid in the plant cell.

In some embodiments, the nucleic acids of the presently-disclosed subject matter are operably linked to an expression cassette. The terms "associated with", "operably linked", and "operatively linked" refer to two sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

The presently-disclosed subject matter also provides transgenic plant cells or plants that have been transformed with one or more of the vectors disclosed herein. In some embodiments, a plant cell, or a progeny of the plant cell, is provided wherein the plant cell and/or its progeny is transfected with a vector of the presently-disclosed subject matter such that the cell and/or its progeny expresses the polypeptide.

As used herein, the term "plant cell" is understood to mean any cell derived from a monocotyledonous or a dicotyledonous plant and capable of constituting undifferentiated tissues such as calli, differentiated tissues such as embryos, portions of monocotyledonous plants, monocotyledonous plants or seed. The term "plant" is understood to mean any differentiated multi-cellular organism capable of photosynthesis, including monocotyledons and dicotyledons. In some embodiments, the plant cell is a *Nicotiana* or flowering tobacco plant cell, such as a *Nicotiana benthamiana* plant cell that has been transformed with a vector of the presently-disclosed subject matter.

The terms "transformed," "transgenic," and "recombinant" are used herein to refer to a cell of a host organism, such as a plant, into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof.

The terms "heterologous," "recombinant," and "exogenous," when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

Introduction of a nucleic acid (e.g., a nucleic acid incorporated into an appropriate vector) into a plant cell in accordance with the presently-disclosed subject matter can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a nucleic acid sequence or gene of interest can be performed by agro-infiltration methods. In this regard, a suspension of *Agrobacterium tumefaciens* containing a nucleic acid sequence or gene of interest can be grown in culture and then vacuum-infiltrated into a plant. Once inside the tissues of the plant (e.g., the leaves of the plant), the *Agrobacterium* transforms the gene of interest to a portion of the plant cells where the gene is then transiently expressed. For additional information and guidance regarding the expression of a nucleic acid sequence of interest in a plant cell, see, e.g., Matoba N, et al. Methods Mol Biol. 2011; 701:199-219; and, Matoba N, et al. PLoS One. 2010 Jun. 15; 5(6):e11143, each of which are incorporated herein by this reference.

As another example, transformation of a plasmid or nucleic acid of interest into a plant cell can be performed by particle gun bombardment techniques. In this regard, a suspension of plant embryos can be grown in liquid culture and then bombarded with plasmids or nucleic acids that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

For additional guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486,234; 539,563; 674,725; and, International Patent Application Publication Nos. WO 91/02071 and WO 95/06128, each of which is incorporated herein by this reference.

In still further embodiments of the presently-disclosed subject matter are antibodies produced by the methods described herein. In some embodiments, the antibodies can be used as part of a therapeutic or diagnostic method whereby the antibodies are used to diagnose and/or treat diseases and disorders including, but not limited to, cancer and inflammatory disorders. In some embodiments, the antibodies can be used as part of a therapeutic method whereby the antibodies are administered to a subject, alone or in combination with other antiviral agents, to treat a viral infection. In some embodiments, a method of treating a viral infection is provided that includes the steps of obtaining a neutralizing antibody produced by the methods of the presently-disclosed subject matter, and administering an effective amount of the antibody to a subject.

As used herein, the terms "treatment" or "treating" relate to any treatment of an infection of a subject by a virus, including, but not limited to, prophylactic treatment and therapeutic treatment. As such, the terms treatment or treating include, but are not limited to: preventing a viral infection or the development of a viral infection; inhibiting the progression of a viral infection; arresting or preventing the development of a viral infection; reducing the severity of a viral infection; ameliorating or relieving symptoms associated with a viral infection; and causing a regression of the viral infection or one or more of the symptoms associated with the viral infection.

The term "neutralizing antibody" is used herein to refer to antibodies that defend a cell or tissue of a subject from an antigen, such as a virus of other infectious body, by inhibiting or neutralizing the biological effect of the antigen, as opposed to binding to the antigen to thereby mark the antigen for further processing and destruction. In some embodiments, the neutralizing antibody is selected from an anti-HIV VRC01 antibody, an anti-HIV PGT121 antibody, and an anti-influenza CR6261 antibody. Of course, numerous other types of neutralizing antibodies can also be produced and used including, but not limited to, antibodies against the hepatitis C virus (e.g., HCV1), antibodies against avian and human pandemic influenza viruses (e.g., 65C6, PN-SIA28, 10F7), SARS coronavirus (e.g., CR3014, CR3022, SK4), ebola virus (e.g., 13C6, 13F6, 6D8) west nile virus (e.g., Hu-E16), respiratory syncytial virus (e.g., palivizumab), and herpes simplex virus (e.g., HSV8). Such antibodies can readily be produced by the methods of the presently-disclosed subject matter and then administered to a subject to treat a viral infection without departing from the spirit and scope of the subject matter described herein.

In some embodiments of the presently-disclosed subject matter, the neutralizing antibodies produced by the above-described methods can also be administered with one or more additional antiviral agents that are capable of treating a viral infection as defined herein. Antiviral agents that are useful in this regard include, but are not limited to, protease inhibitors, antiviral lectins, integrase inhibitors, nucleoside reverse transcriptase inhibitors, non-nucleoside reverse transcriptase inhibitors, and nucleotide/nucleoside analogs, with specific examples of such antiviral agents including cyanovirin-N, actinohivin, zidovudine, tenofovir, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the alpha-interferon, beta-interferon, adefovir, clevadine, entecavir, and pleconaril. In some embodiments, the further antiviral agent is selected from the antiviral lectin griffithsin, the CCR5 antagonist maraviroc (MVC), and the reverse transcriptase inhibitor tenofovir as the use of such additional antiviral agents have shown synergy when administered with the antibodies produced by methods described herein.

For administration of a therapeutic composition as disclosed herein (e.g., a composition comprising an antibody produced by the presently-described methods), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

Suitable methods for administering a therapeutic composition in accordance with the methods of the presently-disclosed subject matter include, but are not limited to, systemic administration, parenteral administration (including intravascular, intramuscular, intraarterial administration), oral delivery, topical administration, buccal delivery, rectal delivery, vaginal delivery, subcutaneous administration, intraperitoneal administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180, 082). In some embodiments, administering the antibodies produced in accordance with the presently-disclosed subject matter comprises topically or vaginally administering the antibodies as a means to reduce the infectivity of a virus.

Regardless of the route of administration, the compounds of the presently-disclosed subject matter are typically administered in an amount effective to achieve the desired response. As used herein, the terms "effective amount" and "therapeutically effective amount" refer to an amount of the therapeutic composition (e.g., a composition comprising an antibody produced by the presently-described methods) sufficient to produce a measurable biological response (e.g., a reduction in viral infectivity). Actual dosage levels of active ingredients in a therapeutic composition of the presently-disclosed subject matter can be varied so as to administer an amount of the active antibodies(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, N.J.; Goodman, et al., (2006) Goodman & Gilman's the Pharmacological Basis of Therapeutics, 11th ed. McGraw-Hill Health Professions Division, New York; Ebadi. (1998) CRC Desk Reference of Clinical Pharmacology. CRC Press, Boca Raton, Fla.; Katzung, (2007) Basic & Clinical Pharmacology, 10th ed. Lange Medical Books/McGraw-Hill Medical Pub. Division, New York; Remington, et al., (1990) Remington's Pharmaceutical Sciences, 18th ed. Mack Pub. Co., Easton, Pa.; Speight, et al., (1997) Avery's Drug Treatment: A Guide to the Properties, Choice, Therapeutic Use and Economic Value of Drugs in Disease Management, 4th ed. Adis International, Auckland/Philadelphia; and Duch, et al., (1998) Toxicol. Lett. 100-101:255-263, each of which are incorporated herein by reference.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immortalized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. Some of the following examples are prophetic, notwithstanding the numerical values, results and/or data referred to and contained in the examples. The following examples may also include compilations of data that are representative of data gathered at various times during the course of development and experimentation related to the present invention.

EXAMPLES

Materials and Methods for Examples 1-3

Vector Construction and Expression in *N. benthamiana*.

For the expression of VRC01, a deconstructed one-component magnICON® tobamoviral vector (pICH38099; ICON Genetics GmbH, Halle/Saale, Germany) was used. An *N. benthamiana* codon-optimized DNA sequence for VRC01 was synthesized based on amino acid sequence information available at Protein Data Bank (PDB; 3NGB). The H and L chains of the IgG1 MAbs were joined by the KP6 killer toxin propeptide sequence (KP6pp; UniProtKB/Swiss-Prot: P16948, amino acid 106-138) flanked by a Gly-Gly sequence at both N- and C-termini. The vectors were delivered into *N. benthamiana* leaves using the *Agrobacterium* vacuum infiltration method, as described previously (see Marillonnet, et al. Nat. Biotechnol. 23:718-723; see also Matoba, et al. PLoS ONE 5:e11143), using a bacterial density ($OD_{600}$) in the infiltration buffer of 0.03.

MAb Purification.

Five to seven days post infiltration (dpi), leaf material was homogenized by a Waring blender in ice cold extraction buffer (100 mM Phosphate, pH 6.0, 100 mM NaCl, 40 mM ascorbic acid) and the extract was filtered through cheese cloth and miracloth followed by centrifugation at 15,000×g for 15 min at 4° C. The clarified extract was adjusted to pH 7.0 with sodium hydroxide, centrifuged at 15,000×g for 15 min at 4° C., and filtered through a 0.22 μm filter. The VRC01 proteins were purified using the following procedure under ice cold conditions. Chromatography was performed using an AKTA Purifier (GE Healthcare). A GE Healthcare High Trap Protein A HP 5 ml pre-packed column was equilibrated with 10 column volumes (CV) of buffer A (20 mM Phosphate, pH 7.0). Samples were loaded at 2.0 ml/min. The column was washed with 10 CV of buffer A. The VRC01 proteins were eluted with a step gradient using 100% buffer B (0.1 M Glycine, 0.2 M L-Arginine, pH 3.0) and collected by monitoring absorbance at 280 nm. Immediately, the fraction containing the peak at 280 nm was adjusted to pH 7.0 using cold Tris, pH 9.0 buffer. SDS-PAGE was employed to assess the collected fractions for the presence of VRC01. The VRC01-containing fractions were further purified using a GE Healthcare HiTrap Phenyl HP 5 ml pre-packed column. The column was equilibrated with 10 CV of Phenyl buffer A (50 mM Phosphate, pH 7.0, 1 M Ammonium Sulfate) and the samples (Protein A purified VRC01 diluted 1:10 in Phenyl buffer A) were loaded at a flow rate of 2.5 ml/min followed by a 10 CV wash with Phenyl buffer A. Proteins were eluted using a gradient from 0 to 100% Phenyl buffer B (50 mM Phosphate, pH 7.0) over 30 CV. Five ml fractions were collected and the VRC01-containing fractions, after verification by SDS-PAGE, were combined, and ultrafiltrated and diafiltrated into sterile Dulbecco's PBS (DPBS) (Gibco) using Amicon Ultra-15 30,000 MWCO centrifugal devices (Millipore) according to the manufacturer's instructions. The concentration of the formulated VRC01 was determined using theoretical extinction coefficients at 280 nm of 1.5381 $(mg/ml)^{-1}$ $cm^{-1}$. Finally, the purified VRC01 was aliquoted, flash frozen, and stored at −80° C. until use.

Binding Analysis.

Enzyme-linked immunosorbent assay (ELISA) and surface plasmon resonance (SPR) were used to analyze the binding of bnMAbs. For ELISA, a 96-well plate was coated with 1 μg/mL gp120 (Immune Technology Corp, New York, N.Y.) in coating buffer (15 mM $Na_2CO_3$, 35 mM $NaHCO_3$, pH 9.6) by incubating at 37° C. for 1 h. Plates were blocked with 5% PBSTM (phosphate-buffered saline, pH 7.4, 0.05% [v/v] Tween-20, 5% non-fat dry milk) for 1 h at room temperature. Clarified leaf extracts or a VRC01 standard (1 μg/ml to 0.00137 μg/ml), serially diluted 3-fold in 1% PBSTM, were incubated for 1 h at 37° C. The plate-bound VRC01 was detected by a mouse anti-human IgG (Fc) horseradish peroxidase (HRP)-conjugated secondary Ab (SouthernBiotech) diluted 1:5,000 in 1% PBSTM and a chemiluminescence substrate (TMB Super Sensitive HRP Substrate, BioFX Laboratories). Plates were incubated with the secondary antibody for 1 h at 37° C. The reaction was stopped with stop solution (0.6 N $H_2SO_4$, 1N HCl). The optical density at 450 nm ($OD_{450}$) was read on a Beckman Coulter DTX880 Multimode Detector. A standard curve was generated, which was used to estimate the VRC01 concentrations in the clarified extracts. For SPR, the binding affinity ($K_D$) of gp120 to VRC01 was measured using a Biacore X100 2.0 instrument at ambient temperature. Briefly, monoclonal mouse anti-human IgG (Fc) antibody of IgG1 isotype (25 μg/ml) was immobilized on a CM5 sensor chip (GE Healthcare Biosciences) to 10,000 resonance units (RU) using the human antibody capture kit (GE Healthcare Biosciences). A reference flow cell was immobilized with the antibody to correct response contributions such as bulk shifts that occur equally in the sample and reference flow cells. VRC01 was captured on the anti-human IgG (Fc) chip to a surface density of about 200 RU. Serial dilutions of gp120 (50 μg/ml to 0.616 μg/ml) were made in running buffer (HPS-EP, GE Healthcare Biosciences) and injected, at a flow rate of 5 μl/min, for a contact time of 120 s and a dissociation time of 1800 s. A blank cycle (running buffer) was performed and all sample injections were blank subtracted to correct the sensorgrams for drifts and other disturbances that affect the reference subtracted curve. Between sample injections the system was washed with running buffer and the immobilized surface was regenerated with the human antibody capture kit regeneration solution. A replicate of a non-zero concentration of gp120 and the blank were injected in each experiment for double referencing thus verifying the reliability of immobilized chip throughout the experiment. The data were analyzed using the 1:1 Binding Model analysis with parameter settings of $R_{max}$=local and RI set to zero in the Biacore X100 2.0 evaluation software.

Peptide Mapping.

Peptide mapping was performed on purified VRC01p. VRC01p was separated into L and H chains by reducing SDS-PAGE. The L and H chain gel bands were excised and sent to the Columbia University Medical Center Protein Core Facility for Matrix-assisted laser desorption/ionization time-of-flight mass spectrometry (MALDI-TOF-MS) analysis. The L chain was digested with endoproteinase Lys-C and the H chain was digested with trypsin. Angiotensin was used as an internal standard and the spectra show the MH+ peak for each peptide HIV-1 Pseudovirus Production.

The pseudoviruses were produced in 293T/17 cells essentially as described before, using an env-expressing plasmid and an env-deficient HIV-1 backbone vector (pSG3ΔEnv or pNL4.3ΔEnv-Luc) (see Montefiori, et al. Methods Mol. Biol. 485: 395-405; see also Zhang, et al. J. Virol. 73: 5225-5230). Envs used in this study included CCR5-tropic strains from the clades A, B and C: Q769.h5, SS1196.1, SF162, Du156, and ZM214M.PL15. All five Env-expressing plasmids were obtained from the NIH AIDS Reagent Program (catalog numbers 11884, 11020, 10463, 11306, and 11310, respectively). Pseudovirus-containing culture supernatants were harvested two days after transfection, filtered (0.45 μm), and stored at −80° C. in 1 ml aliquots. The optimal viral input (taken as the dilution that yielded greater than or equal to 150,000 relative light units (RLU) and greater than 10 times the average RLU of cell-only background levels, as recommended in a standardized protocol of a single thawed aliquot of each batch of pseudovirus was determined in TZM-b1 or HOS-CD4-CCR5$^+$ cells. Serial dilutions in a total volume of 200 μl of growth medium were performed in triplicate wells of both a clear and black solid, flat-bottom, 96-well culture plates for a total of 8 dilution steps. Pseudovirus was omitted from the last column of the 96-well plate (cell control). Freshly trypsinized cells (10,000 cells in 100 μl of growth medium containing 10 μg/ml DEAE-dextran) were added to each well. The plates were incubated at 37° C. in a humidified 5% $CO_2$/95% air environment. After a 48 h incubation, 100 μl of culture medium was removed from each well and 100 μl of Bright Glo reagent (Promega Corp.) was added to the cells. After a 2 min incubation at room temperature, luminescence was measured using the Synergy HT luminometer.

HIV-1 Neutralization Assay.

Reporter gene expression Env-pseudotyped virus infectivity assays were used to measure HIV-1-neutralization capacity of anti-HIV compounds. Neutralization was measured as a reduction in firefly luciferase (Luc) reporter gene expression in the presence of test sample compared to the absence of sample after a single round of infection in TZM-b1 or HOS-CD4-CCR5$^+$ cells. Briefly, the optimal viral input of each pseudovirus was incubated with various concentrations of test samples (eight dilutions, threefold stepwise) in triplicate for 1.5 h at 37° C. in a total volume of 100 μl growth medium in 96-well black solid flat-bottom culture plates (Corning-Costar). Freshly trypsinized cells (10,000 cells in 100 μl of growth medium containing 10 μg/ml DEAE-dextran) were added to each well. One set of eight control wells received cells plus virus (virus control), and another set of eight wells received cells only (background control). After a 48 h incubation, 100 μl of culture medium was removed from each well and 100 μl of Bright Glo reagent (Promega Corp.) was added to the cells. After a 2 min incubation at room temperature, luminescence was measured using the Synergy HT luminometer. The 50% inhibitory concentration ($IC_{50}$) was defined as the sample concentration that caused a 50% reduction in RLU compared to virus control wells after subtraction of background RLU. $IC_{50}$ was determined using the dose response inhibition—variable slope fit in GraphPad Prism software.

For anti-HIV-1 synergy analysis, combination indices (CI) were calculated using CalcuSyn software (Biosoft) based on the median effect principle of Chou and Talalay. A CI-value of less than 0.9, 0.9-1.1, and greater than 1.1 indicate synergism, additive effects, and antagonism, respectively. Synergism was analyzed for the combinations of VRC01p and each of the following three anti-HIV agents; GRFT, MVC, and TFV.

Example 1—Full-Length IgG Molecules were Produced from a Single Tobamoviral Replicon Transgene in *N. benthamiana*

Figure 1B:
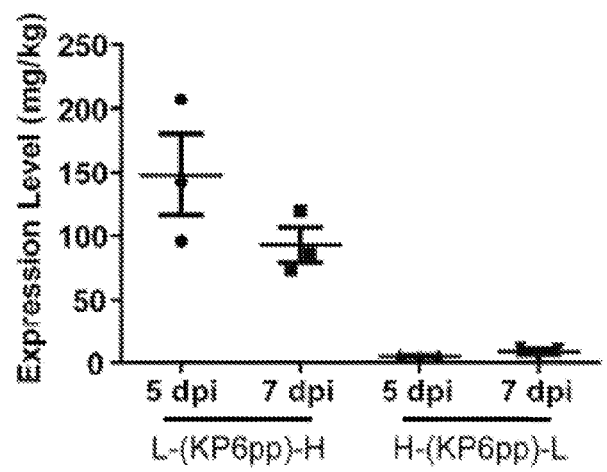
Figure 1C:
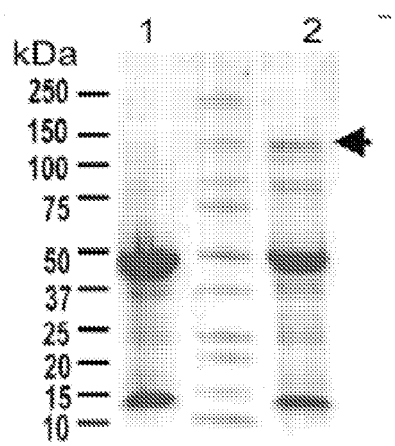

Conventional IgG production in plants relies on expression of H and L chains from two independent transcription units. To develop a simple yet robust production platform, the subtilisin-like processing protease kex2p and a tobamoviral replicon vector was used in a manner whereby H and L chains were simultaneously and rapidly overexpressed from a single polypeptide transgene. The KP6pp sequence, a 33-amino-acid peptide containing two kex2p recognition sites at N- and C-termini, was incorporated between H and L chains to create two constructs, i.e., L-(KP6pp)-H and H-(KP6pp)-L (FIG. 1A). At 5 to 7 dpi, these two constructs were compared for the amount of functional bnMAbs accumulated in leaves using gp120-capture ELISA. As shown in FIG. 1B, the L-(KP6pp)-H construct expressed significantly higher levels of VRC01 than the H-(KP6pp)-L construct, yielding up to 150 mg of the bnMAb per kg of fresh leaf material in a representative 3-plant production batch. The optimal timing of harvest to obtain a maximal yield varied between batch to batch within 5 to 7 dpi, likely reflecting fluctuation in plant growth and/or agroinfiltration conditions (data not shown). An SDS-PAGE analysis of crude extract of the L-(KP6pp)-H construct-expressing, but not uninfiltrated control leaves, showed a distinct band at around 150 kDa, the expected size of assembled MAb (FIG. 1C). Immunoblot analysis under reducing conditions using anti-human IgG Abs revealed that the protein was composed of two polypeptides with molecular sizes of approximately 50 kDa and approximately 25 kDa, which indicated cleavage at the KP6pp sequence and assembly of full-length, $H_2L_2$ form of IgG (data not shown). Immunoblot analysis under non-reducing conditions revealed that full-length IgG was the most prominent product, but there was another major band with a molecular size of approximately 100 kDa. This band, which was also present in a human IgG isotype control, may represent $H_2L_1$ or Fab-Fc byproduct as it was detected by both anti-Fc and anti-kappa L chain Abs (data not shown).

Figure 1D:
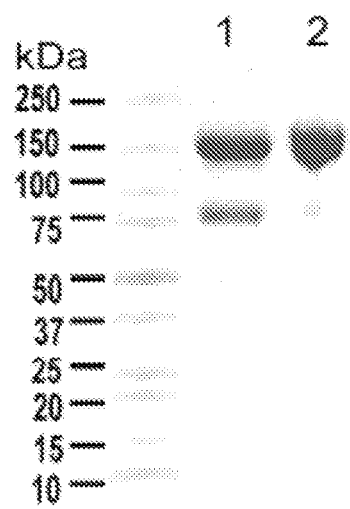
Figure 2:
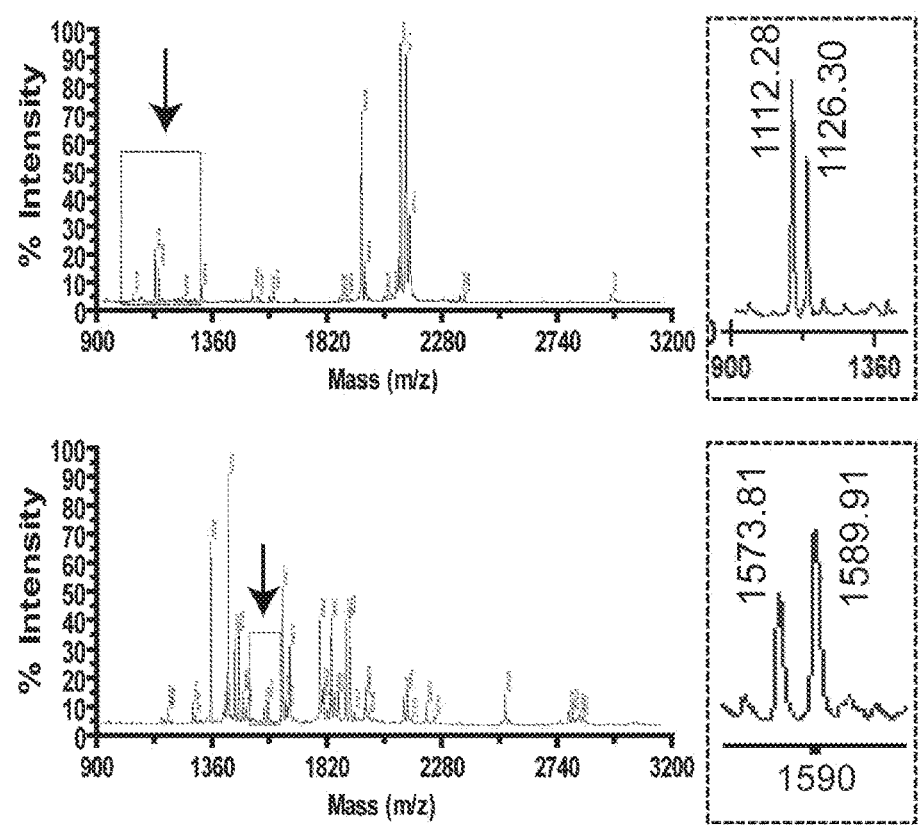
FIG. 2 includes graphs showing peptide mapping of VRC01p L and H chains based on matrix-assisted laser desorption/ionization time-of-flight mass spectrometry (MALDI-TOF-MS), where the upper graph shows the L chain digested with endoproteinase Lys-C with the ions (peaks) in the spectra of singly charged species ([M+H]$^+$; magnified in the right panel) containing mass-to-charge-ratios (m/z) of 1112.28 and 1126.30 that correspond well to the theoretical mass values of the L chain C-terminal peptide with cysteine modification by iodoacetamide upon sample preparation for MS analysis (1112.28) and acrylamide from the SDS-PAGE analysis (1126.30), where the lower graphs shows the H chain digested with trypsin with the ions (peaks) in the spectra of singly charged species ([M+H]$^+$; magnified in the right panel) containing m/z of 1573.81 and 1589.91 that correspond well to the theoretical mass values of the H chain N-terminal peptide (1573.81) and its Met-oxidized form (1589.91), and where, taken together, these results verify cleavage between the Lys and Arg at the two kex2p recognition sites resulting in separate light and heavy chains for antibody assembly.

The *Nicotiana* plant-expressed VRC01 from the L-(KP6pp)-H construct (hereafter designated VRC01p) was efficiently purified using Protein A followed by Phenyl HP hydrophobic interaction resins. The purity was determined to be greater than 98% based on a densitometric analysis of a Coomassie-stained SDS-PAGE gel resolved under non-reducing conditions (FIG. 1D, lane 2). The $H_2L_1$ or Fab-Fc byproduct was present after Protein A purification, but successfully removed upon the subsequent Phenyl HP step. The yield of the final product was roughly 50%. Sequence mapping based on MALDI-TOF-MS showed the processing of KP6pp by a kex2p-like protease as expected, with cleavage between Lys-Arg at both N- and C-termini of the peptide region (FIG. 2).

Example 2—VRC01p IgG Holds an Intact Gp120-Binding Affinity and HIV-1 Neutralization Activity To assess the integrity of VRC01p, the MAb's capacity to bind gp120 was evaluated. In an ELISA using recombinant gp120 from Q769.H5 (clade A), SF162 (clade B), and DU156 (clade C) strains, VRC01p and the HEK293F cell-produced bnMAb (VRC01$_{HEK}$) showed closely overlapping binding curves (FIG. 3A). Consistent with that, surface plasmon resonance (SPR) analysis (FIG. 3B) showed that those plant- and human cell-produced bnMAbs have similar binding affinities to gp120$_{SF162}$, with K$_D$ values being 3.97±0.74 nM (VRC01p) and 3.82±0.60 nM (VRC01$_{HEK}$). No statistical difference was found (unpaired Student's t-test). Taken together, these results demonstrated that the IgG1 bnMAb VRC01p produced in Nicotiana using the single polypeptide system described here retains full gp120-binding capacity.

Figure 3C:
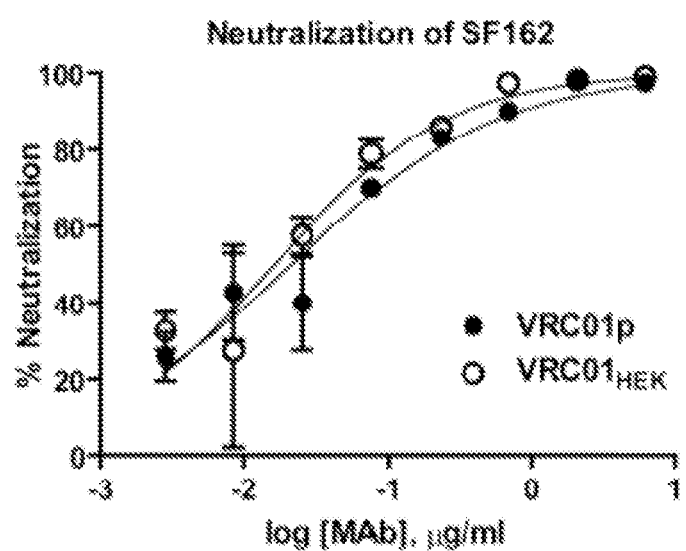

Next, the anti-HIV-1 effects of VRC01p and VRC01$_{HEK}$ were compared in an HIV-1 neutralization assay. As shown in FIG. 3C, the two bnMAbs showed very similar neutralization dose curves against CCR5-using B clade SF162 virus. Average IC$_{50}$ values of VRC01p and VRC01$_{HEK}$ from three independent experiments were 41.1±17.1 ng/ml and 23.1±5.5 ng/ml, respectively, and therefore not significantly different (P=0.37, unpaired Student's t-test). Moreover, VRC01p's HIV-1 neutralization IC$_{50}$s were determined for 4 additional viruses (Table 1), showing similar values to those reported for VRC01$_{HEK}$.

TABLE 1

Comparison of VRC01p vs. VRC01$_{HEK}$ IC$_{50}$ Values.

| Virus | VRC01p IC$_{50}$ (μg/ml)$^a$ | VRC01$_{HEK}$ IC$_{50}$ (μg/ml)$^b$ |
|---|---|---|
| Q769.h5 | 0.17 ± 0.04 | 0.084 |
| SF162 | 0.04 ± 0.02 | 0.139 |
| SS1196.1 | 1.32 ± 0.01 | NR$^c$ |
| Du156 | 0.14 ± 0.03 | 0.089 |
| ZM214M.PL15 | 1.21 ± 0.16 | 0.44 |

$^a$Data are expressed as mean ± SEM of three independent experiments.
$^b$Reported by Wu et al. (16).
$^c$NR represents not reported Taken together, the above data demonstrated that VRC01p holds gp120-binding capacity and HIV-1 neutralization activities that are virtually identical to the human cell-derived bnMAb.

Example 3—VRC01p Synergizes with the Antiviral Lectin GRFT, the CCR5 Antagonist MVC, and the RT Inhibitor TFV To derive the microbicide combination potential of VRC01p, the HIV-1 neutralization activity was analyzed in combination with three representative microbicide candidates holding distinct antiviral actions. GRFT is a potent antiviral lectin specific to high-mannose-type glycans and categorized as an entry inhibitor. The protein has been shown to neutralize a broad spectrum of HIV strains at picomolar concentrations with no discernible toxicity or inflammatory responses in cervicovaginal cells and tissues. MVC is a small-molecule entry inhibitor that blocks the viral interaction with the chemokine receptor CCR5 and has been used as an ARV to treat HIV-1 infected individuals. Vaginal administration of MVC has been recently shown to provide protection in macaque and humanized mouse challenge models. MVC and dapivirine-MVC combination vaginal rings are being evaluated in a Phase I safety trial (MTN-013/IPM 026). The nucleotide analogue RT inhibitor TFV showed modest efficacy in a Phase IIb efficacy trial upon a peri-coital use as a gel product.

Figure 4:
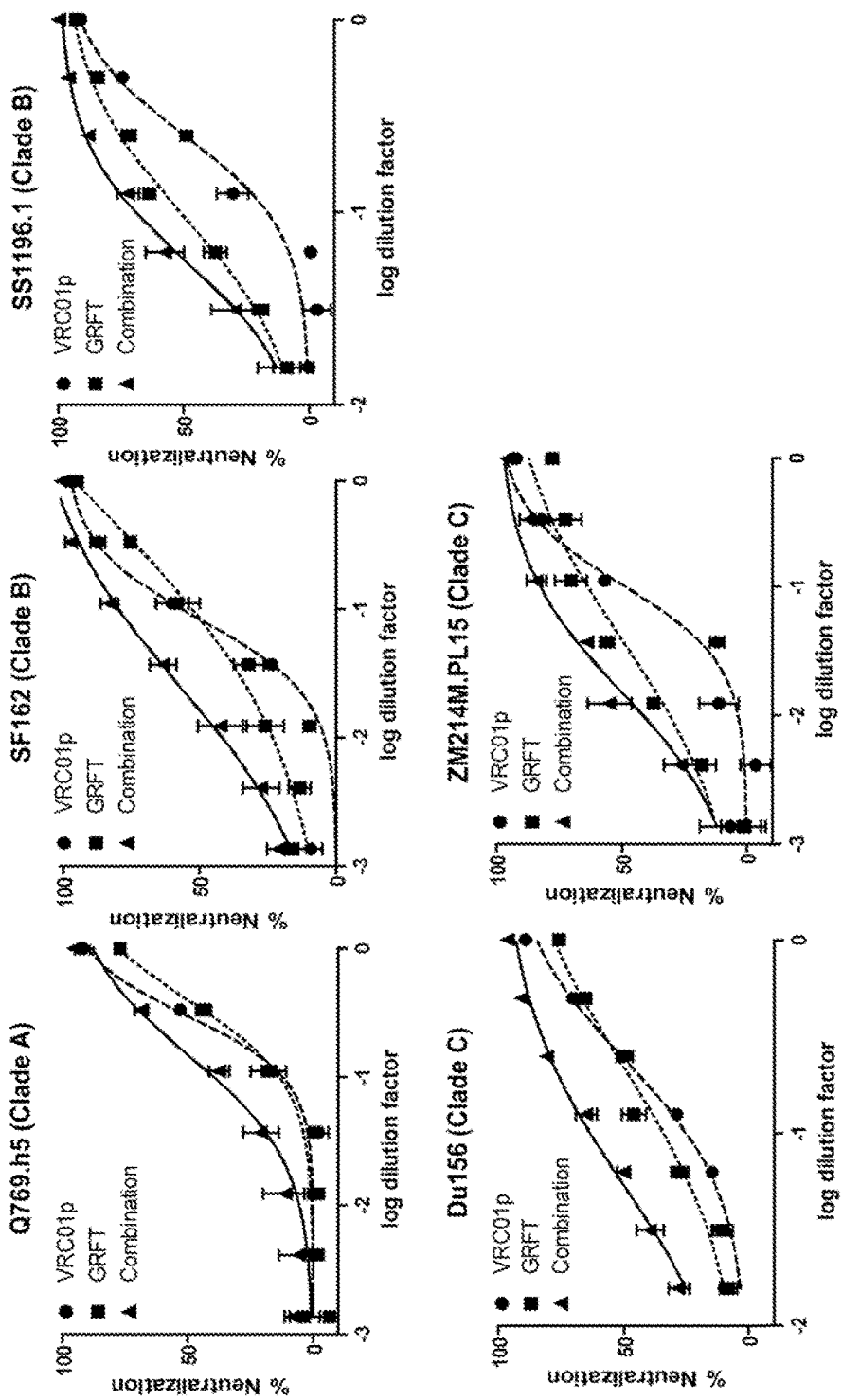
FIG. 4 includes graphs showing HIV-1 neutralization by VRC01p, GRFT, and a VRC01p-GRFT combination, where the A clade Q769.h5, B clades SF162 and SS1196.1, and C clades Du156 and ZM214M.PL15 pseudoviruses were used with starting concentrations for each neutralizing agent of 2 µg/ml (or 13.3 nM; Q769.h5), 20 µg/ml (or 133.3 nM; SF162), 10.54 µg/ml (or 70.3 nM; SS1196.1), 1.08 µg/ml (or 7.2 nM; Du156), and 1.54 µg/ml (or 10.3 nM; ZM214M.PL15) for VRC01; and 16.4 nM (Q769.h5), 20 nM (SF162), 0.244 nM (SS1196.1), 0.096 nM (Du156) and 20 nM (ZM214M.PL15) for GRFT, and where the effect of the combination of VRC01p and GRFT against each virus was tested by dilution of the two agents starting at a fixed 1:1 ratio proportional to their IC$_{50}$s.
Figure 5:
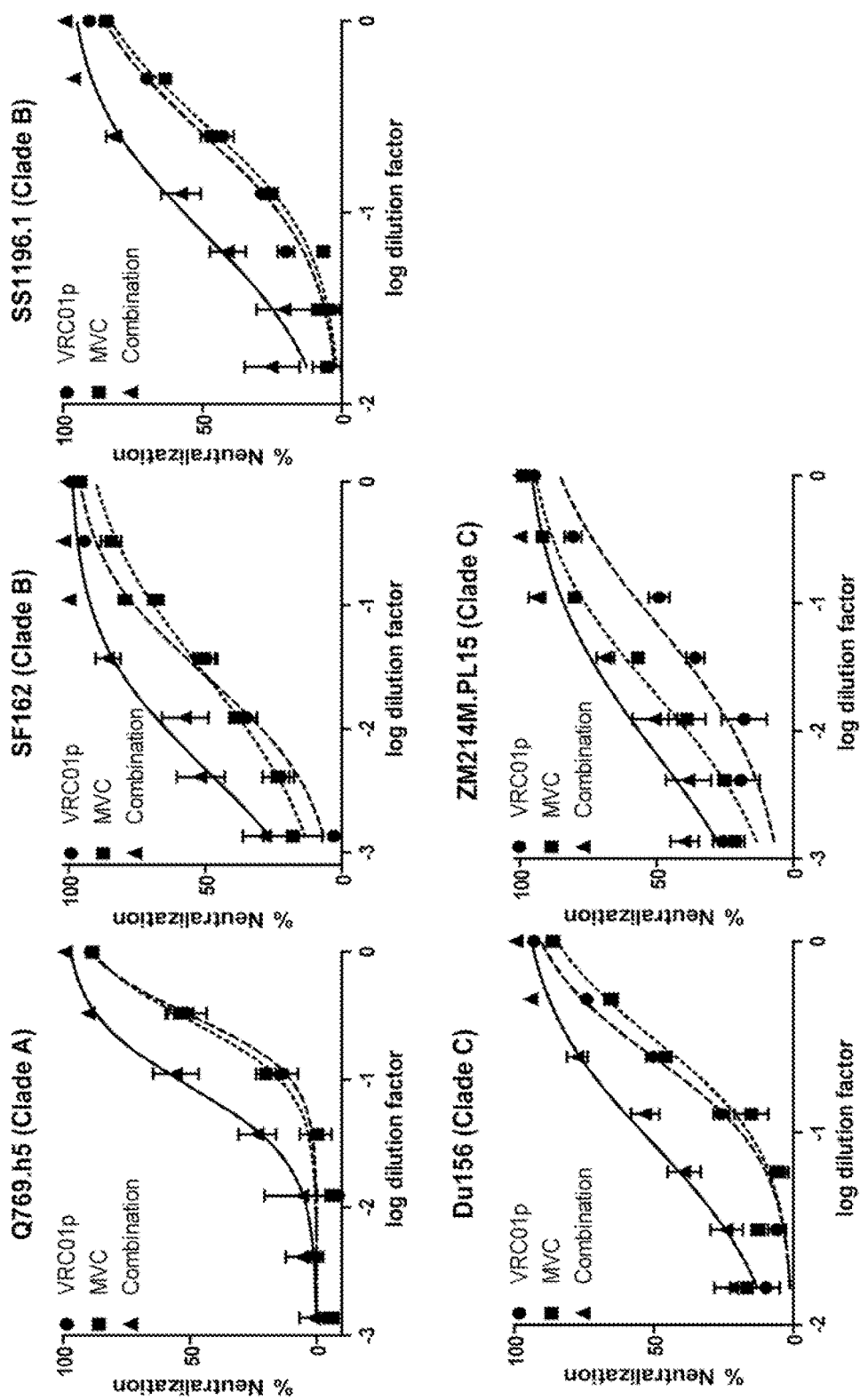
FIG. 5 includes graphs showing HIV-1 neutralization by VRC01p, MVC, and a VRC01p-MVC combination, where the A clade Q769.h5, B clades SF162 and SS1196.1, and C clades Du156 and ZM214M.PL15 pseudoviruses were used with starting concentration for each neutralizing agent of 2 µg/ml (or 13.3 nM; Q769.h5), 20 µg/ml (or 133.3 nM; SF162), 10.54 µg/ml (or 70.3 nM; SS1196.1), 1.08 µg/ml (or 7.2 nM; Du156), and 1.54 µg/ml (or 10.3 nM; ZM214M.PL15) for VRC01; and 0.2 µM (Q769.h5), 1 µM (SF162), 0.544 µM (SS1196.1), 0.588 µM (Du156), and 0.5 µM (ZM214M.PL15) for MVC, and where the effect of the combination of VRC01p and MVC against each virus was tested by dilution of the two agents starting at a fixed 1:1 ratio proportional to their IC$_{50}$s.
Figure 6:
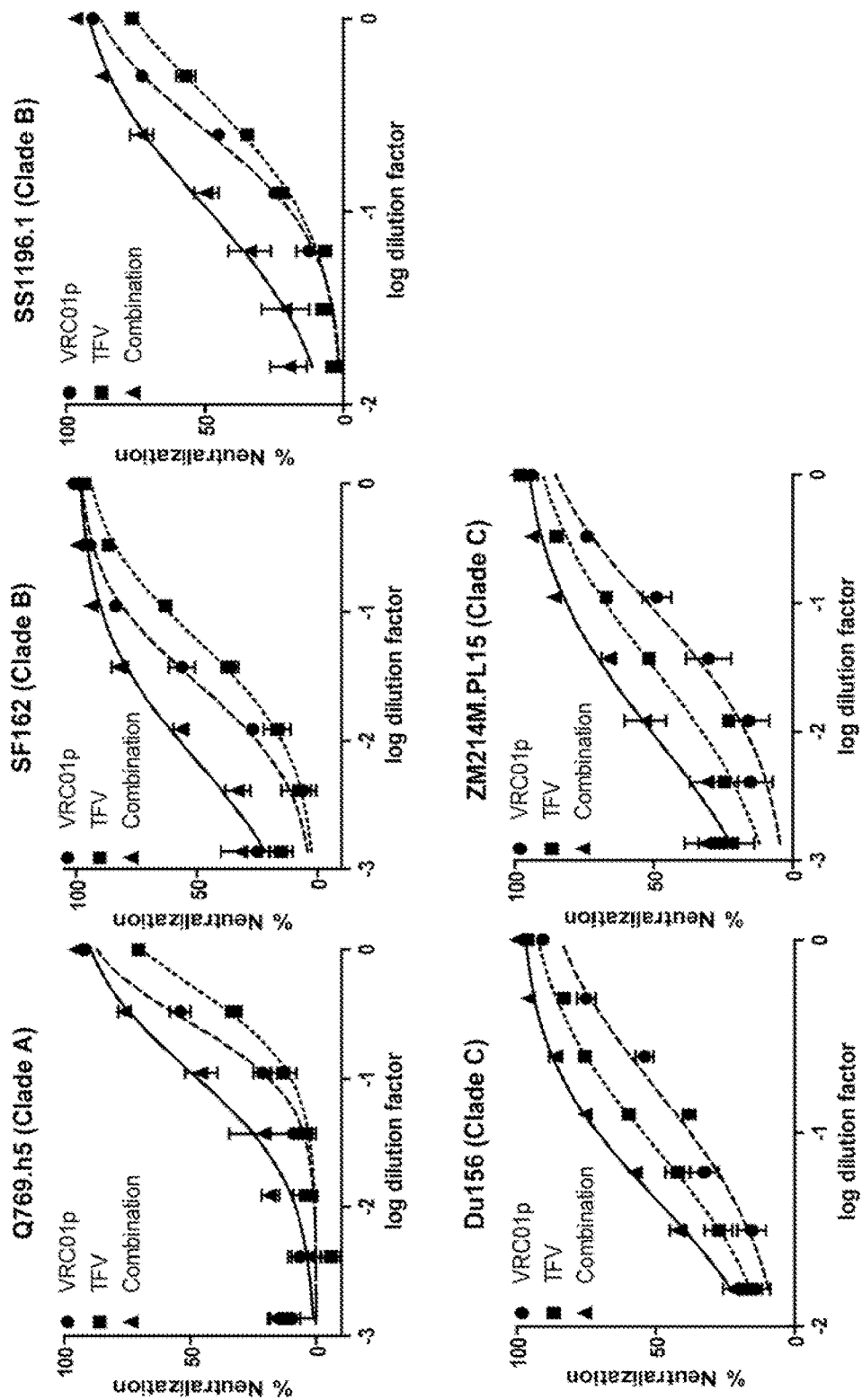
FIG. 6 is a graph showing HIV-1 neutralization by VRC01p, TFV, and VRC01p-TFV combination, where the A clade Q769.h5, B clades SF162 and SS1196.1, and C clades Du156 and ZM214M.PL15 pseudoviruses were used with starting concentrations for each neutralizing agent of 2 µg/ml (or 13.3 nM; Q769.h5), 20 µg/ml (or 133.3 nM; SF162), 10.54 µg/ml (or 70.3 nM; SS1196.1), 1.08 µg/ml (or 7.2 nM; Du156), and 1.54 µg/ml (or 10.3 nM; ZM214M.PL15) for VRC01; and 30 µM (Q769.h5), 100 µM (SF162) 27.2 µM (SS1196.1), 41.6 µM (Du156), and 100 µM (ZM214M.PL15) for TFV, and where the effect of the combination of VRC01p and TFV against each virus was tested by dilution of the two agents starting at a fixed 1:1 ratio proportional to their IC$_{50}$s.

In these assays, each chosen combination of inhibitors was diluted as a mixture so as to maintain a constant ratio between them, allowing subsequent analysis of synergy. In order to rule out that the inhibiting effects of the given combinations weren't specific to a particular HIV-1 strain, at least one strain was chosen from HIV-1 clades A, B, and C together representing the majority of HIV-1 strains found worldwide. First, the IC$_{50}$ of VRC01p, GRFT, MVC, and TFV alone was determined, followed by the two-drug combination VRC01p/GRFT, VRC01p/MVC, and VRC01p/TFV against each HIV-1 clade tested. Upon analysis of the results, it was found that VRC01p synergizes with GRFT, MVC, and TFV against each HIV-1 pseudovirus tested using TZM-b1 target cells. As shown in FIGS. 4-6, VRC01p/GRFT, VRC01p/MVC, and VRC01p/TFV combinations resulted in a more efficient neutralization profile against each virus tested. A summary of the synergy analysis is presented in Table 2, with the IC$_{50}$ concentrations for VRC01p alone or in combination with the other inhibitors shown in Table 3 and the IC$_{50}$ concentrations of each inhibitor alone and in combination with VRC01p shown in Table 4. CI values were determined to evaluate the type of drug—drug interactions. The obtained CI values varied between 0.13 and 0.68, resulting thus in clear synergism at the calculated IC$_{50}$, IC$_{75}$, and IC$_{90}$ level for each combination. Strong synergism (CI<0.3) was observed for VRC01p-GRFT in SF162 at the IC$_{90}$ level, VRC01p-MVC in SS1196.1 at the IC$_{90}$ level, and VRC01p-MVC in ZM214M.PL15 at IC$_{75}$ and IC$_{90}$ levels. Overall, combinations of VRC01p with GRFT and MVC showed better synergism at all inhibitory levels than those of VRC01p and TFV.

TABLE 2

Combination index (CI) values for VRC01p in combination with other inhibitors.

| | CI | | |
|---|---|---|---|
| Inhibitors | 50% | 75% | 90% |
| Q769.h5 | | | |
| VRC01p:GRFT | 0.38 ± 0.06 | 0.41 ± 0.10 | 0.56 ± 0.22 |
| VRC01p:MVC | 0.38 ± 0.09 | 0.33 ± 0.05 | 0.39 ± 0.13 |
| VRC01p:TFV | 0.47 ± 0.06 | 0.56 ± 0.11 | 0.68 ± 0.19 |
| SF162 | | | |
| VRC01p:GRFT | 0.56 ± 0.15 | 0.35 ± 0.12 | 0.25 ± 0.13 |
| VRC01p:MVC | 0.65 ± 0.14 | 0.55 ± 0.22 | 0.56 ± 0.27 |
| VRC01p:TFV | 0.70 ± 0.07 | 0.44 ± 0.16 | 0.34 ± 0.18 |
| SS1196.1 | | | |
| VRC01p:GRFT | 0.42 ± 0.17 | 0.39 ± 0.13 | 0.39 ± 0.10 |
| VRC01p:MVC | 0.31 ± 0.10 | 0.32 ± 0.10 | 0.27 ± 0.09 |
| VRC01p:TFV | 0.67 ± 0.07 | 0.60 ± 0.04 | 0.54 ± 0.08 |
| Du156 | | | |
| VRC01p:GRFT | 0.30 ± 0.02 | 0.48 ± 0.10 | 0.38 ± 0.18 |
| VRC01p:MVC | 0.36 ± 0.10 | 0.45 ± 0.09 | 0.48 ± 0.19 |
| VRC01p:TFV | 0.55 ± 0.08 | 0.53 ± 0.03 | 0.53 ± 0.06 |

TABLE 2-continued

Combination index (CI) values for VRC01p in combination with other inhibitors.

| Inhibitors | CI 50% | CI 75% | CI 90% |
|---|---|---|---|
| ZM214M.PL15 | | | |
| VRC01p:GRFT | 0.47 ± 0.12 | 0.34 ± 0.09 | 0.34 ± 0.11 |
| VRC01p:MVC | 0.61 ± 0.15 | 0.26 ± 0.13 | 0.13 ± 0.08 |
| VRC01p:TFV | 0.59 ± 0.17 | 0.51 ± 0.19 | 0.46 ± 0.20 |

For synergy statistics, CalcuSyn software (Biosoft) was used to determine CI values based on the multiple drug effect equation of Chou and Talalay as described in Materials and Methods. CI<0.9 indicates synergy; CI 0.9-1.1 indicates addition; CI>1.1 indicates antagonism. Values show the mean of at least three independent experiments performed in triplicate±SEM.

TABLE 3

$IC_{50}$ and dose reduction index (DRI) values for VRC01p in combination with other inhibitors

| | $IC_{50}{}^a$ | $IC_{50}{}^b$ | DRI$^c$ |
|---|---|---|---|
| Q769.h5 | | | |
| VRC01p:GRFT | 0.37 ± 0.08 | 0.09 ± 0.02 | 4.89 ± 1.03 |
| VRC01p:MVC | 0.54 ± 0.11 | 0.05 ± 0.01 | 6.15 ± 0.72 |
| VRC01p:TFV | 0.47 ± 0.12 | 0.13 ± 0.03 | 3.93 ± 0.79 |
| SF162 | | | |
| VRC01p:GRFT | 0.98 ± 0.33 | 0.13 ± 0.04 | 10.3 ± 3.22 |
| VRC01p:MVC | 0.50 ± 0.27 | 0.16 ± 0.10 | 3.79 ± 0.48 |
| VRC01p:TFV | 0.65 ± 0.43 | 0.14 ± 0.05 | 4.26 ± 1.67 |
| SS1196.1 | | | |
| VRC01p:GRFT | 2.61 ± 0.12 | 0.44 ± 0.06 | 6.47 ± 1.31 |
| VRC01p:MVC | 2.22 ± 0.40 | 0.30 ± 0.17 | 5.11 ± 0.72 |
| VRC01p:TFV | 2.14 ± 0.23 | 0.74 ± 0.13 | 2.98 ± 0.28 |
| Du156 | | | |
| VRC01p:GRFT | 0.25 ± 0.04 | 0.03 ± 0.01 | 7.73 ± 0.64 |
| VRC01p:MVC | 0.26 ± 0.04 | 0.06 ± 0.02 | 3.87 ± 0.56 |
| VRC01p:TFV | 0.23 ± 0.05 | 0.06 ± 0.01 | 4.58 ± 0.65 |
| ZM214M.PL15 | | | |
| VRC01p:GRFT | 1.42 ± 0.43 | 0.27 ± 0.10 | 6.04 ± 1.01 |
| VRC01p:MVC | 0.58 ± 0.27 | 0.19 ± 0.07 | 6.49 ± 2.34 |
| VRC01p:TFV | 1.43 ± 0.50 | 0.30 ± 0.13 | 5.13 ± 0.64 |

All values calculated by CalcuSyn from the combined data sets of at least three independent experiments performed in triplicate and expressed as mean ± SEM.
$^a IC_{50}$ (µg/ml) for VRC01p alone.
$^b IC_{50}$ (µg/ml) for VRC01p in a respective combination with each inhibitor.
$^c$The DRI for VRC01p in a respective combination with each inhibitor.

TABLE 4

$IC_{50}$ and DRI values for GRFT, MVC, TFV in combination with VRC01p

| | $IC_{50}{}^a$ | $IC_{50}{}^b$ | DRI$^c$ |
|---|---|---|---|
| Q769.h5 | | | |
| GRFT | 12.4 ± 2.88 | 0.79 ± 0.19 | 11.3 ± 2.95 |
| MVC | 29.6 ± 7.75 | 5.27 ± 1.12 | 4.40 ± 0.71 |
| TFV | 21.2 ± 3.53 | 2.09 ± 0.39 | 8.40 ± 1.41 |
| SF162 | | | |
| GRFT | 0.59 ± 0.34 | 0.10 ± 0.03 | 3.19 ± 1.16 |
| MVC | 54.9 ± 29.3 | 18.3 ± 7.90 | 4.21 ± 0.25 |
| TFV | 2.70 ± 1.02 | 0.88 ± 0.40 | 2.10 ± 0.34 |
| SS1196.1 | | | |
| GRFT | 0.04 ± 0.01 | 0.01 ± 0.001 | 2.98 ± 0.72 |
| MVC | 96.4 ± 28.5 | 15.6 ± 8.87 | 5.06 ± 0.39 |
| TFV | 7.65 ± 2.39 | 1.92 ± 0.34 | 3.76 ± 0.68 |
| Du156 | | | |
| GRFT | 0.02 ± 0.001 | 0.003 ± 0.0004 | 6.29 ± 0.66 |
| MVC | 199 ± 40.4 | 32.2 ± 11.5 | 5.93 ± 0.96 |
| TFV | 7.14 ± 1.91 | 0.06 ± 0.23 | 3.01 ± 0.65 |
| ZM214M.PL15 | | | |
| GRFT | 1.19 ± 0.59 | 0.22 ± 0.11 | 2.35 ± 0.13 |
| MVC | 12.1 ± 4.00 | 3.79 ± 0.18 | 3.15 ± 1.04 |
| TFV | 4.55 ± 2.49 | 0.98 ± 0.23 | 1.92 ± 0.43 |

All values calculated by CalcuSyn from the combined data sets of at least three independent experiments performed in triplicate and expressed as mean ± SEM.
$^a$The $IC_{50}$ for GRFT (nM), MVC (nM), and TFV (µM) when used individually.
$^b IC_{50}$ for GRFT (nM), MVC (nM), and TFV (µM) in a respective combination with VRC01p.
$^c$The dose reduction index for GRFT, MVC, and TFV in a respective combination with VRC01p.

Table 3 also shows the $IC_{50}$ dose reduction index (DRI; the ratio of the drug inhibition alone:drug inhibition in combination) for VRC01p in combination with each inhibitor. The most successful combination in this analysis was VRC01p-GRFT, with DRIs ranging from 4.89 to 10.3, followed by VRC01p-MVC (DRIs: 3.15-5.93) and VRC01p-TFV (DRIs: 19.2-8.40). Collectively, there seems to be an overall good concordance between strong synergy and strong dose reduction for VRC01p-GRFT and VRC01p-MVC, followed by VRC01p-TFV.

Discussion of Examples 1-3

Topical HIV-1 microbicides have been proposed as a promising form of PrEP to control the global AIDS epidemic for more than 20 years. Yet, their effective compositions remain elusive. For potential use as topical microbicides, HIV-inhibitory proteins such as bnMAbs and antiviral lectins have an advantage of not conflicting with available ARV-based treatment options. However, a critical downside is their complex manufacturing process using biological systems, significantly limiting their availability in resource-poor regions. It is therefore imperative to develop a robust, scalable, and economical production system for proteins to be possible microbicide candidates. To this end, the above-described study was focused on establishing a novel plant-based production platform for the potent anti-HIV-1 bnMAb VRC01. The investigation of VRC01p's synergistic potential with other microbicide candidates was also undertaken to derive possible combinatorial strategies.

Plants are an economical and scalable protein manufacturing platform because of inexpensive natural resources used for bioproduction and the availability of established agricultural technologies. In this regards, a tobamoviral overexpression vector and the host kex2p protease was employed to develop a robust VRC01 IgG1 production system in *Nicotiana* plants. Previous transient MAb overexpression systems in *Nicotiana benthamiana*, including the magnICON, geminivirus replicon, pEAQ and plastocyaninbased systems, reported expression levels of anywhere between 100 and 750 mg/kg of leaf material upon inoculating vectors to small areas of leaf tissue; however, these do not represent yields under whole-plant expression conditions as in our system reported herein. A case study of vacuum infiltration-based large-scale MAb production (a humanized anti-CCR5 IgG) using the conventional 2-component magnICON system showed an expected yield of 250 mg/kg of leaf biomass. Considering that yields would vary among different MAbs and plant growth conditions, it was concluded that reasonably high amounts of functional VRC01p IgG1 (approximately 150 mg per kg of leaf biomass) were obtained with our new technology in less than a week after vector infiltration to whole plants.

VRC01p was shown to retain gp120-binding affinity and HIV-1 neutralizing activity in ELISA (FIG. 3A), SPR (FIG. 3B), and HIV-1 neutralization assays (FIG. 3C and Table 1), demonstrating that the present single-peptide-based expression strategy is feasible for the production of full-length IgG MAbs. Given that kex2p protease left three amino acids on the L chain's C-terminus and the H chain's N-terminus (Gly-Gly-Lys and Arg-Gly-Gly, respectively; see FIG. 2), future in vivo safety studies need to address the theoretical immunogenicity concern for clinical use of MAbs produced in this system. Alternatively, it may be possible to optimize the KP6pp sequence so that extra amino acids left on the final product are eliminated.

A major molecular-level difference between plant- and human cell-produced MAbs would be brought about by Asn297 glycosylation in the fragment crystallizable region (Fc) of the H chains. IgG molecules produced in plants, like those of human origin, are commonly glycosylated at Asn297 in the Fc region; however, the compositions of plant N-glycans slightly differ from mammalian counterparts, as represented by β(1,2)-linked xylose and α(1,3)-linked fucose. In fact, immunoblot analysis using plant-specific glycan-recognizing Abs showed that VRC01p, but not VRC01$_{HEK}$, bear such carbohydrate structures (data not shown). Previous studies have shown that plant-specific N-glycosylation at Asn297 reduced affinities to Fcγ receptors, including FcγRI, FcγRIIa, FcγRIIb, and FcγRIIIa. We also observed that VRC01p binds nearly an order of magnitude less to FcγRI than a human IgG1 isotype control in ELISA and in flow cytometry (data not shown). The complement protein C1q's binding to Fc is also glycan-dependent. Notwithstanding the possibly important roles of complement- and Fcγ receptor-mediated activities (e.g., killing of infected cells by complement-dependent cytotoxicity and antibody-dependent cell mediated cytotoxicity via FcγIIIa) in controlling HIV-1 replication in systemic compartments, their contribution to the protective efficacy of topically applied bnMAbs has not been demonstrated.

Meanwhile, immunogenicity of plant-specific glycans constitutes a theoretical safety concern. In particular, these glycans have been linked to allergenicity of various plant-derived glycoproteins. Jin et al. has shown that rabbits immunized with the plant-produced xylose- and fucose-carrying MAb 2G12 (formulated with incomplete Freund adjuvant) induced a humoral immune response to the plant N-glycans, and serum IgE from allergic patients bound to the fucosylated glycan structures. Nevertheless, it remains to be determined whether plant glycan-bearing MAbs induce an allergic response upon topical administration. Should this prove to be the case, a possible solution is to produce MAbs in a transgenic *Nicotiana benthamiana* line that is devoid of xylosyl- and fucosyl-transferases, similar to the work by Steinkeliner, et al. It should be noted that MAbs produced in such plants have been shown to exhibit more uniform glycan structures with terminal N-acetylglucosamines lacking β(1,2)-linked xylose and α(1,3)-linked fucose, exhibiting a better FcγIIIa binding affinity than mammalian cell-produced counterparts.

Figure 7:
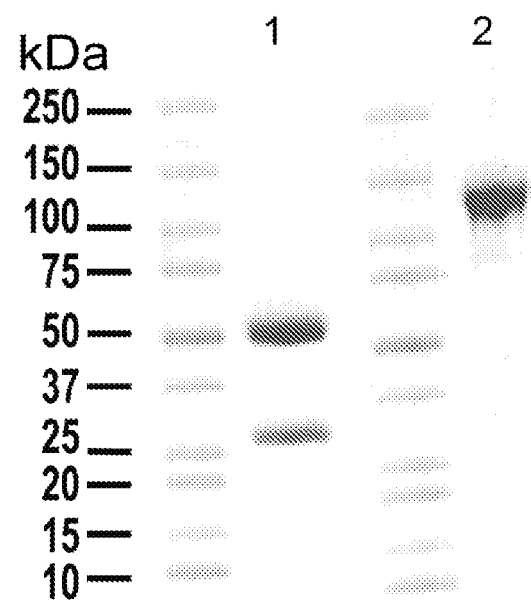
FIG. 7 is an image of a SDS-PAGE analysis of purified CR6261, where CR6261 (PDB ID: 3GBM) was expressed in N. benthamiana and purified by Protein A followed by a Phenyl HP resin, where Lane 1 is reducing conditions and Lane 2 is non-reducing conditions, and where, after the two step purification, assembled CR6261 was purified to greater than 98%.
Figure 8:
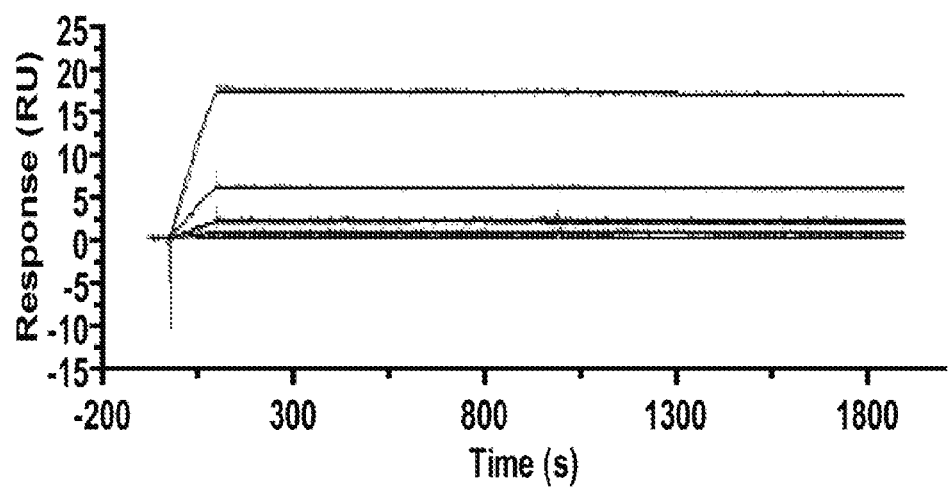
FIG. 8 is a graph showing a representative sensorgram of a SPR analysis where CR6261 was captured to approximately 200RU on a sensor chip via an anti-human IgG (Fc) antibody of IgG1 isotype and varying concentrations of recombinant hemagglutinin (HA) (A/New Caledonia/20/99; Protein Sciences) were used as analytes, where the curves represent the concentration of HA (1, 0.33, 0.11, 0.037, and 0.0123 µg/ml from top to bottom) and the lines are the bivalent analyte kinetics fit with parameter settings of R$_{max}$=local and RI set to zero, and where the equilibrium dissociation constant, K$_D$, for CR6261 was determined to be 0.055±0.0036 nM.

Compared to conventional IgG production systems that rely on two separate vectors for H and L chains, the present single vector system will require a significantly simplified manufacturing control procedure. Other reported single-vector-based IgG production systems still rely on two separate transcription units. In contrast, our system generates IgG from a single polypeptide transgene and therefore has a potential to provide more consistency and stability in MAb production. Furthermore, our system uses much less agrobacteria for vector delivery (OD$_{600}$ of 0.03) than any other similar transient overexpression system, which used agrobacteria at OD$_{600}$ ranging from 0.2 to over 1.0; a significant factor for commercial scale production. Collectively, we propose our single vector-single transgene-based IgG system developed here has some compelling advantages over other plant-based systems. Recent advances in MAb isolation technologies has significantly facilitated the identification of highly potent bnMAbs, and some of these bnMAbs have shown better neutralizing strength and/or breadth than VRC01, such as anti-gp120 PGT MAbs and anti-gp41 10E8. A VRC01-like bnMAb with superior HIV-1-neutralizing activity was also identified. As such, it is further believed that more potent and diverse bnMAbs will be continuously identified in the future, and that the presently-described plant-based production system may facilitate the pharmaceutical development of these bnMAbs along with VRC01p, as well as other MAbs targeting different infectious and chronic diseases. To investigate the widespread potential of this single-transgene system, various other MAbs were thus produced in *N. benthamiana* in accordance with the presently-described methods. For instance, and as described in further detail in the Examples below, the anti-influenza bnMAb CR6261 IgG1 was successfully expressed and purified using the same procedure (FIG. 7). Furthermore, the plant-produced CR6261 was also shown to bind to recombinant H1N1 hemagglutinin with a potent sub-nanomolar affinity in SPR analysis (FIG. 8).

In the above-described HIV-1 neutralization assay analyzing the combination effects of VRC01p and other microbicide candidates possessing different antiviral modalities, VRC01p exhibited clear synergy with the antiviral lectin GRFT, the CCR5 antagonist MVC, and the RT inhibitor TFV in multiple CCR5-using HIV-1 strains from clade A, B, and C. While only 5 viruses were tested here, all combinations showed clear synergism, with VRC01p-GRFT and VRC01p-MVC combinations being overall more synergistic than VRC01p-TFV. Of interest is the fact that VRC01p showed such consistent synergism with other entry inhibitors, suggesting multi-component entry inhibition as a potential HIV prevention strategy. Similar to the above results, Alexandre et al. showed that another CD4bs-specific bnMAb b12 synergized with GRFT in neutralizing infectivity of a few viruses; this was associated with GRFT-mediated enhancement of viral binding to the MAb. On the other hand, the above results show, for the first time, CD4bs-specific bnMAb's synergism with CCR5 antagonists and RT inhibitors. Collectively, the data suggested the broad synergistic potential of these drug combinations and in turn provided implications for possible combinatorial approaches for the microbicide use of VRC01p.

In summary, the foregoing Examples describe a novel plant-based production system for the anti-HIV-1 bnMAb, VRC01p, in *N. benthamiana* plants. The bnMAb was efficiently produced in less than a week and was comparable to human-cell produced VRC01 in terms of its gp120-binding and HIV-1 neutralizing properties. Moreover, VRC01p exhibited HIV-1 neutralization synergism with GRFT, MVC, and TFV, providing implications for combinatorial HIV-1 prevention strategies.

Example 4—Production of Combinations of Antibodies

Figure 9:
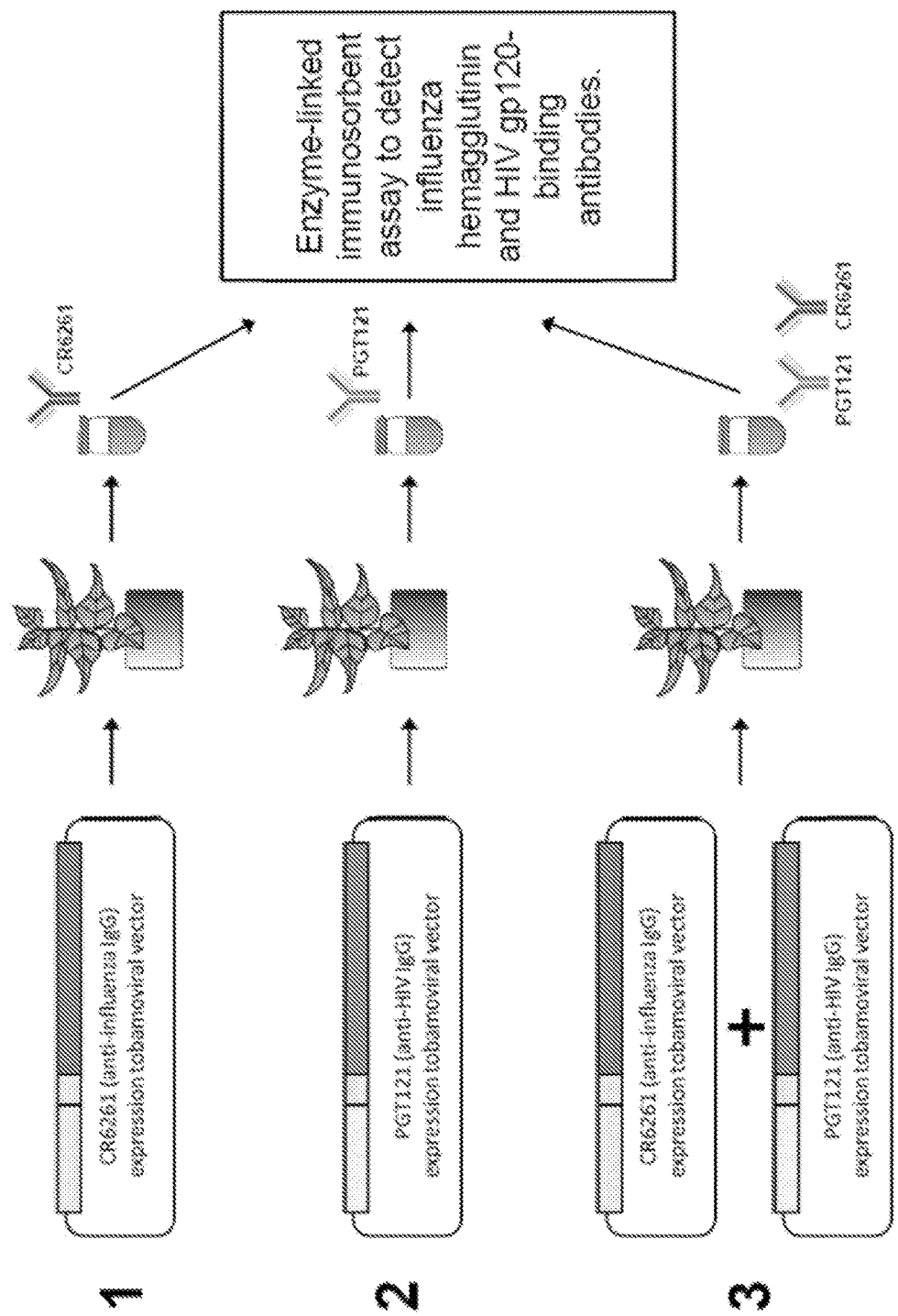
FIG. 9 is a schematic diagram showing the infiltration of plants with agrobacteria harboring a tobamovirus vector expressing either the anti-influenza IgG MAb CR6261, the anti-HIV IgG MAb PGT121, or a combination of the two MAbs.

To further analyze the production of virus-neutralizing antibodies in plants, additional experiments were undertaken to assess the production of the anti-influenza IgG MAb CR6261 and the anti-HIV IgG MAb PGT121, or the production of a combination of the two MAbs in single plant. Briefly, in those experiments, *Nicotiana benthamiana* plants were infiltrated with agrobacteria harboring a tobamovirus vector expressing either the anti-influenza IgG monoclonal antibody (MAb) CR6261, the anti-HIV IgG MAb PGT121 or a 1:1 combination of the two MAbs (FIG. 9). Seven days post-vector inoculation, leaf extracts were then analyzed for MAb production by enzyme-linked immunosorbent assays (ELISAs) detecting influenza hemagglutinin (HA)- and HIV gp120-binding MAbs.

Figure 10A:
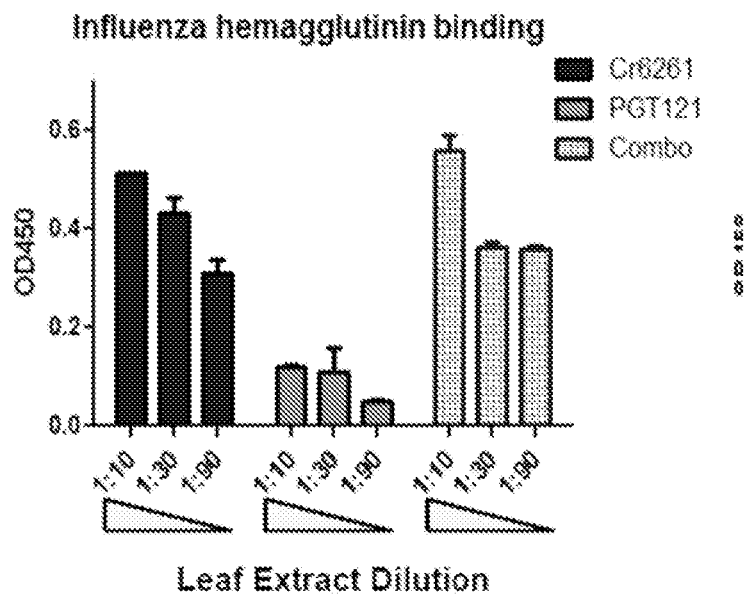
FIGS. 10A-10B are graphs showing the results of an ELISA performed with plant-produced anti-influenza IgG MAb CR6261, anti-HIV IgG MAb PGT121, or a combination of the two MAbs, including a graph showing the results of an ELISA assessing hemagglutinin (HA) binding by the MAbs (FIG. 10A) and a graph showing the result of an ELISA assessing HIV gp120 binding of the MAbs (FIG. 10B)
Figure 10B:
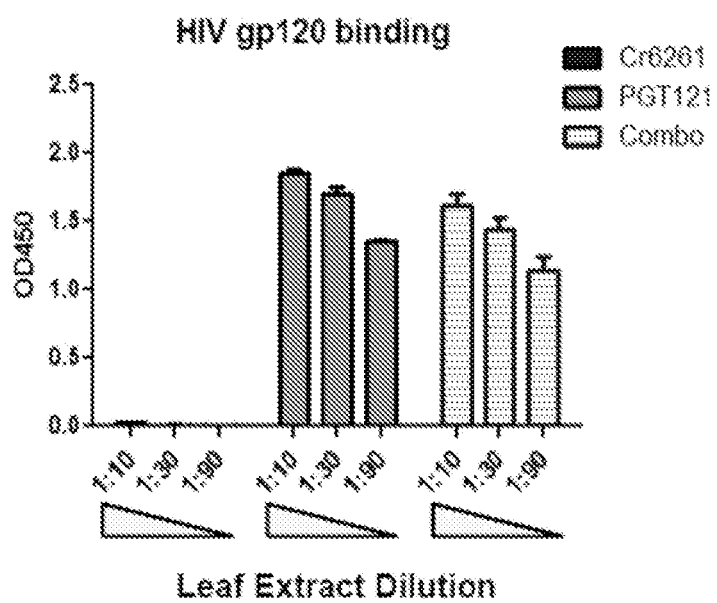

As shown in FIG. 10A, the HA-binding ELISA showed that plants infiltrated with a vector expressing CR6261 alone or CR6261/PGT121 combination, but not PGT121 alone, produced the anti-influenza MAb. Meanwhile, as shown in FIG. 10B, gp120-binding ELISA showed that plants infiltrated with a vector expressing PGT121 alone or CR6261/PGT121 combination, but not CR6261 alone, produced the anti-HIV MAb. Thus, the results demonstrated that infiltration of a single plant with a combination of two different IgG MAb-expressing vectors provides simultaneous production of the two MAbs. Because the amounts of each MAb expressed in the combination-infiltrated plants as compared to those in respective single vector-infiltrated plants were similar, randomization of light and heavy chains between the two MAbs did not seem to have occurred (which would have caused a significantly lower level of production for both MAbs in the combination plants). As such, the foregoing results thus demonstrated that combination MAb production was able to be performed in the present plant-based production platforms.

Example 5—Production of Secretory IgA in Plants

To further assess plant-based production of antibodies using the presently-described plant based production platforms, experiments are also undertaken to assess the production of secretory IgA antibodies. Secretory (S)-IgA is a type of antibody molecules that are most abundant in mucosal secretions and serve as a first line of defense against pathogen invasion. S-IgA forms a dimer, which consists of a secretory component and two monomeric IgA molecules joined by a J chain. Because of its high avidity (4 antigen binding sites in S-IgA versus 2 in IgG) and high stability against enzyme degradation (Corthésy, Autoimmunity Reviews 12(6): 661-5, 2013; Brandtzaeg, Frontiers in immunology 4: 222, 2013), S-IgA is thought to be capable of providing effective biotherapeutic tools against mucosally transmitting pathogens. However, recombinant production of S-IgA has been challenging due to the requirement of simultaneously expressing four transgenes encoding heavy chain, light chain, J chain, and secretory component—respectively. In this regard, and without wishing to be bound by any particular theory, it was believed that S-IgA could be efficiently bioproduced in plants by utilizing the above-described single vector-based monoclonal antibody production technology.

Figure 11A:
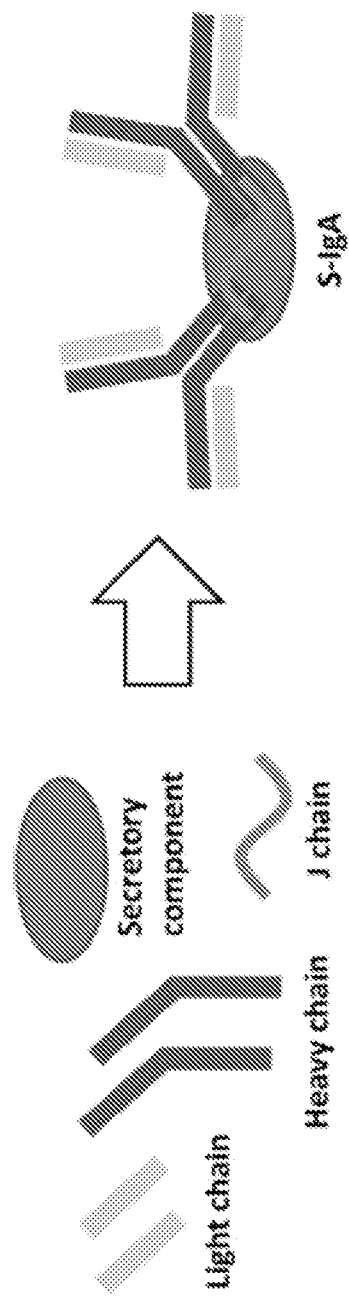
FIGS. 11A-11C are schematic diagrams showing the plant-based production of secretory IgA (S-IgA) antibodies, including: a schematic diagram showing the components of S-IgA in assembled and unassembled form (FIG. 11A); a schematic diagram showing the infiltration of plants with a single vector including the light chain, heavy chain, J chain and secretory component of IgA separated by Kex2p enzyme recognition sites (FIG. 11B); and a schematic diagram showing the infiltration of plants with two vectors, where, in one embodiment, the S-IgA light chain and heavy chain are included in a first vector and are separated by Kex2p enzyme recognition sites while the S-IgA J chain and secretory component are included in a second vector and are separated by Kex2p enzyme recognition sites (FIG. 11C, left), and where, in another embodiment, the S-IgA heavy chain and J chain are included in a first vector and are separated by Kex2p enzyme recognition sites while the S-IgA light chain and secretory component are included in a second vector and are separated by Kex2p enzyme recognition sites (FIG. 11C, right).
Figure 11B:
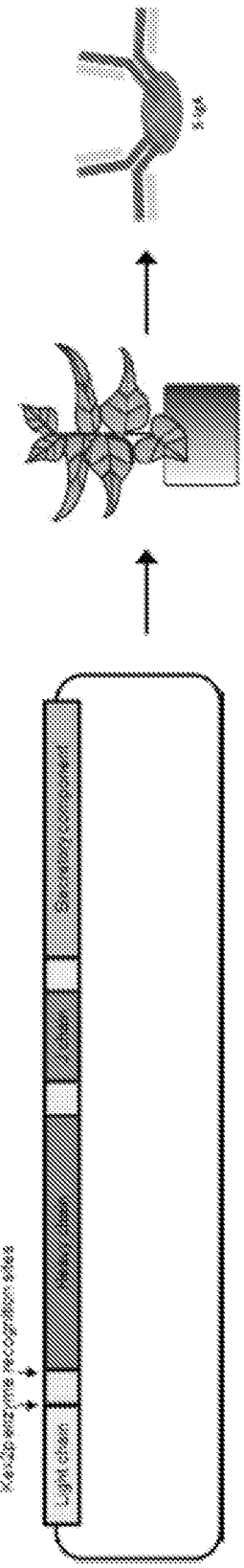
Figure 11C:
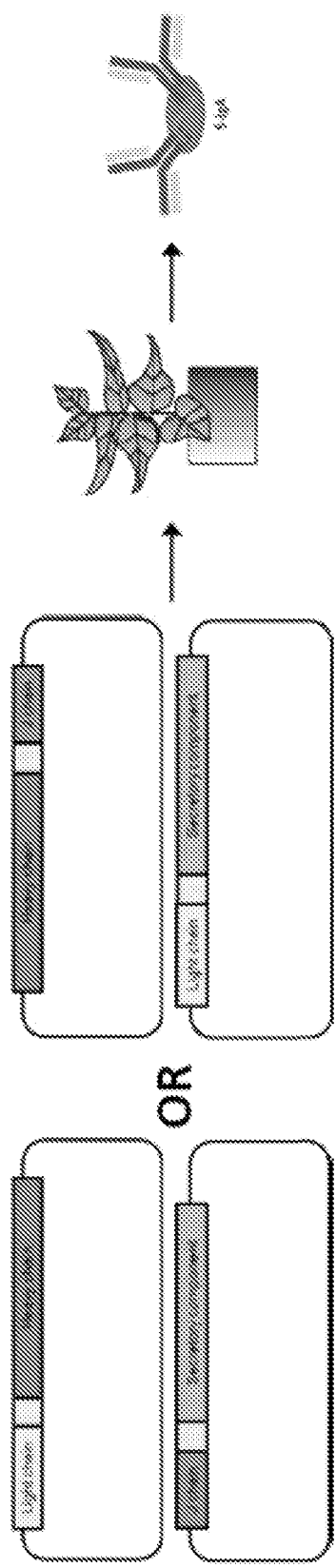

In particular, to assess whether S-IgA can be produced using the plant-based production platform, both a single vector and a two vector system are designed. In the single vector system, the S-IgA light chain, heavy chain, J chain, and secretory component are included on a single expression vector, with each component being separated by Kex2p enzyme recognitions sites (FIG. 11A). In the two vector system, two non-competing viral vectors (e.g., tobacco mosaic virus and potato virus X) are used. In one embodiment of the two vector system, the S-IgA light chain and heavy chain are included in a first vector and are separated by Kex2p enzyme recognition sites, while the S-IgA J chain and secretory component are included in a second vector and are separated by Kex2p enzyme recognition sites (FIG. 11B, top). In another embodiment of the two vector system, the S-IgA heavy chain and J chain are included in a first vector and are separated by Kex2p enzyme recognition sites, and the S-IgA light chain and secretory component are included in a second vector and are separated by Kex2p enzyme recognition sites (FIG. 11B, bottom). Regardless of the design of the vectors, however, after assembling the vectors, *Nicotiana benthamiana* plants are again infiltrated with agrobacteria harboring the vectors and leaf extracts are analyzed for S-IgA production by enzyme-linked immunosorbent assays (ELISAs). Upon analysis of the results, it is observed that S-IgA was efficiently produced in the plants using each of the vectors design, thus demonstrating that S-IgA production is also able to be performed in the present plant-based production platforms.

Throughout this document, various references are mentioned. All such references are incorporated herein by reference, including the references set forth in the following list:

REFERENCES 1. 2012. Global report: UNAIDS report on the global AIDS epidemic|2012. Joint United Nations Programme on HIV/AIDS.
2. Buckheit K W, Buckheit R W, Jr. 2012. Factors Important to the Prioritization and Development of Successful Topical Microbicides for HIV-1. Mol. Biol. Int. 2012:781305. doi:10.1155/2012/781305.
3. McGowan I. 2010. Microbicides for HIV prevention: reality or hope? Curr. Opin. Infect. Dis. 23:26-31.
4. Van Damme L, Szpir M. 2012. Current status of topical antiretroviral chemoprophylaxis. Curr. Opin. HIV AIDS 6:520-525.
5. Abdool Karim Q, Abdool Karim S S, Frohlich J A, Grobler A C, Baxter C, Mansoor L E, Kharsany A B, Sibeko S, Mlisana K P, Omar Z, Gengiah T N, Maarschalk S, Arulappan N, Mlotshwa M, Morris L, Taylor D. 2010. Effectiveness and safety of tenofovir gel, an antiretroviral microbicide, for the prevention of HIV infection in women. Science 329:1168-1174.
6. Holmes D. 2012. FDA treads carefully with PrEP. Lancet Infect. Dis. 12:515-516.
7. Macklin R, Cowan E. 2012. Given financial constraints, it would be unethical to divert antiretroviral drugs from treatment to prevention. Health Aff. 31:1537-1544.
8. Hessell A J, Rakasz E G, Poignard P, Hangartner L, Landucci G, Forthal D N, Koff W C, Watkins D I, Burton D R. 2009. Broadly neutralizing human anti-HIV antibody 2G12 is effective in protection against mucosal SHIV challenge even at low serum neutralizing titers. PLoS Pathog. 5:e1000433.
9. Hessell A J, Rakasz E G, Tehrani D M, Huber M, Weisgrau K L, Landucci G, Forthal D N, Koff W C, Poignard P, Watkins D I, Burton D R. 2010. Broadly Neutralizing Monoclonal Antibodies 2F5 and 4E10, Directed Against the Human Immunodeficiency Virus Type 1 (HIV-1) gp41Membrane Proximal External Region (MPER), Protect Against SHIVBa-L Mucosal Challenge. J. Virol. 84:1302-1313.
10. Burton D R, Hessell A J, Keele B F, Klasse P J, Ketas T A, Moldt B, Dunlop D C, Poignard P, Doyle L A, Cavacini L, Veazey R S, Moore J P. 2011. Limited or no protection by weakly or nonneutralizing antibodies against vaginal SHIV challenge of macaques compared with a strongly neutralizing antibody. Proc. Natl. Acad. Sci. U.S.A. 108:11181-11186.
11. Veazey R S, Shattock R J, Pope M, Kirijan J C, Jones J, Hu Q, Ketas T, Marx P A, Klasse P J, Burton D R, Moore J P. 2003. Prevention of virus transmission to macaque monkeys by a vaginally applied monoclonal antibody to HIV-1 gp120. Nat. Med. 9:343-346.
12. Watkins J D, Siddappa N B, Lakhashe S K, Humbert M, Sholukh A, Hemashettar G, Wong Y L, Yoon J K, Wang W, Novembre F J, Villinger F, Ibegbu C, Patel K, Corti D, Agatic G, Vanzetta F, Bianchi S, Heeney J L, Sallusto F, Lanzavecchia A, Ruprecht R M. 2011. An anti-HIV-1 V3 loop antibody fully protects cross-clade and elicits T-cell immunity in macaques mucosally challenged with an R5 clade C SHIV. PLoS ONE 6:e18207.
13. Klein F, Halper-Stromberg A, Horwitz J A, Gruell H, Scheid J F, Bournazos S, Mouquet H, Spatz L A, Diskin R, Abadir A, Zang T, Dorner M, Billerbeck E, Labitt R N, Gaebler C, Marcovecchio P M, Incesu R B, Eisenreich T R, Bieniasz P D, Seaman M S, Bjorkman P J, Ravetch J V, Ploss A, Nussenzweig M C. 2012. HIV therapy by a combination of broadly neutralizing antibodies in humanized mice. Nature 492:118-122.
14. Moldt B, Rakasz E G, Schultz N, Chan-Hui P Y, Swiderek K, Weisgrau K L, Piaskowski S M, Bergman Z, Watkins D I, Poignard P, Burton D R. 2012. Highly potent HIV-specific antibody neutralization in vitro translates into effective protection against mucosal SHIV challenge in vivo. Proc. Natl. Acad. Sci. U.S.A. 109:18921-18925.
15. Morris G, Wiggins R, Woodhall S, Taylor C, Vcelar B, Bland M, Lacey C. 2011. A Phase 1 Randomized Controlled Trial of a Triple Anti-HIV-1 Monoclonal Antibody Vaginal Microbicide, p. Paper #990, 18th Conference on Retroviruses and Opportunistic Infections, Boston, Mass.
16. Wu X, Yang Z Y, Li Y, Hogerkorp C M, Schief W R, Seaman M S, Zhou T, Schmidt S D, Wu L, Xu L, Longo N S, McKee K, O'Dell S, Louder M K, Wycuff D L, Feng Y, Nason M, Doria-Rose N, Connors M, Kwong P D, Roederer M, Wyatt R T, Nabel G J, Mascola J R. 2010. Rational design of envelope identifies broadly neutralizing human monoclonal antibodies to HIV-1. Science 329:856-861.
17. Wilen C B, Parrish N F, Pfaff J M, Decker J M, Henning E A, Haim H, Petersen J E, Wojcechowskyj J A, Sodroski J, Haynes B F, Montefiori D C, Tilton J C, Shaw G M, Hahn B H, Doms R W. 2011. Phenotypic and immunologic comparison of clade B transmitted/founder and chronic HIV-1 envelope glycoproteins. J. Virol. 85:8514-8527.
18. Parrish N F, Wilen C B, Banks L B, Iyer S S, Pfaff J M, Salazar-Gonzalez J F, Salazar M G, Decker J M, Parrish E H, Berg A, Hopper J, Hora B, Kumar A, Mahlokozera T, Yuan S, Coleman C, Vermeulen M, Ding H, Ochsenbauer C, Tilton J C, Permar S R, Kappes J C, Betts M R, Busch M P, Gao F, Montefiori D, Haynes B F, Shaw G M, Hahn B H, Doms R W. 2012. Transmitted/founder and chronic subtype C HIV-1 use CD4 and CCR5 receptors with equal efficiency and are not inhibited by blocking the integrin alpha4beta7. PLoS Pathog. 8:e1002686.
19. Baalwa J, Wang S, Parrish N F, Decker J M, Keele B F, Learn G H, Yue L, Ruzagira E, Ssemwanga D, Kamali A, Amornkul P N, Price M A, Kappes J C, Karita E, Kaleebu P, Sanders E, Gilmour J, Allen S, Hunter E, Montefiori D C, Haynes B F, Cormier E, Hahn B H, Shaw G M. 2012. Molecular identification, cloning and characterization of transmitted/founder HIV-1 subtype A, D and A/D infectious molecular clones. Virology. doi:10.1016/j.virol.2012.10.009.
20. Veselinovic M, Preston Neff C, Mulder L R, Akkina R. 2012. Topical gel formulation of broadly neutralizing anti-HIV-1 monoclonal antibody VRC01 confers protection against HIV-1 vaginal challenge in a humanized mouse model. Virology 432:505-510.
21. Wu X, Wang C, O'Dell S, Li Y, Keele B F, Yang Z, Imamichi H, Doria-Rose N, Hoxie J A, Connors M, Shaw G M, Wyatt R T, Mascola J R. 2012. Selection Pressure on HIV-1 Envelope by Broadly Neutralizing Antibodies to the Conserved C D4-Binding Site. J. Virol. 86:5844-5856.
22. Pirrone V, Thakkar N, Jacobson J M, Wigdahl B, Krebs F C. 2011. Combinatorial approaches to the prevention and treatment of HIV-1 infection. Antimicrob. Agents Chemother. 55:1831-1842.
23. Whaley K J, Hiatt A, Zeitlin L. 2011. Emerging antibody products and *Nicotiana* manufacturing. Hum. Vaccin. 7:466-470.
24. Matoba N, Davis K R, Palmer K E. 2011. Recombinant Protein Expression in *Nicotiana*. Methods Mol. Biol. 701:199-219.
25. Giritch A, Marillonnet S, Engler C, van Eldik G, Botterman J, Klimyuk V, Gleba Y. 2006. Rapid high-yield expression of full-size IgG antibodies in plants coinfected with noncompeting viral vectors. Proc. Natl. Acad. Sci. U.S.A. 103:14701-14706.
26. Kouokam J C, Huskens D, Schols D, Johannemann A, Riedell S K, Walter W, Walker J M, Matoba N, O'Keefe B R, Palmer K E. 2011. Investigation of griffithsin's interactions with human cells confirms its outstanding safety and efficacy profile as a microbicide candidate. PLoS ONE 6:e22635.
27. O'Keefe B R, Vojdani F, Buffa V, Shattock R J, Montefiori D C, Bakke J, Mirsalis J, d'Andrea A L, Hume S D, Bratcher B, Saucedo C J, McMahon J B, Pogue G P, Palmer K E. 2009. Scaleable manufacture of HIV-1 entry inhibitor griffithsin and validation of its safety and efficacy as a topical microbicide component. Proc. Natl. Acad. Sci. U.S.A. 106:6099-6104.
28. Marillonnet S, Thoeringer C, Kandzia R, Klimyuk V, Gleba Y. 2005. Systemic *Agrobacterium tumefaciens*-mediated transfection of viral replicons for efficient transient expression in plants. Nat. Biotechnol. 23:718-723.
29. Matoba N, Husk A S, Barnett B W, Pickel M M, Arntzen C J, Montefiori D C, Takahashi A, Tanno K, Omura S, Cao H, Mooney J P, Hanson C V, Tanaka H. 2010. HIV-1 neutralization profile and plant-based recombinant expression of actinohivin, an Env glycan-specific lectin devoid of T-cell mitogenic activity. PLoS ONE 5:e11143.

30. Montefiori D C. 2009. Measuring HIV neutralization in a luciferase reporter gene assay. Methods Mol. Biol. 485:395-405.
31. Zhang P F, Chen X, Fu D W, Margolick J B, Quinnan G V, Jr. 1999. Primary virus envelope cross-reactivity of the broadening neutralizing antibody response during early chronic human immunodeficiency virus type 1 infection. J. Virol. 73:5225-5230.
32. Cheng-Mayer C, Levy J A. 1988. Distinct biological and serological properties of human immunodeficiency viruses from the brain. Ann. Neurol. 23 Suppl:S58-61.
33. Li M, Salazar-Gonzalez J F, Derdeyn C A, Morris L, Williamson C, Robinson J E, Decker J M, Li Y, Salazar M G, Polonis V R, Mlisana K, Karim S A, Hong K, Greene K M, Bilska M, Zhou J, Allen S, Chomba E, Mulenga J, Vwalika C, Gao F, Zhang M, Korber B T, Hunter E, Hahn B H, Montefiori D C. 2006. Genetic and Neutralization Properties of Acute and Early Subtype C Human Immunodeficiency Virus Type 1 Molecular env Clones from Heterosexually Acquired Infections in Southern Africa. J. Virol. 80:11776-11790.
34. Blish C A, Jalalian-Lechak Z, Rainwater S, Nguyen M A, Dogan O C, Overbaugh J. 2009. Cross-subtype neutralization sensitivity despite monoclonal antibody resistance among early subtype A, C, and D envelope variants of human immunodeficiency virus type 1. J. Virol. 83:7783-7788.
35. Montefiori D C 2011, posting date. Protocol for the Preparation and Titration of HIV-1 Env-pseudotyped Viruses. Los Alamos National Security, LLC. http://www.hiv.lanl.gov/content/nab-reference-strains/html/Protocol-for-Preparation-and-Titration-of-HIV-1-Env-pseudotyped-Viruses-December-2011.pdf.
36. Landau N R, Littman D R. 1992. Packaging system for rapid production of murine leukemia virus vectors with variable tropism. J. Virol. 66:5110-5113.
37. Deng H, Liu R, Ellmeier W, Choe S, Unutmaz D, Burkhart M, Di Marzio P, Marmon S, Sutton R E, Hill C M, Davis C B, Peiper S C, Schall T J, Littman D R, Landau N R. 1996. Identification of a major co-receptor for primary isolates of HIV-1. Nature 381:661-666.
38. Chou T C, Talalay P. 1984. Quantitative analysis of dose-effect relationships: the combined effects of multiple drugs or enzyme inhibitors. Adv. Enzyme Regul. 22:27-55.
39. De Muynck B, Navarre C, Boutry M. 2010. Production of antibodies in plants: status after twenty years. Plant Biotechnol. J. 8:529-563.
40. Zhang B, Rapolu M, Huang L, Su W W. 2011. Coordinate expression of multiple proteins in plant cells by exploiting endogenous kex2p-like protease activity. Plant Biotechnol. J. 9:970-981.
41. Kinal H, Park C M, Berry J O, Koltin Y, Bruenn J A. 1995. Processing and secretion of a virally encoded antifungal toxin in transgenic tobacco plants: evidence for a Kex2p pathway in plants. Plant Cell 7:677-688.
42. Malcolm R K, Forbes C J, Geer L, Veazey R S, Goldman L, Johan Klasse P, Moore J P. 2012. Pharmacokinetics and efficacy of a vaginally administered maraviroc gel in rhesus macaques. J. Antimicrob. Chemother. 67:2779-2781.
43. Neff C P, Kurisu T, Ndolo T, Fox K, Akkina R. 2011. A topical microbicide gel formulation of CCR5 antagonist maraviroc prevents HIV-1 vaginal transmission in humanized RAG-hu mice. PLoS ONE 6:e20209.
44. Ma J K, Drake P M, Christou P. 2003. The production of recombinant pharmaceutical proteins in plants. Nat. Rev. Genet. 4:794-805.
45. Huang Z, Phoolcharoen W, Lai H, Piensook K, Cardineau G, Zeitlin L, Whaley K J, Arntzen C J, Mason H S, Chen Q. 2009. High-level rapid production of full-size monoclonal antibodies in plants by a single-vector DNA replicon system. Biotechnol. Bioeng. 106:9-17.
46. Sainsbury F, Thuenemann E C, Lomonossoff G P. 2009. pEAQ: versatile expression vectors for easy and quick transient expression of heterologous proteins in plants. Plant Biotechnol. J. 7:682-693.
47. Vezina L P, Faye L, Lerouge P, D'Aoust M A, Marquet-Blouin E, Burel C, Lavoie P O, Bardor M, Gomord V. 2009. Transient co-expression for fast and high-yield production of antibodies with human-like N-glycans in plants. Plant Biotechnol. J. 7:442-455.
48. Pogue G P, Vojdani F, Palmer K E, Hiatt E, Hume S, Phelps J, Long L, Bohorova N, Kim D, Pauly M, Velasco J, Whaley K, Zeitlin L, Garger S J, White E, Bai Y, Haydon H, Bratcher B. 2010. Production of pharmaceutical-grade recombinant aprotinin and a monoclonal antibody product using plant-based transient expression systems. Plant Biotechnol. J. 8:638-654.
49. Forthal D N, Gach J S, Landucci G, Jez J, Strasser R, Kunert R, Steinkellner H. 2010. Fc-glycosylation influences Fcgamma receptor binding and cell-mediated anti-HIV activity of monoclonal antibody 2G12. J. Immunol. 185:6876-6882.
50. Strasser R, Stadlmann J, Schahs M, Stiegler G, Quendler H, Mach L, Glossl J, Weterings K, Pabst M, Steinkellner H. 2008. Generation of glyco-engineered *Nicotiana benthamiana* for the production of monoclonal antibodies with a homogeneous human-like N-glycan structure. Plant Biotechnol. J. 6:392-402.
51. Zeitlin L, Pettitt J, Scully C, Bohorova N, Kim D, Pauly M, Hiatt A, Ngo L, Steinkellner H, Whaley K J, Olinger G G. 2011. Enhanced potency of a fucose-free monoclonal antibody being developed as an Ebola virus immunoprotectant. Proc. Natl. Acad. Sci. U.S.A. 108:20690-20694.
52. Hessell A J, Hangartner L, Hunter M, Havenith C E, Beurskens F J, Bakker J M, Lanigan C M, Landucci G, Forthal D N, Parren P W, Marx P A, Burton D R. 2007. Fc receptor but not complement binding is important in antibody protection against HIV. Nature 449:101-104.
53. Forthal D N, Moog C. 2009. Fc receptor-mediated antiviral antibodies. Curr. Opin. HIV AIDS 4:388-393.
54. Robinson H L. 2012. Non-neutralizing antibodies in prevention of HIV infection. Expert Opin. Biol. Ther. 13:197-207.
55. Bosch D, Schots A. 2010. Plant glycans: friend or foe in vaccine development? Expert Rev. Vaccines 9:835-842.
56. Jin C, Altmann F, Strasser R, Mach L, Schahs M, Kunert R, Rademacher T, Glossl J, Steinkellner H. 2008. A plant-derived human monoclonal antibody induces an anti-carbohydrate immune response in rabbits. Glycobiology 18:235-241.
57. Castilho A, Bohorova N, Grass J, Bohorov O, Zeitlin L, Whaley K, Altmann F, Steinkellner H. 2011. Rapid high yield production of different glycoforms of Ebola virus monoclonal antibody. PLoS ONE 6:e26040.
58. Walker L M, Huber M, Doores K J, Falkowska E, Pejchal R, Julien J P, Wang S K, Ramos A, Chan-Hui P Y, Moyle M, Mitcham J L, Hammond P W, Olsen O A, Phung P, Fling S, Wong C H, Phogat S, Wrin T, Simek M D, Principal Investigators P G, Koff W C, Wilson I A, Burton D R, Poignard P. 2011. Broad neutralization coverage of HIV by multiple highly potent antibodies. Nature 477:466-470.
59. Huang J, Ofek G, Laub L, Louder M K, Doria-Rose N A, Longo N S, Imamichi H, Bailer R T, Chakrabarti B, Sharma S K, Alam S M, Wang T, Yang Y, Zhang B, Migueles S A, Wyatt R, Haynes B F, Kwong P D, Mascola J R, Connors M. 2012. Broad and potent neutralization of HIV-1 by a gp41-specific human antibody. Nature 491: 406-412.
60. Diskin R, Scheid J F, Marcovecchio P M, West A P, Jr., Klein F, Gao H, Gnanapragasam P N, Abadir A, Seaman M S, Nussenzweig M C, Bjorkman P J. 2011. Increasing the potency and breadth of an HIV antibody by using structure-based rational design. Science 334:1289-1293.
61. Throsby M, van den Brink E, Jongeneelen M, Poon L L, Alard P, Cornelissen L, Bakker A, Cox F, van Deventer E, Guan Y, Cinatl J, ter Meulen J, Lasters I, Carsetti R, Peiris M, de Kruif J, Goudsmit J. 2008. Heterosubtypic neutralizing monoclonal antibodies cross-protective against H5N1 and H1N1 recovered from human IgM+ memory B cells. PLoS ONE 3:e3942.
62. Alexandre K B, Gray E S, Pantophlet R, Moore P L, McMahon J B, Chakauya E, O'Keefe B R, Chikwamba R, Morris L. 2011. Binding of the Mannose-Specific Lectin, Griffithsin, to HIV-1 gp120 Exposes the CD4-Binding Site. J. Virol. 85:9039-9050.
63. Sattentau Q. 2008. Avoiding the void: cell-to-cell spread of human viruses. Nat. Rev. Microbiol. 6:815-826.
64. Provine N M, Cortez V, Chohan V, Overbaugh J. 2012. The neutralization sensitivity of viruses representing human immunodeficiency virus type 1 variants of diverse subtypes from early in infection is dependent on producer cell, as well as characteristics of the specific antibody and envelope variant. Virology 427:25-33.
65. Monel B, Beaumont E, Vendrame D, Schwartz O, Brand D, Mammano F. 2012. HIV cell-to-cell transmission requires the production of infectious virus particles and does not proceed through env-mediated fusion pores. J. Virol. 86:3924-3933.
66. Abela I A, Berlinger L, Schanz M, Reynell L, Gunthard H F, Rusert P, Trkola A. 2012. Cell-cell transmission enables HIV-1 to evade inhibition by potent CD4bs directed antibodies. PLoS Pathog. 8:e1002634.
67. Selhorst P, Grupping K, Bourlet T, Delezay O, Arien K K, Vanham G. 2012. In vitro activities of candidate microbicides against cell-associated HIV. Antimicrob. Agents Chemother. 56:805-815.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for producing an antibody, comprising:
   transforming a plant cell with a nucleic acid encoding a heavy chain of the antibody, a light chain of the antibody, and a linking polypeptide connecting the heavy chain to the light chain; and
   expressing the nucleic acid in the plant cell such that, upon expression, the linking polypeptide is cleaved to separate the heavy chain from the light chain,
   wherein the antibody is selected from the group consisting of an anti-human immunodeficiency virus VRC01 antibody, an anti-human immunodeficiency virus PGT121 antibody, and an anti-influenza CR6261 antibody, and
   wherein the nucleic acid comprises a sequence selected from SEQ ID NOS: 1-4.

2. The method of claim 1, wherein the plant cell comprises a *Nicotiana* plant cell.

3. The method of claim 2, wherein the *Nicotiana* plant cell is a *Nicotiana benthamiana* plant cell.

4. The method of claim 1, wherein the linking polypeptide includes an endoproteinase cleavage site.

5. The method of claim 4, wherein the linking polypeptide comprises a Kex2p enzyme recognition site.

6. The method of claim 1, wherein the antibody comprises a monoclonal antibody.

7. The method of claim 1, wherein the antibody is a secretory IgA antibody.

8. The method of claim 7, wherein the nucleic acid further encodes a J chain of the secretory IgA antibody and a secretory component of the IgA antibody.

9. A method for producing a mixed population of antibodies, comprising:
   transforming a plant cell with a first nucleic acid encoding a heavy chain of a first antibody, a light chain of the first antibody, and a linking polypeptide connecting the heavy chain of the first antibody to the light chain of the first antibody;
   transforming the plant cell with a second nucleic acid encoding a heavy chain of a second antibody, a light chain of the second antibody, and a linking polypeptide connecting the heavy chain of the second antibody to the light chain of the second antibody; and
   expressing the first nucleic acid and second nucleic acid in the plant cell such that, upon expression of the first nucleic acid and the second nucleic acid, each linking polypeptide is cleaved to separate each heavy chain from each light chain and thereby produce the first antibody and the second antibody,
   wherein the first nucleic acid and/or the second nucleic acid comprises a sequence selected from SEQ ID NOS: 1-4.

10. The method of claim 9, wherein the first antibody and the second antibody both bind to a target protein.

11. The method of claim 10, wherein the first antibody and the second antibody bind to different epitopes on the target protein.

12. The method of claim 9, wherein the first antibody and the second antibody bind to different target proteins.

13. A method for producing an antibody, comprising:
   transforming a plant cell with a nucleic acid encoding a heavy chain of the antibody, a light chain of the antibody, and a linking polypeptide connecting the heavy chain to the light chain; and
   expressing the nucleic acid in the plant cell such that, upon expression, the linking polypeptide is cleaved to separate the heavy chain from the light chain,
   wherein the linking polypeptide is encoded by a nucleic acid having the sequence of SEQ ID NO: 9, and
   wherein the nucleic acid comprises a sequence selected from SEQ ID NOS: 1-4.

14. A method for producing an antibody, comprising:
   transforming a plant cell with a nucleic acid encoding a heavy chain of the antibody, a light chain of the antibody, and a linking polypeptide connecting the heavy chain to the light chain; and
   expressing the nucleic acid in the plant cell such that, upon expression, the linking polypeptide is cleaved to separate the heavy chain from the light chain,
   wherein the nucleic acid comprises a sequence selected from SEQ ID NOS: 1-4.

* * * * *

SEQUENCE LISTING

```
<160> NUMBER OF SEQ ID NOS: 20

<210> SEQ ID NO 1
<211> LENGTH: 2097
<212> TYPE: DNA
<213> ORGANISM: Artificial Sequence
<220> FEATURE:
<223> OTHER INFORMATION: VRC01 L-(KP6pp)-H construct

<400> SEQUENCE: 1
gaaatcgtgc ttactcagtc tccaggtact ctttctcttt ctcctggtga aactgctatt       60
atctcttgca ggacttctca gtacggatct cttgcttggt atcaacaaag accaggacaa      120
gctccaaggc ttgttatcta ttctggatct actagggctg ctggaattcc agataggttt      180
tctggatcta ggtggggacc agattacaac ctcactattt ctaaccttga gtccggtgat      240
ttcggagttt actactgtca acagtacgag ttcttcggac agggaactaa ggtgcaagtg      300
gatattaaga ggactgttgc tgctccatcc gtgtttattt tcccaccatc tgatgagcag      360
ctcaagtctg gaactgcttc tgttgtttgc ctcctcaaca atttctaccc aagggaagct      420
aaggttcagt ggaaagttga taacgctctc cagtctggaa actctcaaga atctgttact      480
gagcaggatt ctaaggattc cacttactcc ctctcctcta ctcttacttt gtccaaggct      540
gattacgaga agcacaaggt ttacgcttgc gaagttactc atcagggact tagatctcca      600
gtgactaagt cttttaacag gggagaatgt ggaggtaaga ggactattca agattccgct      660
actgatactg tggatcttgg agctgagctt catagagatg atccaccacc aactgcttcc      720
gatattggaa agagaggtgg acaagttcag cttgttcaat ctggtggaca gatgaagaaa      780
cctggtgagt ctatgaggat ttcttgcaga gcttctggct acgagttcat tgattgcact      840
cttaactgga ttaggcttgc tccaggtaag aggccagaat ggatgggatg gcttaagcca      900
agaggtggtg ctgttaatta tgctagacca ttcagggaa gggtgacaat gactagggat      960
gtttactccg atactgcttt ccttgagctt agatccctca ctgttgatga tactgctgtt     1020
```

```
tatttctgca ctaggggcaa gaactgcgat tacaattggg attttgagca ttggggaagg      1080
ggaactccag ttattgtttc ttctccttct actaagggcc catctgtttt tccacttgct      1140
ccatcttcca gtctacttc aggtggaact gctgctcttg gatgtcttgt taaggattac      1200
ttcccagagc cagttactgt gtcttggaat tctggtgctc ttacttctgg tgttcacact      1260
tttccagctg ttcttcagtc ctctggactt tactctcttt cttctgttgt gactgtgcca      1320
tcttcttcac ttggaactca gacttacatc tgcaacgtta accacaagcc atccaacaca      1380
aaagtggata agaaggcaga gccaaagtcc tgtgataaga ctcatacttg tccaccatgt      1440
ccagctccag aacttcttgg tggtccatct gttttcttgt ttccaccaaa gccaaaggat      1500
actctcatga tttctagaac tccagaggtt acatgcgttg tggttgatgt ttctcatgag      1560
gatcctgagg ttaagttcaa ctggtatgtg gatggtgttg aggttcacaa cgctaagact      1620
aagccaagag aggaacagta caactctact tacaggggttg tgtctgtgct tactgtgctt      1680
catcaggatt ggcttaacgg caaagagtac aagtgcaagg tttccaacaa ggctttgcca      1740
gctccaatcg aaaagactat tccaaggct aagggacaac ctagagagcc acaagtttac      1800
actcttccac catctaggga agagatgact aagaaccagg tttcccttac ttgccttgtg      1860
aagggattct acccatctga tattgctgtt gagtgggagt ctaatggaca gccagagaac      1920
aactacaaga ctactccacc agtgcttgat tctgatggct cattcttctt gtactccaag      1980
ctcactgtgg ataagtcaag atggcagcag ggaaatgtgt tctcttgctc tgttatgcat      2040
gaggctctcc ataatcacta cactcagaag tcccttctt tgtctcctgg caagtga       2097
```

<210> SEQ ID NO 2
<211> LENGTH: 2097
<212> TYPE: DNA
<213> ORGANISM: Artificial Sequence
<220> FEATURE:
<223> OTHER INFORMATION: VRC01 H-(KP6pp)-L construct

<400> SEQUENCE: 2

```
caagttcagc ttgttcaatc tggtggacag atgaagaaac tggtgagtc tatgaggatt       60 tcttgcagag cttctggcta cgagttcatt gattgcactc ttaactggat taggcttgct      120
ccaggtaaga ggccagaatg gatgggatgg cttaagccaa gaggtggtgc tgttaattat      180
gctagaccac ttcagggaag ggtgacaatg actaggggatg tttactccga tactgctttc      240
cttgagctta gatccctcac tgttgatgat actgctgttt attctgcac tagggggcaag      300 aactgcgatt acaattggga ttttgagcat tggggagggg gaactccagt tattgttct      360 tctccttcta ctaagggccc atctgttttt ccacttgctc catcttccaa gtctacttca      420
ggtggaactg ctgctcttgg atgtcttgtt aaggattact cccagagcc agttactgtg      480 tcttggaatt ctggtgctct tacttctggt gttcacactt tccagctgt tcttcagtcc      540 tctggacttt actctctttc ttctgttgtg actgtgccat cttcttcact tggaactcag      600
acttacatct gcaacgttaa ccacaagcca tccaacacaa aagtggataa gaaggcagag      660
ccaaagtcct gtgataagac tcatacttgt ccaccatgtc cagctccaga acttcttggt      720
ggtccatctg ttttcttgtt tccaccaaag ccaaaggata ctctcatgat ttctagaact      780
ccagaggtta catgcgttgt ggttgatgtt tctcatgagg atcctgaggt taagttcaac      840
tggtatgtgg atggtgttga ggttcacaac gctaagacta agccaagaga ggaacagtac      900
aactctactt acagggttgt gtctgtgctt actgtgcttc atcaggattg gcttaacggc      960
```

```
aaagagtaca agtgcaaggt ttccaacaag gctttgccag ctccaatcga aaagactatt    1020
tccaaggcta agggacaacc tagagagcca caagtttaca ctcttccacc atctagggaa    1080
gagatgacta agaaccaggt ttcccttact tgccttgtga agggattcta cccatctgat    1140
attgctgttg agtgggagtc taatggacag ccagagaaca actacaagac tactccacca    1200
gtgcttgatt ctgatggctc attcttcttg tactccaagc tcactgtgga taagtcaaga    1260
tggcagcagg gaaatgtgtt ctcttgctct gttatgcatg aggctctcca taatcactac    1320
actcagaagt ccctttcttt gtctcctggc aagggaggta agaggactat tcaagattcc    1380
gctactgata ctgtggatct ggagctgag cttcatagag atgatccacc accaactgct    1440
tccgatattg aaagagagg tggagaaatc gtgcttactc agtctccagg tactctttct    1500
ctttctcctg gtgaaactgc tattatctct tgcaggactt ctcagtacgg atctcttgct    1560
tggtatcaac aaagaccagg acaagctcca aggcttgtta tctattctgg atctactagg    1620
gctgctggaa ttccagatag gttttctgga tctaggtggg gaccagatta caacctcact    1680
atttctaacc ttgagtccgg tgatttcgga gtttactact gtcaacagta cgagttcttc    1740
ggacagggaa ctaaggtgca agtggatatt aagaggactg ttgctgctcc atccgtgttt    1800
attttcccac catctgatga gcagctcaag tctggaactc cttctgttgt ttgcctcctc    1860
aacaatttct acccaaggga agctaaggtt cagtggaaag ttgataacgc tctccagtct    1920
ggaaactctc aagaatctgt tactgagcag gattctaagg attccactta ctccctctcc    1980
tctactctta ctttgtccaa ggctgattac gagaagcaca aggtttacgc ttgcgaagtt    2040
actcatcagg gacttagatc tccagtgact aagtctttta cagggaga atgttga       2097

<210> SEQ ID NO 3
<211> LENGTH: 2130
<212> TYPE: DNA
<213> ORGANISM: Artificial Sequence
<220> FEATURE:
<223> OTHER INFORMATION: anti-influenza CR6261 L-(KP6pp)-H construct

<400> SEQUENCE: 3
cagtctgttc ttactcaacc accatctgtt tctgctgctc caggacaaaa ggtgacaatt      60
tcttgctctg gatcctcctc caacatcgga aacgattacg tttcatggta tcagcagctt    120
ccaggtactc tccaaagct tcttatctac gataacaaca gaggccatc cggaattcca    180 gataggtttt ctggatctaa gtccggaact tctgctactc ttggaattac tggactccaa    240
actggtgatg aggctaatta ctattgcgct acttgggata aaggccaac tgcttatgtt    300 gttttcggag gtgaactaa gcttactgtt cttggagctg ctgctggaca acctaaggct    360
gctccttctg ttactttgtt tcctccatct tctgaggaac tccaagctaa caaggctact    420
cttgtgtgcc tcatttccga ttttaccca ggtgctgtta ctgttgcttg aaggctgat    480 tcttcaccag ttaaggctgg tgttgagact actactccat ctaagcagtc aacaacaag    540 tacgctgctt cttcttactt gtctcttact ccagagcagt ggaagtctca taggtcttat    600
tcttgccaag tgactcacga gggatctact gttgaaaga ctgttgctcc aactgagtgt    660
tctggtggaa agagaactct tcaggattcc gctactgata ctgttgatct ggagctgag    720 cttcatagag atgatccacc accaactgct tccgatattg gtaagagggg aggtgaagtt    780
cagcttgttg aatctggtgc tgaggttaag aagccaggat cttctgttaa ggtttcctgt    840
aaggcttctg gtgaccttt taggtcttac gctatttctt gggttaggca agctccaggt    900
caaggaccag aatggatggg aggaattatt ccaatcttcg gcactactaa gtacgctcca    960
```

```
aagttccaag gtagggtgac aattactgct gatgattttg ctggcactgt gtacatggaa    1020
ctttcttcac ttaggtccga ggatactgct atgtactatt gtgctaagca catgggatac    1080
caggtgagag aaactatgga tgtttgggga aagggcacta ctgtgactgt ttcttctgct    1140
tctactaagg gcccatctgt ttttccactt gctccatctt ccaagtctac ttcaggtgga    1200
actgctgctc ttggatgtct tgttaaggat tacttcccag agccagttac tgtgtcttgg    1260
aattctggtg ctcttacttc tggtgttcac acttttccag ctgttcttca gtcctctgga    1320
ctttactctc tttcttctgt tgtgactgtg ccatcttctt cacttggaac tcagacttac    1380
atctgcaacg ttaaccacaa gccatccaac acaaaagtgg ataagaaggc agagccaaag    1440
tcctgtgata agactcatac ttgtccacca tgtccagctc agaacttct tggtggtcca     1500 tctgttttct tgtttccacc aaagccaaag gatactctca tgatttctag aactccagag    1560
gttacatgcg ttgtggttga tgtttctcat gaggatcctg aggttaagtt caactggtat    1620
gtggatggtg ttgaggttca caacgctaag actaagccaa gagaggaaca gtacaactct    1680
acttacaggg ttgtgtctgt gcttactgtg cttcatcagg attggcttaa cggcaaagag    1740
tacaagtgca aggtttccaa caaggctttg ccagctccaa tcgaaaagac tatttccaag    1800
gctaagggac aacctagaga gccacaagtt tacactcttc caccatctag ggaagagatg    1860
actaagaacc aggtttccct tacttgcctt gtgaagggat tctacccatc tgatattgct    1920
gttgagtggg agtctaatgg acagccagag aacaactaca agactactcc accagtgctt    1980
gattctgatg gctcattctt cttgtactcc aagctcactg tggataagtc aagatggcag    2040
cagggaaatg tgttctcttg ctctgttatg catgaggctc tccataatca ctacactcag    2100
aagtcccttt ctttgtctcc tggcaagtga                                      2130

<210> SEQ ID NO 4
<211> LENGTH: 2145
<212> TYPE: DNA
<213> ORGANISM: Artificial Sequence
<220> FEATURE:
<223> OTHER INFORMATION: anti-HIV PGT121 L-(KP6pp)-H construct

<400> SEQUENCE: 4
tctgatattt ctgttgctcc tggtgagact gctaggattt cttgtggtga aaagtctctg      60
ggttctaggg ctgttcaatg gtatcaacat agagctggtc aggctccatc tctgatcatc     120
tacaacaatc aggataggcc ttctggtatc cctgagaggt tttctggttc tcctgattct     180
cctttcggta ctactgctac ccttaccatt acttctgttg aggctggtga tgaggctgat     240
tactactgcc atatctggga ttcaaggggtg ccaactaagt gggttttcgg tggtggtact    300
actcttactg ttcttggtgc tgctgctggt caacctaagg ctgctccttc tgttactttg    360
ttccctccat cttctgagga actgcaagct aacaaggcta ctcttgtgtg cctgatctct    420 gattttacc ctggtgctgt tactgtggct tggaaggctg attcttcacc agttaaggct     480
ggtgtggaaa ctactactcc tagcaagcag agcaacaaca gtacgctgc ttcttcttac     540 ctgtctctta ctcctgaaca gtggaagtct cacaggtctt actcttgcca agttactcat    600
gagggtagca ctgtggaaaa gacagttgct cctactgaat gctctggtgg taagaggact    660
attcaggatt ctgctactga taccgtggat cttggagctg agcttcatag agatgatcct    720
ccacctaccg ctagcgatat tggtaaaagg ggtggtcaaa tgcagcttca agaatctggt    780
cctggtcttg ttaagccttc tgagactctt tctttgacct gctctgttag cggtgctagc    840
```

```
atctcagatt cttattggag ctggatcaga aggtcacctg gtaagggact tgagtggatt      900
ggttacgttc acaagtctgg tgataccaac tacagccctt cactgaagtc tagggtgaac      960 cttttctctgg atacctccaa gaatcaggtg tcccttctc ttgttgctgc tacagctgct     1020
gatagcggta agtattattg cgctaggact cttcacggta gaaggatcta tggtatcgtg     1080
gctttcaatg agtggttcac ctacttctac atggatgtgt ggggtaacgg tactcaggtt     1140
acagtttctt ctgcttctac taagggccca tctgtttttc cacttgctcc atcttccaag     1200
tctacttcag gtggaactgc tgctcttgga tgtcttgtta aggattactt cccagagcca     1260
gttactgtgt cttggaattc tggtgctctt acttctggtg ttcacacttt tccagctgtt     1320
cttcagtcct ctggacttta ctctctttct tctgttgtga ctgtgccatc ttcttcactt     1380
ggaactcaga cttacatctg caacgttaac cacaagccat ccaacacaaa agtggataag     1440
agggttgagc caaagtcctg tgataagact catacttgtc caccatgtcc agctccagaa     1500
cttcttggtg gtccatctgt tttcttgttt ccaccaaagc caaggatac tctcatgatt      1560 tccaggactc cagaggttac atgcgttgtg gttgatgttt ctcatgagga tcctgaggtt     1620
aagttcaact ggtatgtgga tggtgttgag gttcacaacg ctaagactaa gccaagagag     1680
gaacagtaca actctactta cagggttgtg tctgtgctta ctgtgcttca tcaggattgg     1740
cttaacggca agagtacaa gtgcaaggtt ccaacaagg ctttgccagc tccaatcgaa       1800
aagactattt ccaaggctaa gggacaacct agagagccac aagtttacac tcttccacca     1860
tctagggaag agatgactaa gaaccaggtt tcccttactt gccttgtgaa gggattctac     1920
ccatctgata ttgctgttga gtgggagtct aatggacagc cagagaacaa ctacaagact     1980
actccaccag tgcttgattc tgatggctca ttcttcttgt actccaagct cactgtggat     2040
aagtctagat ggcagcaggg aaatgtgttc tcttgctctg ttatgcatga ggctctccat     2100
aatcactaca ctcagaagtc cctttctttg tctcctggca agtga                    2145
```

<210> SEQ ID NO 5
<211> LENGTH: 2136
<212> TYPE: DNA
<213> ORGANISM: Artificial Sequence
<220> FEATURE:
<223> OTHER INFORMATION: secretory IgA construct Light chain - (KP6pp)-
      Heavy chain

<400> SEQUENCE: 5

```
gatattcttt tgactcagag ccctgctatc ctgtccgttt ctcctggtga gagggtttca       60
ttttcctgca gggcttctca gttcgtggga tcttctatcc actggtatca gcagaggacc      120
aacggttctc caaggctgct tatcaagtac gctagcgaga gcatgagcgg tatcccttct      180
aggtttagcg gttctggtag cggaaccgat ttcaccccttt ctatcaacac cgttgagagc     240
gaggatatcg ctgattacta ctgccagcag tctcactctt ggcctttcac tttcggtagc     300
ggtactaacc ttgaggtgaa gaggactgtt gctgctcctt ccgtgtttat cttcccacct     360
tctgatgagc agctgaagtc tggtactgct tctgtggtgt gcctgctgaa caatttctac    420
ccaagggaag ctaaggtgca gtggaaagtg ataacgctc tgcagtccgg taacagccaa      480
gagtctgtta ctgagcagga ttccaaggat agcacctaca gcctttcttc taccctgacc     540
ctgagcaagg ctgattacga gaagcacaag gtgtacgctt gcgaggttac acaccaggga     600
ctttcttcac ctgtgaccaa gtctttcaac aggggcgaat gcggaggcaa gaggaccatt     660
caggattctg ctaccgatac cgtggatctt ggtgctgagc ttcataggga tgatcctcca    720
```

-continued

```
cctaccgcta gcgatattgg taagaggggt ggtgaggtta agctggaaga atctggtggt      780
ggtcttgttc agcctggtgg tagcatgaag ctttcttgcg ttgcaagcgg tttcatcttc      840
agcaaccact ggatgaattg ggtgaggcag tctcctgaaa agggtcttga atgggtggca      900
gagatcaggt ccaagagcat taactctgct acccactacg ctgagtctgt aagggaagg       960 ttcaccatca gcagggatga tagcaagtct gctgtgtacc tgcagatgac cgatcttagg     1020
actgaggata ccggtgtgta ctactgctct aggaactact acggttccac ctacgattac     1080
tggggtcagg gaactaccct taccgtgtca tctgcttctc aacctctcc taaggtgttc      1140 cctctgtctc ttgatagcac tcctcaggat ggtaatgtgg ttgtggcttg ccttgtgcag     1200
ggattctttc acaagagcc tttgtctgtg acctggtctg agtctggtca gaatgtgact      1260
gctaggaact ccccaccaag ccaggatgct caggtgatc tttacaccac ctcttctcag      1320
cttacccttc ctgctactca gtgccctgat ggtaagtctg tgacttgcca tgtgaagcac     1380
tacaccaacc catctcagga tgttactgtt ccttgcccag ttcctcctcc tccaccatgt     1440
tgtcatccaa ggttgtctct tcacaggcct gctcttgagg atcttctgct tggatctgag     1500
gctaacctta cctgcactct taccggtctt agggatgcta gtggtgctac ttttacctgg     1560
accccaagct ctggtaagtc agctgttcaa ggtcctcctg agagagatct ttgcggttgc     1620
tactccgttt cttctgtgct tcctggttgt gctcagccat ggaatcatgg tgagactttc     1680
acttgcactg ctgctcaccc tgagcttaag actcctctta ccgctaacat caccaagagc     1740
ggtaatacct tcaggccaga ggttcacctt cttccacctc catctgagga acttgctctt     1800
aacgagcttg tgaccttgac ctgccttgct aggggtttca gtccaaagga tgtgcttgtg     1860
agatggctgc agggatctca agaactgcct agagagaagt acctgacctg ggcttctagg     1920 caagaaccttt ctcagggtac tactaccttc gctgtgacct ctattcttag ggtggcagct     1980
gaggattgga aaagggtga taccttctcc tgcatggtgg tcatgaggc tttgcctctt     2040 gctttcaccc aaaagaccat cgataggctg gctggtaagc ctacccatgt gaatgtgtct     2100
gtggtgatgg ctgaagtgga tggaacatgc tactga                                2136
```

<210> SEQ ID NO 6
<211> LENGTH: 2280
<212> TYPE: DNA
<213> ORGANISM: Artificial Sequence
<220> FEATURE:
<223> OTHER INFORMATION: ecretory IgA construct J chain-(KP6pp)-
      secretory component

<400> SEQUENCE: 6

```
caagaagatg agaggatcgt tctggtggat aacaagtgca agtgcgctag gatcaccagc       60
aggatcatta ggtcaagcga ggatcctaac gaggatatcg ttgagaggaa catcaggatc      120
atcgtgcctc tgaacaacag agagaatatc agcgatccta ccagccctct gaggaccaga      180
ttcgtgtacc acctttctga tctgtgcaag aagtgcgatc caaccgaggt tgagctggat      240
aaccagattg tgactgctac ccagagcaac atctgtgatg aggattctgc taccgagact      300
tgctacacct acgataggaa caagtgctac actgctgtgg tgcctcttgt ttacggtggt      360
gagactaaga tggtggaaac cgctcttact cctgatgctt gctatcctga tggtggtaag      420
aggaccatcc aggattcagc tactgatacc gtggatcttg tgctgagct tcacagagat      480 gatcctccac ctaccgctag cgatattggt aagagaggtg gtaagagtcc tatttttggt      540
cctgaagagg tgaacagcgt tgagggaaac tctgtgtcta ttacctgcta ctaccctcct      600
```

```
acctctgtga acaggcacac cagaaagtat tggtgcagac aaggtgctag gggaggttgt    660
attaccctga tcagcagcga gggttacgtg tcctctaagt atgctggtag ggctaacctg    720
accaacttcc ctgagaatgg tactttcgtg gtgaacattg ctcagctgtc ccaggatgat    780
agcggtaggt ataagtgcgg tctgggtatc aactctaggg gtctgagctt cgatgtgagc    840
cttgaagttt ctcagggtcc tggtctgctg aacgatacca aggtttacac cgtggatctt    900
ggtaggaccg tgaccattaa ctgccctttc aagactgaga acgctcagaa gaggaagtcc    960
ctgtacaagc agattggtct gtaccctgtg ctggtgatcg atagctctgg ttacgtgaac   1020
cctaactaca ccggtaggat caggcttgat attcagggaa ccggtcagct gcttttcagc   1080
gtggtgatta ccagctgag gctgtctgat gctggtcagt atctttgtca ggctggtgat   1140
gattccaaca gcaacaagaa gaacgctgat cttcaggtgc tgaagcctga gcctgagctt   1200
gtttatgagg atctgagggg ttctgtgacc ttccattgtg ctcttggacc tgaggttgca   1260
aacgtggcaa agttcttgtg caggcagtca agcggtgaga actgtgatgt ggtggtgaac   1320
actcttggta agagggctcc tgcttcgag ggtaggattc ttcttaaccc tcaggataag   1380
gatggtagct ctccgtggt gattaccggt ctgagaaaag aggatgctgg tagataccctt   1440 tgcggtgctc attctgatgg tcagctgcaa gagggttctc ctattcaagc ttggcagctg   1500
ttcgtgaacg aagagtctac cattccaagg tcacctaccg ttgttaaggg tgtggctggt   1560
tcttctgtgg ctgttctttg cccttacaat aggaaagaga gcaagagcat caagtactgg   1620
tgcctttggg agggtgctca gaatggtaga tgccctcttt tggtggattc tgagggttgg   1680
gttaaggctc agtatgaggg taggcttagc ctgcttgagg aacctggtaa cggtactttc   1740
accgtgattc tgaaccagct gacctctagg gatgctggtt tctactggtg cttgaccaac   1800
ggtgatactc tttggaggac caccgttgag atcaagatca ttgagggtga gcctaacctg   1860
aaggtgccag gtaatgttac tgctgtgctt ggtgagactc tgaaagtgcc ttgccatttc   1920
ccttgcaagt tcagcagcta cgagaagtac tggtgtaagt ggaacaatac cggttgccag   1980
gctctgcctt ctcaagatga aggaccttct aaggctttcg tgaactgtga tgagaacagc   2040
aggcttgtgt ctctgaccct taatcttgtg accaggcctg atgagggatg gtattggtgt   2100
ggtgttaagc agggacactt ctacggtgag actgctgctg tttatgtggc tgtggaagag   2160
agaaaggctg ctggttctag ggatgtgtct ctggctaagg ctgatgctgc tcctgatgag   2220
aaggtgctgg attctggttt cagagagatc gagaacaagg ctatccagga tccaaggtga   2280
```

<210> SEQ ID NO 7
<211> LENGTH: 2511
<212> TYPE: DNA
<213> ORGANISM: Artificial Sequence
<220> FEATURE:
<223> OTHER INFORMATION: secretory IgA construct Light chain-(KP6pp)-
      secretory component

<400> SEQUENCE: 7

```
gatattcttc ttactcagag ccctgctatc ctgtccgttt ctcctggtga gagggtttca     60
ttttcctgca gggcttctca gttcgtggga tcttctatcc actggtatca gcagaggacc    120
aacggttctc ctaggctgct tatcaagtac gctagcgaga gcatgagcgg tatccctctt    180
aggtttagcg gttctggtag cggaaccgat ttcacccttt ctatcaacac cgttgagagc    240
gaggatatcg ctgattacta ctgccagcag tctcactctt ggccttttcac tttcggtagc    300 ggtactaacc ttgaggtgaa gaggactgtt gctgctcctt ccgtgttcat cttcccacca    360
```

```
tctgatgagc agctgaagtc tggtactgct tctgtggtgt gcttactgaa caatttctac    420
cctagggaag ctaaggtgca gtggaaagtg gataacgctc tgcagtccgg taacagccaa    480
gagtctgtta ctgagcagga tagcaaggat tccacctaca gcctttcttc taccctgacc    540
ctgagcaagg ctgattacga gaagcacaag gtgtacgctt gcgaggttac acaccaggga    600
ctttcttcac ctgtgaccaa gtctttcaac aggggagaat gcggaggtaa gaggaccatt    660
caggattctg ctaccgatac cgtggatctt ggtgctgagc ttcatagggg tgatcctcca    720
cctaccgcta gcgatattgg taagagaggt ggtaagagtc ctattttggg tcctgaagag    780
gtgaacagcg ttgagggaaa ctctgtgtct attaccctgc tactaccctcc tacctctgtg    840
aacaggcaca ccagaaagta ttggtgcaga caaggtgcta ggggaggttg tattaccctg    900
atcagcagcg agggttacgt gtcctctaag tatgctggta gggctaaccct gaccaacttc    960
cctgagaatg gtactttcgt ggtgaacatt gctcagctgt cccaggatga tagcggtagg   1020
tataagtgcg gtctgggtat caactctagg ggtctgagct tcgatgtgag ccttgaagtt   1080
tctcagggtc ctggtctgct gaacgatacc aaggtttaca ccgtggatct tggtaggacc   1140
gtgaccatta actgccccttt caagactgag aacgctcaga gaggaagtc cctgtacaag   1200
cagattggtc tgtaccctgt gctggtgatc gatagctctg ttacgtgaa ccctaactac   1260
accggtagga tcaggcttga tattcaggga accggtcagc tgcttttcag cgtggtgatt   1320
aaccagctga ggctgtctga tgctggtcag tatctttgtc aggctggtga tgattccaac   1380
agcaacaaga gaacgctga tcttcaggtg ctgaagcctg agcctgagct tgtttatgag   1440
gatctgaggg gttctgtgac cttccattgt gctcttggac ctgaggttgc aaacgtggca   1500
aagttcttgt gcaggcagtc aagcggtgag aactgtgatg tggtggtgaa cactcttggt   1560
aagagggctc ctgctttcga gggtaggatt cttcttaacc ctcaggataa ggatggtagc   1620
ttctccgtgg tgattaccgg tctgagaaaa gaggatgctg gtagatacct ttgcggtgct   1680
cattctgatg tcagctgca agagggttct cctattcaag cttggcagct gttcgtgaac   1740
gaagagtcta ccattccaag gtcacctacc gttgttaagg gtgtggctgg ttcttctgtg   1800
gctgttcttt gcccttacaa taggaaagag agcaagagca tcaagtactg gtgcctttgg   1860
gagggtgctc agaatggtag atgccctctt ttggtggatt ctgagggttg ggttaaggct   1920
cagtatgagg gtaggcttag cctgcttgag gaacctggta acggtacttt caccgtgatt   1980
ctgaaccagc tgacctctag ggatgctggt ttctactggt gcttgaccaa cggtgatact   2040
ctttggagga ccaccgttga gatcaagatc attgagggtg agcctaacct gaaggtgcca   2100
ggtaatgtta ctgctgtgct tggtgagact ctgaaagtgc cttgccattt cccttgcaag   2160
ttcagcagct acgagaagta ctggtgtaag tggaacaata ccggttgcca ggctctgcct   2220
tctcaagatg aaggaccttc taaggctttc gtgaactgtg atgagaacag caggcttgtg   2280
tctctgaccc ttaatcttgt gaccagggct gatgagggat ggtattggtg tggtgttaag   2340
cagggacact tctacggtga gactgctgct gtttatgtgg ctgtggaaga gagaaaggct   2400
gctggttcta gggatgtgtc tctggctaag gctgatgctg ctcctgatga aggtgctg    2460
gattctggtt tcagagagat cgagaacaag gctatccagg atccaaggtg a          2511
```

<210> SEQ ID NO 8
<211> LENGTH: 1905
<212> TYPE: DNA
<213> ORGANISM: Artificial Sequence
<220> FEATURE:
<223> OTHER INFORMATION: secretory IgA construct Heavy chain-(KP6pp)-J

```
<400> SEQUENCE: 8
gaagttaagc ttgaagaatc tggtggtggt ctggttcagc ctggtggttc tatgaagctt      60
tcttgcgtgg caagcggttt catcttcagc aaccattgga tgaactgggt gaggcagtct     120
cctgaaaagg gtcttgaatg ggtggcagag atcaggtcca agagcattaa ctctgctacc     180
cactacgctg agtctgtgaa gggaaggttc accatcagca gggatgatag caagtctgct     240
gtgtacctgc agatgaccga tcttaggact gaggataccg gtgtgtacta ctgctctagg     300
aactactacg gtagcaccta cgattactgg ggtcagggaa ctacccttac cgtgtcatct     360
gcttctccaa cctctcctaa ggtgttccct ctgtctcttg atagcactcc tcaggatggt     420
aatgtggtgg ttgcttgcct tgtgcaggga ttctttccac aagagccttt gtctgtgacc     480
tggtctgagt ctggtcagaa tgtgactgct aggaacttcc cacctagcca ggatgcttca     540
ggtgatcttt acaccacctc ttctcagctt acccttcctg ctactcagtg ccctgatggt     600
aagtctgtta cctgccatgt gaagcactac accaaccctt cacaggatgt tactgtgcct     660
tgccctgttc ctcctcctcc accttgttgt catccaaggt gtctcttca caggcctgct      720
cttgaggatc ttctgcttgg atctgaggct aaccttacct gcactcttac cggtcttagg     780
gatgcttctg gtgctacttt tacctggacc ccaagctctg gtaagtctgc tgttcaaggt     840
cctcctgaga gatctttg cggttgctac tccgtttctt ctgtgcttcc tggttgtgct       900
cagccttgga atcatggtga ctttcact tgcactgctg ctcaccctga gcttaagact        960
cctcttaccg ctaacatcac caagagcggt aatacctcc gtcctgaggt tcaccttctt      1020
ccacctccat ctgaggaact tgctcttaac gagcttgtga cccttacctg ccttgctagg     1080
ggtttcagtc ctaaggatgt gcttgtgaga tggctgcagg ttctcaaga actgcctaga     1140
gagaagtacc tgacctgggc ttctagacaa gaaccttctc agggtactac caccttcgct     1200
gtgacctcta ttcttagagt ggctgctgag gattggaaga agggtgatac cttctcttgc     1260
atggtgggtc atgaggcttt gcctcttgct ttcacccaaa agaccatcga taggctggct     1320
ggtaagccta cccatgtgaa tgtttctgtg tgatggctg aagtggatgg aacttgctat      1380
ggtggtaaga ggaccatcca ggattctgct actgataccg tggatcttgg tgctgagctt     1440
cacagagatg atcctccacc taccgctagc gatattggta agaggggtgg tcaagaggat     1500
gagaggattg tgctggtgga taacaagtgc aagtgcgcta ggatcaccag caggatcatt     1560
aggtcaagcg aggatcctaa cgaggatatc gttgagagga acatcaggat catcgtgcct     1620
ctgaacaaca gagagaatat cagcgatcct accagccctc tgaggaccag attcgtgtac     1680
cacctttctg atctgtgcaa gaagtgcgat cctaccgagg ttgagctgga taaccagatt     1740
gtgactgcta cccagagcaa catctgtgat gaggattcag ctaccgagac ttgctacacc     1800
tacgatagga caagtgcta cactgctgtg gtgcctcttg tttacggtgg tgagactaag      1860
atggtggaaa ccgctcttac tcctgatgct tgctaccctg attga                     1905

<210> SEQ ID NO 9
<211> LENGTH: 111
<212> TYPE: DNA
<213> ORGANISM: Artificial Sequence
<220> FEATURE:
<223> OTHER INFORMATION: KP6pp linking polypeptide

<400> SEQUENCE: 9
ggaggtaaga ggactattca agattccgct actgatactg tggatcttgg agctgagctt      60
```
catagagatg atccaccacc aactgcttcc gatattggaa agagaggtgg a    111

<210> SEQ ID NO 10
<211> LENGTH: 698
<212> TYPE: PRT
<213> ORGANISM: Artificial Sequence
<220> FEATURE:
<223> OTHER INFORMATION: VRC01 L-(KP6pp)-H construct

<400> SEQUENCE: 10

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Arg Ser Pro Val Thr Lys Ser Phe Asn Arg Gly
        195                 200                 205

Glu Cys Gly Gly Lys Arg Thr Ile Gln Asp Ser Ala Thr Asp Thr Val
    210                 215                 220

Asp Leu Gly Ala Glu Leu His Arg Asp Asp Pro Pro Thr Ala Ser
225                 230                 235                 240

Asp Ile Gly Lys Arg Gly Gly Gln Val Gln Leu Val Gln Ser Gly Gly
                245                 250                 255

Gln Met Lys Lys Pro Gly Glu Ser Met Arg Ile Ser Cys Arg Ala Ser
            260                 265                 270

Gly Tyr Glu Phe Ile Asp Cys Thr Leu Asn Trp Ile Arg Leu Ala Pro
        275                 280                 285

Gly Lys Arg Pro Glu Trp Met Gly Trp Leu Lys Pro Arg Gly Gly Ala
    290                 295                 300

Val Asn Tyr Ala Arg Pro Leu Gln Gly Arg Val Thr Met Thr Arg Asp
305                 310                 315                 320

Val Tyr Ser Asp Thr Ala Phe Leu Glu Leu Arg Ser Leu Thr Val Asp
                325                 330                 335

Asp Thr Ala Val Tyr Phe Cys Thr Arg Gly Lys Asn Cys Asp Tyr Asn
            340                 345                 350

```
Trp Asp Phe Glu His Trp Gly Arg Gly Thr Pro Val Ile Val Ser Ser
            355                 360                 365
Pro Ser Thr Lys Gly Pro Ser Val Phe Pro Leu Ala Pro Ser Ser Lys
        370                 375                 380
Ser Thr Ser Gly Gly Thr Ala Ala Leu Gly Cys Leu Val Lys Asp Tyr
385                 390                 395                 400
Phe Pro Glu Pro Val Thr Val Ser Trp Asn Ser Gly Ala Leu Thr Ser
                405                 410                 415
Gly Val His Thr Phe Pro Ala Val Leu Gln Ser Ser Gly Leu Tyr Ser
            420                 425                 430
Leu Ser Ser Val Val Thr Val Pro Ser Ser Ser Leu Gly Thr Gln Thr
        435                 440                 445
Tyr Ile Cys Asn Val Asn His Lys Pro Ser Asn Thr Lys Val Asp Lys
    450                 455                 460
Lys Ala Glu Pro Lys Ser Cys Asp Lys Thr His Thr Cys Pro Pro Cys
465                 470                 475                 480
Pro Ala Pro Glu Leu Leu Gly Gly Pro Ser Val Phe Leu Phe Pro Pro
                485                 490                 495
Lys Pro Lys Asp Thr Leu Met Ile Ser Arg Thr Pro Glu Val Thr Cys
            500                 505                 510
Val Val Val Asp Val Ser His Glu Asp Pro Glu Val Lys Phe Asn Trp
        515                 520                 525
Tyr Val Asp Gly Val Glu Val His Asn Ala Lys Thr Lys Pro Arg Glu
    530                 535                 540
Glu Gln Tyr Asn Ser Thr Tyr Arg Val Val Ser Val Leu Thr Val Leu
545                 550                 555                 560
His Gln Asp Trp Leu Asn Gly Lys Glu Tyr Lys Cys Lys Val Ser Asn
                565                 570                 575
Lys Ala Leu Pro Ala Pro Ile Glu Lys Thr Ile Ser Lys Ala Lys Gly
            580                 585                 590
Gln Pro Arg Glu Pro Gln Val Tyr Thr Leu Pro Pro Ser Arg Glu Glu
        595                 600                 605
Met Thr Lys Asn Gln Val Ser Leu Thr Cys Leu Val Lys Gly Phe Tyr
    610                 615                 620
Pro Ser Asp Ile Ala Val Glu Trp Glu Ser Asn Gly Gln Pro Glu Asn
625                 630                 635                 640
Asn Tyr Lys Thr Thr Pro Pro Val Leu Asp Ser Asp Gly Ser Phe Phe
                645                 650                 655
Leu Tyr Ser Lys Leu Thr Val Asp Lys Ser Arg Trp Gln Gln Gly Asn
            660                 665                 670
Val Phe Ser Cys Ser Val Met His Glu Ala Leu His Asn His Tyr Thr
        675                 680                 685
Gln Lys Ser Leu Ser Leu Ser Pro Gly Lys
    690                 695

<210> SEQ ID NO 11
<211> LENGTH: 698
<212> TYPE: PRT
<213> ORGANISM: Artificial Sequence
<220> FEATURE:
<223> OTHER INFORMATION: VRC01 H-(KP6pp)-L construct

<400> SEQUENCE: 11

Gln Val Gln Leu Val Gln Ser Gly Gly Gln Met Lys Lys Pro Gly Glu
1               5                   10                  15
```

```
Ser Met Arg Ile Ser Cys Arg Ala Ser Gly Tyr Glu Phe Ile Asp Cys
         20                  25                  30

Thr Leu Asn Trp Ile Arg Leu Ala Pro Gly Lys Arg Pro Glu Trp Met
             35                  40                  45

Gly Trp Leu Lys Pro Arg Gly Gly Ala Val Asn Tyr Ala Arg Pro Leu
         50                  55                  60

Gln Gly Arg Val Thr Met Thr Arg Asp Val Tyr Ser Asp Thr Ala Phe
 65                  70                  75                  80

Leu Glu Leu Arg Ser Leu Thr Val Asp Asp Thr Ala Val Tyr Phe Cys
                 85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser Pro Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Ala Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
```

```
            435                 440                 445
Pro Gly Lys Gly Gly Lys Arg Thr Ile Gln Asp Ser Ala Thr Asp Thr
        450                 455                 460
Val Asp Leu Gly Ala Glu Leu His Arg Asp Asp Pro Pro Thr Ala
465                 470                 475                 480
Ser Asp Ile Gly Lys Arg Gly Gly Glu Ile Val Leu Thr Gln Ser Pro
                485                 490                 495
Gly Thr Leu Ser Leu Ser Pro Gly Glu Thr Ala Ile Ile Ser Cys Arg
            500                 505                 510
Thr Ser Gln Tyr Gly Ser Leu Ala Trp Tyr Gln Gln Arg Pro Gly Gln
        515                 520                 525
Ala Pro Arg Leu Val Ile Tyr Ser Gly Ser Thr Arg Ala Ala Gly Ile
530                 535                 540
Pro Asp Arg Phe Ser Gly Ser Arg Trp Gly Pro Asp Tyr Asn Leu Thr
545                 550                 555                 560
Ile Ser Asn Leu Glu Ser Gly Asp Phe Gly Val Tyr Tyr Cys Gln Gln
                565                 570                 575
Tyr Glu Phe Phe Gly Gln Gly Thr Lys Val Gln Val Asp Ile Lys Arg
            580                 585                 590
Thr Val Ala Ala Pro Ser Val Phe Ile Phe Pro Pro Ser Asp Glu Gln
        595                 600                 605
Leu Lys Ser Gly Thr Ala Ser Val Val Cys Leu Leu Asn Asn Phe Tyr
610                 615                 620
Pro Arg Glu Ala Lys Val Gln Trp Lys Val Asp Asn Ala Leu Gln Ser
625                 630                 635                 640
Gly Asn Ser Gln Glu Ser Val Thr Glu Gln Asp Ser Lys Asp Ser Thr
                645                 650                 655
Tyr Ser Leu Ser Ser Thr Leu Thr Leu Ser Lys Ala Asp Tyr Glu Lys
            660                 665                 670
His Lys Val Tyr Ala Cys Glu Val Thr His Gln Gly Leu Arg Ser Pro
        675                 680                 685
Val Thr Lys Ser Phe Asn Arg Gly Glu Cys
    690                 695

<210> SEQ ID NO 12
<211> LENGTH: 709
<212> TYPE: PRT
<213> ORGANISM: Artificial Sequence
<220> FEATURE:
<223> OTHER INFORMATION: anti-influenza CR6261 L-(KP6pp)-H construct

<400> SEQUENCE: 12

Gln Ser Val Leu Thr Gln Pro Pro Ser Val Ser Ala Ala Pro Gly Gln
1               5                   10                  15
Lys Val Thr Ile Ser Cys Ser Gly Ser Ser Ser Asn Ile Gly Asn Asp
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Asn Tyr Tyr Cys Ala Thr Trp Asp Arg Arg Pro
                85                  90                  95
Thr Ala Tyr Val Val Phe Gly Gly Gly Thr Lys Leu Thr Val Leu Gly
```

-continued

```
                100             105             110
    Ala Ala Ala Gly Gln Pro Lys Ala Ala Pro Ser Val Thr Leu Phe Pro
                115             120             125
    Pro Ser Ser Glu Glu Leu Gln Ala Asn Lys Ala Thr Leu Val Cys Leu
                130             135             140
    Ile Ser Asp Phe Tyr Pro Gly Ala Val Thr Val Ala Trp Lys Ala Asp
    145             150             155             160
    Ser Ser Pro Val Lys Ala Gly Val Glu Thr Thr Thr Pro Ser Lys Gln
                    165             170             175
    Ser Asn Asn Lys Tyr Ala Ala Ser Ser Tyr Leu Ser Leu Thr Pro Glu
                    180             185             190
    Gln Trp Lys Ser His Arg Ser Tyr Ser Cys Gln Val Thr His Glu Gly
                195             200             205
    Ser Thr Val Glu Lys Thr Val Ala Pro Thr Glu Cys Ser Gly Gly Lys
                210             215             220
    Arg Thr Leu Gln Asp Ser Ala Thr Asp Thr Val Asp Leu Gly Ala Glu
    225             230             235             240
    Leu His Arg Asp Asp Pro Pro Thr Ala Ser Asp Ile Gly Lys Arg
                    245             250             255
    Gly Gly Glu Val Gln Leu Val Glu Ser Gly Ala Glu Val Lys Lys Pro
                    260             265             270
    Gly Ser Ser Val Lys Val Ser Cys Lys Ala Ser Gly Gly Pro Phe Arg
                    275             280             285
    Ser Tyr Ala Ile Ser Trp Val Arg Gln Ala Pro Gly Gln Gly Pro Glu
                290             295             300
    Trp Met Gly Gly Ile Ile Pro Ile Phe Gly Thr Thr Lys Tyr Ala Pro
    305             310             315             320
    Lys Phe Gln Gly Arg Val Thr Ile Thr Ala Asp Asp Phe Ala Gly Thr
                    325             330             335
    Val Tyr Met Glu Leu Ser Ser Leu Arg Ser Glu Asp Thr Ala Met Tyr
                340             345             350
    Tyr Cys Ala Lys His Met Gly Tyr Gln Val Arg Glu Thr Met Asp Val
                    355             360             365
    Trp Gly Lys Gly Thr Thr Val Thr Val Ser Ser Ala Ser Thr Lys Gly
                    370             375             380
    Pro Ser Val Phe Pro Leu Ala Pro Ser Ser Lys Ser Thr Ser Gly Gly
    385             390             395             400
    Thr Ala Ala Leu Gly Cys Leu Val Lys Asp Tyr Phe Pro Glu Pro Val
                    405             410             415
    Thr Val Ser Trp Asn Ser Gly Ala Leu Thr Ser Gly Val His Thr Phe
                    420             425             430
    Pro Ala Val Leu Gln Ser Ser Gly Leu Tyr Ser Leu Ser Ser Val Val
                435             440             445
    Thr Val Pro Ser Ser Ser Leu Gly Thr Gln Thr Tyr Ile Cys Asn Val
                    450             455             460
    Asn His Lys Pro Ser Asn Thr Lys Val Asp Lys Lys Ala Glu Pro Lys
    465             470             475             480
    Ser Cys Asp Lys Thr His Thr Cys Pro Pro Cys Pro Ala Pro Glu Leu
                    485             490             495
    Leu Gly Gly Pro Ser Val Phe Leu Phe Pro Pro Lys Pro Lys Asp Thr
                    500             505             510
    Leu Met Ile Ser Arg Thr Pro Glu Val Thr Cys Val Val Val Asp Val
                    515             520             525
```

Ser His Glu Asp Pro Glu Val Lys Phe Asn Trp Tyr Val Asp Gly Val
    530                 535                 540

Glu Val His Asn Ala Lys Thr Lys Pro Arg Glu Glu Gln Tyr Asn Ser
545                 550                 555                 560

Thr Tyr Arg Val Val Ser Val Leu Thr Val Leu His Gln Asp Trp Leu
            565                 570                 575

Asn Gly Lys Glu Tyr Lys Cys Lys Val Ser Asn Lys Ala Leu Pro Ala
        580                 585                 590

Pro Ile Glu Lys Thr Ile Ser Lys Ala Lys Gly Gln Pro Arg Glu Pro
    595                 600                 605

Gln Val Tyr Thr Leu Pro Pro Ser Arg Glu Glu Met Thr Lys Asn Gln
610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
            645                 650                 655

Pro Pro Val Leu Asp Ser Asp Gly Ser Phe Phe Leu Tyr Ser Lys Leu
        660                 665                 670

Thr Val Asp Lys Ser Arg Trp Gln Gln Gly Asn Val Phe Ser Cys Ser
    675                 680                 685

Val Met His Glu Ala Leu His Asn His Tyr Thr Gln Lys Ser Leu Ser
690                 695                 700

Leu Ser Pro Gly Lys
705

<210> SEQ ID NO 13
<211> LENGTH: 714
<212> TYPE: PRT
<213> ORGANISM: Artificial Sequence
<220> FEATURE:
<223> OTHER INFORMATION: anti-HIV PGT121 L-(KP6pp)-H construct

<400> SEQUENCE: 13

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Pro Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly Ala Ala Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

```
Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser Gly Gly Lys Arg Thr Ile Gln Asp Ser
210                 215                 220

Ala Thr Asp Thr Val Asp Leu Gly Ala Glu Leu His Arg Asp Asp Pro
225                 230                 235                 240

Pro Pro Thr Ala Ser Asp Ile Gly Lys Arg Gly Gln Met Gln Leu
                245                 250                 255

Gln Glu Ser Gly Pro Gly Leu Val Lys Pro Ser Glu Thr Leu Ser Leu
            260                 265                 270

Thr Cys Ser Val Ser Gly Ala Ser Ile Ser Asp Ser Tyr Trp Ser Trp
        275                 280                 285

Ile Arg Arg Ser Pro Gly Lys Gly Leu Glu Trp Ile Gly Tyr Val His
    290                 295                 300

Lys Ser Gly Asp Thr Asn Tyr Ser Pro Ser Leu Lys Ser Arg Val Asn
305                 310                 315                 320

Leu Ser Leu Asp Thr Ser Lys Asn Gln Val Ser Leu Ser Leu Val Ala
                325                 330                 335

Ala Thr Ala Ala Asp Ser Gly Lys Tyr Tyr Cys Ala Arg Thr Leu His
            340                 345                 350

Gly Arg Arg Ile Tyr Gly Ile Val Ala Phe Asn Glu Trp Phe Thr Tyr
        355                 360                 365

Phe Tyr Met Asp Val Trp Gly Asn Gly Thr Gln Val Thr Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Arg Val Glu Pro Lys Ser Cys Asp Lys Thr His Thr Cys Pro Pro Cys
                485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590
```

```
Lys Ala Leu Pro Ala Pro Ile Glu Lys Thr Ile Ser Lys Ala Lys Gly
            595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
            645                 650                 655

Asn Tyr Lys Thr Thr Pro Pro Val Leu Asp Ser Asp Gly Ser Phe Phe
        660                 665                 670

Leu Tyr Ser Lys Leu Thr Val Asp Lys Ser Arg Trp Gln Gln Gly Asn
    675                 680                 685

Val Phe Ser Cys Ser Val Met His Glu Ala Leu His Asn His Tyr Thr
690                 695                 700

Gln Lys Ser Leu Ser Leu Ser Pro Gly Lys
705                 710

<210> SEQ ID NO 14
<211> LENGTH: 711
<212> TYPE: PRT
<213> ORGANISM: Artificial Sequence
<220> FEATURE:
<223> OTHER INFORMATION: secretory IgA construct Light chain-(KP6pp)-
      Heavy chain

<400> SEQUENCE: 14

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Lys Arg Thr Ile Gln Asp Ser Ala
    210                 215                 220

Thr Asp Thr Val Asp Leu Gly Ala Glu Leu His Arg Asp Asp Pro Pro
225                 230                 235                 240
```

```
Pro Thr Ala Ser Asp Ile Gly Lys Arg Gly Glu Val Lys Leu Glu
            245                 250                 255

Glu Ser Gly Gly Gly Leu Val Gln Pro Gly Gly Ser Met Lys Leu Ser
            260                 265                 270

Cys Val Ala Ser Gly Phe Ile Phe Ser Asn His Trp Met Asn Trp Val
            275                 280                 285

Arg Gln Ser Pro Glu Lys Gly Leu Glu Trp Val Ala Glu Ile Arg Ser
            290                 295                 300

Lys Ser Ile Asn Ser Ala Thr His Tyr Ala Glu Ser Val Lys Gly Arg
305                 310                 315                 320

Phe Thr Ile Ser Arg Asp Asp Ser Lys Ser Ala Val Tyr Leu Gln Met
                325                 330                 335

Thr Asp Leu Arg Thr Glu Asp Thr Gly Val Tyr Tyr Cys Ser Arg Asn
                340                 345                 350

Tyr Tyr Gly Ser Thr Tyr Asp Tyr Trp Gly Gln Gly Thr Thr Leu Thr
                355                 360                 365

Val Ser Ser Ala Ser Pro Thr Ser Pro Lys Val Phe Pro Leu Ser Leu
            370                 375                 380

Asp Ser Thr Pro Gln Asp Gly Asn Val Val Ala Cys Leu Val Gln
385                 390                 395                 400

Gly Phe Phe Pro Gln Glu Pro Leu Ser Val Thr Trp Ser Glu Ser Gly
                405                 410                 415

Gln Asn Val Thr Ala Arg Asn Phe Pro Pro Ser Gln Asp Ala Ser Gly
            420                 425                 430

Asp Leu Tyr Thr Thr Ser Ser Gln Leu Thr Leu Pro Ala Thr Gln Cys
            435                 440                 445

Pro Asp Gly Lys Ser Val Thr Cys His Val Lys His Tyr Thr Asn Pro
450                 455                 460

Ser Gln Asp Val Thr Val Pro Cys Pro Val Pro Pro Pro Pro Cys
465                 470                 475                 480

Cys His Pro Arg Leu Ser Leu His Arg Pro Ala Leu Glu Asp Leu Leu
                485                 490                 495

Leu Gly Ser Glu Ala Asn Leu Thr Cys Thr Leu Thr Gly Leu Arg Asp
            500                 505                 510

Ala Ser Gly Ala Thr Phe Thr Trp Thr Pro Ser Ser Gly Lys Ser Ala
            515                 520                 525

Val Gln Gly Pro Pro Glu Arg Asp Leu Cys Gly Cys Tyr Ser Val Ser
            530                 535                 540

Ser Val Leu Pro Gly Cys Ala Gln Pro Trp Asn His Gly Glu Thr Phe
545                 550                 555                 560

Thr Cys Thr Ala Ala His Pro Glu Leu Lys Thr Pro Leu Thr Ala Asn
                565                 570                 575

Ile Thr Lys Ser Gly Asn Thr Phe Arg Pro Glu Val His Leu Leu Pro
                580                 585                 590

Pro Pro Ser Glu Glu Leu Ala Leu Asn Glu Leu Val Thr Leu Thr Cys
            595                 600                 605

Leu Ala Arg Gly Phe Ser Pro Lys Asp Val Leu Val Arg Trp Leu Gln
            610                 615                 620

Gly Ser Gln Glu Leu Pro Arg Glu Lys Tyr Leu Thr Trp Ala Ser Arg
625                 630                 635                 640

Gln Glu Pro Ser Gln Gly Thr Thr Thr Phe Ala Val Thr Ser Ile Leu
                645                 650                 655
```

```
Arg Val Ala Ala Glu Asp Trp Lys Lys Gly Asp Thr Phe Ser Cys Met
                660                 665                 670

Val Gly His Glu Ala Leu Pro Leu Ala Phe Thr Gln Lys Thr Ile Asp
                675                 680                 685

Arg Leu Ala Gly Lys Pro Thr His Val Asn Val Ser Val Val Met Ala
                690                 695                 700

Glu Val Asp Gly Thr Cys Tyr
705                 710

<210> SEQ ID NO 15
<211> LENGTH: 759
<212> TYPE: PRT
<213> ORGANISM: Artificial Sequence
<220> FEATURE:
<223> OTHER INFORMATION: secretory IgA construct J chain-(KP6pp)-
      secretory component

<400> SEQUENCE: 15

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
                20                  25                  30

Ile Val Glu Arg Asn Ile Arg Ile Ile Val Pro Leu Asn Asn Arg Glu
                35                  40                  45

Asn Ile Ser Asp Pro Thr Ser Pro Leu Arg Thr Arg Phe Val Tyr His
                50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
                100                 105                 110

Val Val Pro Leu Val Tyr Gly Gly Glu Thr Lys Met Val Glu Thr Ala
                115                 120                 125

Leu Thr Pro Asp Ala Cys Tyr Pro Asp Gly Gly Lys Arg Thr Ile Gln
            130                 135                 140

Asp Ser Ala Thr Asp Thr Val Asp Leu Gly Ala Glu Leu His Arg Asp
145                 150                 155                 160

Asp Pro Pro Pro Thr Ala Ser Asp Ile Gly Lys Arg Gly Gly Lys Ser
                165                 170                 175

Pro Ile Phe Gly Pro Glu Glu Val Asn Ser Val Glu Gly Asn Ser Val
                180                 185                 190

Ser Ile Thr Cys Tyr Tyr Pro Pro Thr Ser Val Asn Arg His Thr Arg
                195                 200                 205

Lys Tyr Trp Cys Arg Gln Gly Ala Arg Gly Gly Cys Ile Thr Leu Ile
            210                 215                 220

Ser Ser Glu Gly Tyr Val Ser Ser Lys Tyr Ala Gly Arg Ala Asn Leu
225                 230                 235                 240

Thr Asn Phe Pro Glu Asn Gly Thr Phe Val Val Asn Ile Ala Gln Leu
                245                 250                 255

Ser Gln Asp Asp Ser Gly Arg Tyr Lys Cys Gly Leu Gly Ile Asn Ser
                260                 265                 270

Arg Gly Leu Ser Phe Asp Val Ser Leu Glu Val Ser Gln Gly Pro Gly
                275                 280                 285

Leu Leu Asn Asp Thr Lys Val Tyr Thr Val Asp Leu Gly Arg Thr Val
            290                 295                 300
```

Thr Ile Asn Cys Pro Phe Lys Thr Glu Asn Ala Gln Lys Arg Lys Ser
305                 310                 315                 320

Leu Tyr Lys Gln Ile Gly Leu Tyr Pro Val Leu Val Ile Asp Ser Ser
            325                 330                 335

Gly Tyr Val Asn Pro Asn Tyr Thr Gly Arg Ile Arg Leu Asp Ile Gln
            340                 345                 350

Gly Thr Gly Gln Leu Leu Phe Ser Val Val Ile Asn Gln Leu Arg Leu
            355                 360                 365

Ser Asp Ala Gly Gln Tyr Leu Cys Gln Ala Gly Asp Asp Ser Asn Ser
    370                 375                 380

Asn Lys Lys Asn Ala Asp Leu Gln Val Leu Lys Pro Glu Pro Glu Leu
385                 390                 395                 400

Val Tyr Glu Asp Leu Arg Gly Ser Val Thr Phe His Cys Ala Leu Gly
                405                 410                 415

Pro Glu Val Ala Asn Val Ala Lys Phe Leu Cys Arg Gln Ser Ser Gly
                420                 425                 430

Glu Asn Cys Asp Val Val Asn Thr Leu Gly Lys Arg Ala Pro Ala
    435                 440                 445

Phe Glu Gly Arg Ile Leu Leu Asn Pro Gln Asp Lys Asp Gly Ser Phe
450                 455                 460

Ser Val Val Ile Thr Gly Leu Arg Lys Glu Asp Ala Gly Arg Tyr Leu
465                 470                 475                 480

Cys Gly Ala His Ser Asp Gly Gln Leu Gln Glu Gly Ser Pro Ile Gln
                485                 490                 495

Ala Trp Gln Leu Phe Val Asn Glu Glu Ser Thr Ile Pro Arg Ser Pro
            500                 505                 510

Thr Val Val Lys Gly Val Ala Gly Ser Ser Val Ala Val Leu Cys Pro
            515                 520                 525

Tyr Asn Arg Lys Glu Ser Lys Ser Ile Lys Tyr Trp Cys Leu Trp Glu
    530                 535                 540

Gly Ala Gln Asn Gly Arg Cys Pro Leu Leu Val Asp Ser Glu Gly Trp
545                 550                 555                 560

Val Lys Ala Gln Tyr Glu Gly Arg Leu Ser Leu Leu Glu Glu Pro Gly
                565                 570                 575

Asn Gly Thr Phe Thr Val Ile Leu Asn Gln Leu Thr Ser Arg Asp Ala
            580                 585                 590

Gly Phe Tyr Trp Cys Leu Thr Asn Gly Asp Thr Leu Trp Arg Thr Thr
            595                 600                 605

Val Glu Ile Lys Ile Ile Glu Gly Glu Pro Asn Leu Lys Val Pro Gly
            610                 615                 620

Asn Val Thr Ala Val Leu Gly Glu Thr Leu Lys Val Pro Cys His Phe
625                 630                 635                 640

Pro Cys Lys Phe Ser Ser Tyr Glu Lys Tyr Trp Cys Lys Trp Asn Asn
                645                 650                 655

Thr Gly Cys Gln Ala Leu Pro Ser Gln Asp Glu Gly Pro Ser Lys Ala
            660                 665                 670

Phe Val Asn Cys Asp Glu Asn Ser Arg Leu Val Ser Leu Thr Leu Asn
            675                 680                 685

Leu Val Thr Arg Ala Asp Glu Gly Trp Tyr Trp Cys Gly Val Lys Gln
    690                 695                 700

Gly His Phe Tyr Gly Glu Thr Ala Ala Val Tyr Val Ala Val Glu Glu
705                 710                 715                 720

```
Arg Lys Ala Ala Gly Ser Arg Asp Val Ser Leu Ala Lys Ala Asp Ala
            725                 730                 735

Ala Pro Asp Glu Lys Val Leu Ser Gly Phe Arg Glu Ile Glu Asn
            740                 745                 750

Lys Ala Ile Gln Asp Pro Arg
        755

<210> SEQ ID NO 16
<211> LENGTH: 836
<212> TYPE: PRT
<213> ORGANISM: Artificial Sequence
<220> FEATURE:
<223> OTHER INFORMATION: secretory IgA construct Light chain-(KP6pp)-
      secretory component

<400> SEQUENCE: 16

Asp Ile Leu Leu Thr Gln Ser Pro Ala Ile Leu Ser Val Ser Pro Gly
  1               5                  10                  15

Glu Arg Val Ser Phe Ser Cys Arg Ala Ser Gln Phe Val Gly Ser Ser
                 20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Lys Arg Thr Ile Gln Asp Ser Ala
    210                 215                 220

Thr Asp Thr Val Asp Leu Gly Ala Glu Leu His Arg Asp Asp Pro Pro
225                 230                 235                 240

Pro Thr Ala Ser Asp Ile Gly Lys Arg Gly Gly Lys Ser Pro Ile Phe
                245                 250                 255

Gly Pro Glu Glu Val Asn Ser Val Glu Gly Asn Ser Val Ser Ile Thr
            260                 265                 270

Cys Tyr Tyr Pro Pro Thr Ser Val Asn Arg His Thr Arg Lys Tyr Trp
        275                 280                 285

Cys Arg Gln Gly Ala Arg Gly Gly Cys Ile Thr Leu Ile Ser Ser Glu
    290                 295                 300

Gly Tyr Val Ser Ser Lys Tyr Ala Gly Arg Ala Asn Leu Thr Asn Phe
305                 310                 315                 320
```

```
Pro Glu Asn Gly Thr Phe Val Val Asn Ile Ala Gln Leu Ser Gln Asp
            325                 330                 335

Asp Ser Gly Arg Tyr Lys Cys Gly Leu Gly Ile Asn Ser Arg Gly Leu
            340                 345                 350

Ser Phe Asp Val Ser Leu Glu Val Ser Gln Gly Pro Gly Leu Leu Asn
            355                 360                 365

Asp Thr Lys Val Tyr Thr Val Asp Leu Gly Arg Thr Val Thr Ile Asn
            370                 375                 380

Cys Pro Phe Lys Thr Glu Asn Ala Gln Lys Arg Lys Ser Leu Tyr Lys
385                 390                 395                 400

Gln Ile Gly Leu Tyr Pro Val Leu Val Ile Asp Ser Ser Gly Tyr Val
            405                 410                 415

Asn Pro Asn Tyr Thr Gly Arg Ile Arg Leu Asp Ile Gln Gly Thr Gly
            420                 425                 430

Gln Leu Leu Phe Ser Val Val Ile Asn Gln Leu Arg Leu Ser Asp Ala
            435                 440                 445

Gly Gln Tyr Leu Cys Gln Ala Gly Asp Asp Ser Asn Ser Asn Lys Lys
            450                 455                 460

Asn Ala Asp Leu Gln Val Leu Lys Pro Glu Pro Glu Leu Val Tyr Glu
465                 470                 475                 480

Asp Leu Arg Gly Ser Val Thr Phe His Cys Ala Leu Gly Pro Glu Val
            485                 490                 495

Ala Asn Val Ala Lys Phe Leu Cys Arg Gln Ser Ser Gly Glu Asn Cys
            500                 505                 510

Asp Val Val Val Asn Thr Leu Gly Lys Arg Ala Pro Ala Phe Glu Gly
            515                 520                 525

Arg Ile Leu Leu Asn Pro Gln Asp Lys Asp Gly Ser Phe Ser Val Val
            530                 535                 540

Ile Thr Gly Leu Arg Lys Glu Asp Ala Gly Arg Tyr Leu Cys Gly Ala
545                 550                 555                 560

His Ser Asp Gly Gln Leu Gln Glu Gly Ser Pro Ile Gln Ala Trp Gln
            565                 570                 575

Leu Phe Val Asn Glu Glu Ser Thr Ile Pro Arg Ser Pro Thr Val Val
            580                 585                 590

Lys Gly Val Ala Gly Ser Ser Val Ala Val Leu Cys Pro Tyr Asn Arg
            595                 600                 605

Lys Glu Ser Lys Ser Ile Lys Tyr Trp Cys Leu Trp Glu Gly Ala Gln
            610                 615                 620

Asn Gly Arg Cys Pro Leu Leu Val Asp Ser Glu Gly Trp Val Lys Ala
625                 630                 635                 640

Gln Tyr Glu Gly Arg Leu Ser Leu Leu Glu Glu Pro Gly Asn Gly Thr
            645                 650                 655

Phe Thr Val Ile Leu Asn Gln Leu Thr Ser Arg Asp Ala Gly Phe Tyr
            660                 665                 670

Trp Cys Leu Thr Asn Gly Asp Thr Leu Trp Arg Thr Thr Val Glu Ile
            675                 680                 685

Lys Ile Ile Glu Gly Glu Pro Asn Leu Lys Val Pro Gly Asn Val Thr
            690                 695                 700

Ala Val Leu Gly Glu Thr Leu Lys Val Pro Cys His Phe Pro Cys Lys
705                 710                 715                 720

Phe Ser Ser Tyr Glu Lys Tyr Trp Cys Lys Trp Asn Asn Thr Gly Cys
            725                 730                 735
```

-continued

```
Gln Ala Leu Pro Ser Gln Asp Glu Gly Pro Ser Lys Ala Phe Val Asn
            740                 745                 750

Cys Asp Glu Asn Ser Arg Leu Val Ser Leu Thr Leu Asn Leu Val Thr
        755                 760                 765

Arg Ala Asp Glu Gly Trp Tyr Trp Cys Gly Val Lys Gln Gly His Phe
    770                 775                 780

Tyr Gly Glu Thr Ala Ala Val Tyr Val Ala Val Glu Glu Arg Lys Ala
785                 790                 795                 800

Ala Gly Ser Arg Asp Val Ser Leu Ala Lys Ala Asp Ala Ala Pro Asp
                805                 810                 815

Glu Lys Val Leu Asp Ser Gly Phe Arg Glu Ile Glu Asn Lys Ala Ile
            820                 825                 830

Gln Asp Pro Arg
        835

<210> SEQ ID NO 17
<211> LENGTH: 633
<212> TYPE: PRT
<213> ORGANISM: Artificial Sequence
<220> FEATURE:
<223> OTHER INFORMATION: secretory IgA construct Heavy chain-(KP6pp)-J
      chain

<400> SEQUENCE: 17

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Pro Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255
```

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
        290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Ser Glu Glu Leu Ala Leu Asn Glu Leu
                340                 345                 350

Val Thr Leu Thr Cys Leu Ala Arg Gly Phe Ser Pro Lys Asp Val Leu
                355                 360                 365

Val Arg Trp Leu Gln Gly Ser Gln Glu Leu Pro Arg Glu Lys Tyr Leu
        370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
                420                 425                 430

Gln Lys Thr Ile Asp Arg Leu Ala Gly Lys Pro Thr His Val Asn Val
        435                 440                 445

Ser Val Val Met Ala Glu Val Asp Gly Thr Cys Tyr Gly Gly Lys Arg
450                 455                 460

Thr Ile Gln Asp Ser Ala Thr Asp Thr Val Asp Leu Gly Ala Glu Leu
465                 470                 475                 480

His Arg Asp Asp Pro Pro Thr Ala Ser Asp Ile Gly Lys Arg Gly
                485                 490                 495

Gln Glu Asp Glu Arg Ile Val Leu Val Asp Asn Lys Cys Lys Cys Ala
                500                 505                 510

Arg Ile Thr Ser Arg Ile Ile Arg Ser Ser Glu Asp Pro Asn Glu Asp
        515                 520                 525

Ile Val Glu Arg Asn Ile Arg Ile Val Pro Leu Asn Asn Arg Glu
530                 535                 540

Asn Ile Ser Asp Pro Thr Ser Pro Leu Arg Thr Arg Phe Val Tyr His
545                 550                 555                 560

Leu Ser Asp Leu Cys Lys Lys Cys Asp Pro Thr Glu Val Glu Leu Asp
                565                 570                 575

Asn Gln Ile Val Thr Ala Thr Gln Ser Asn Ile Cys Asp Glu Asp Ser
            580                 585                 590

Ala Thr Glu Thr Cys Tyr Thr Tyr Asp Arg Asn Lys Cys Tyr Thr Ala
                595                 600                 605

Val Val Pro Leu Val Tyr Gly Gly Glu Thr Lys Met Val Glu Thr Ala
        610                 615                 620

Leu Thr Pro Asp Ala Cys Tyr Pro Asp
625                 630

<210> SEQ ID NO 18
<211> LENGTH: 33
<212> TYPE: PRT
<213> ORGANISM: Artificial Sequence
<220> FEATURE:

-continued

```
<223> OTHER INFORMATION: KP6 killer toxing propeptide linker 1

<400> SEQUENCE: 18

Lys Arg Thr Ile Gln Asp Ser Ala Thr Asp Thr Val Asp Leu Gly Ala
1               5                   10                  15

Glu Leu His Arg Asp Asp Pro Pro Thr Ala Ser Asp Ile Gly Lys
            20                  25                  30

Arg

<210> SEQ ID NO 19
<211> LENGTH: 33
<212> TYPE: PRT
<213> ORGANISM: Artificial Sequence
<220> FEATURE:
<223> OTHER INFORMATION: KP6 killer toxin propeptide linker  2

<400> SEQUENCE: 19

Lys Arg Thr Ile Gln Asp Asn Ala Thr Asp Thr Val Asp Leu Gly Ala
1               5                   10                  15

Glu Leu His Arg Asp Asp Pro Pro Thr Ala Ser Asp Ile Gly Lys
            20                  25                  30

Arg

<210> SEQ ID NO 20
<211> LENGTH: 34
<212> TYPE: PRT
<213> ORGANISM: Artificial Sequence
<220> FEATURE:
<223> OTHER INFORMATION: KP6 killer toxin propeptide linker  3

<400> SEQUENCE: 20

Lys Arg Thr Ile Gln Asp Asn Ala Thr Asp Thr Val Asp Leu Gly Ala
1               5                   10                  15

Glu Leu His Arg Asp Asp Pro Pro Thr Asn Val Thr Asp Ile Gly
            20                  25                  30

Lys Arg
```